US012637715B2

(12) United States Patent
Rapisarda et al.

(10) Patent No.: US 12,637,715 B2
(45) Date of Patent: *May 26, 2026

(54) BIOMARKERS AND USES THEREFOR

(71) Applicant: GenoDx Pty Ltd, Vaucluse (AU)

(72) Inventors: Antony Rapisarda, Vaucluse (AU);
Brian Andrew Fox, Seattle, WA (US)

(73) Assignee: GenoDx Pty Ltd, Vaucluse (AU)

( * ) Notice: Subject to any disclaimer, the term of this
patent is extended or adjusted under 35
U.S.C. 154(b) by 0 days.

This patent is subject to a terminal dis-
claimer.

(21) Appl. No.: 18/953,769

(22) Filed: Nov. 20, 2024

(65) Prior Publication Data

US 2025/0101520 A1     Mar. 27, 2025

Related U.S. Application Data

(63) Continuation of application No. 18/705,818, filed as
application No. PCT/AU2022/051312 on Oct. 31,
2022.

(30) Foreign Application Priority Data

| | | |
|---|---|---|
| Oct. 29, 2021 | (WO) | PCT/IB2021/000750 |
| May 3, 2022 | (AU) | 2022901154 |

(51) Int. Cl.
*C12Q 1/6883* (2018.01)
*C12Q 1/6851* (2018.01)

(52) U.S. Cl.
CPC ......... *C12Q 1/6883* (2013.01); *C12Q 1/6851*
(2013.01); *C12Q 2600/112* (2013.01); *C12Q*
*2600/158* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,693,762 A | 12/1997 | Queen et al. | |
| 2002/0055186 A1 | 5/2002 | Barry et al. | |
| 2003/0003599 A1 | 1/2003 | Wagner et al. | |
| 2003/0154032 A1* | 8/2003 | Pittman | C07K 14/4713 |
| | | | 702/20 |
| 2007/0190540 A1 | 8/2007 | Stanley | |
| 2009/0068656 A1 | 3/2009 | Beier et al. | |
| 2015/0218640 A1* | 8/2015 | Brandon | A61P 43/00 |
| | | | 506/7 |
| 2019/0128884 A1 | 5/2019 | Budde et al. | |

FOREIGN PATENT DOCUMENTS

| | | |
|---|---|---|
| WO | WO 1999/039210 | 8/1999 |
| WO | WO 2001/020018 | 3/2001 |
| WO | WO 2002/039120 | 5/2002 |
| WO | WO 2002/048310 | 6/2002 |
| WO | WO 2002/059601 | 8/2002 |
| WO | WO 2003/062444 | 7/2003 |
| WO | WO 2003/077851 | 9/2003 |
| WO | WO 2021/117044 | 6/2021 |
| WO | WO 2001/079849 | 10/2021 |

OTHER PUBLICATIONS

Takeshita et al Ann Rheum Dis. 2019. 78: 1346-1356 (Year: 2019).*
Green, M.R et al ("Nested Polymerase Chain Reaction (PCR)".
Cold Spring Harbor Protocols. Cold Spring Harbor Laboratory
Press, M.R. Green and J. Sambrook, eds, p. 175-178 (Year: 2019).*
Antibody Engineering Protocols, ed. Sudhir, Humana Press, Inc.
1995, TOC Only, 6 pages.
Bockelmann et al., Suprabasal overexpression of the hsRPB7 gene
in psoriatic epidermis as identified by a reverse transcriptase-
polymerase chain reaction differential display model comparing
psoriasis plaque tissue with peritonsillar mucosa. Am J Pathol. Feb.
2001;158(2):367-72.
Bottagisio et al., Phenotypic Modulation of Biofilm Formation in a
*Staphylococcus epidermidis* Orthopedic Clinical Isolate Grown
Under Different Mechanical Stimuli: Contribution From a Com-
bined Proteomic Study. Front Microbiol. Sep. 8, 2020:11:565914.
Cahill, Protein arrays: a thigh-throughput solution for proteomics
research? 2000 Trends in Biotechnology 18(Suppl. 1):47-51.
Carter et al., Humanization of an anti-p185HER2 antibody for
human cancer therapy. Proc Natl Acad Sci U S A. May 15,
1992;89(10):4285-9.
Carulli et al., High throughput analysis of differential gene expres-
sion. J Cell Biochem. 1998;72 Suppl 30-31(S30-31):286-296.
Deirmengian et al., The Mark Coventry Award: white blood cell
gene expression: a new approach toward the study and diagnosis of
infection. Clin Orthop Relat Res. Nov. 2005:440:38-44.
Fodor et al., Light-directed, spatially addressable parallel chemical
synthesis. Science. Feb. 15, 1991;251(4995):767-73.
Ge, UPA, a universal protein array system for quantitative detection
of protein-protein, protein-DNA, protein-RNA and protein-ligand
interactions. Nucleic Acids Res. Jan. 15, 2000;28(2):e3.
Hacia et al., Detection of heterozygous mutations in BRCA1 using
high density oligonucleotide arrays and two-colour fluorescence
analysis. Nat Genet. Dec. 1996;14(4):441-7.
Hanley et al., The meaning and use of the area under a receiver
operating characteristic (ROC) curve. Radiology. Apr. 1982;143(1):29-
36.
Higuchi et al., Simultaneous amplification and detection of specific
DNA sequences. Biotechnology (N Y). Apr. 1992;10(4):413-7.
Jones et al., Replacing the complementarity-determining regions in
a human antibody with those from a mouse. Nature.
1986;321(6069):522-5.

(Continued)

*Primary Examiner* — Carla J Myers
(74) *Attorney, Agent, or Firm* — Casimir Jones, S.C.;
Mary Ann D. Brow

(57) ABSTRACT

This disclosure relates generally to biomarkers of inflam-
matory disease. More particularly, the present disclosure
relates to biomarkers and their use in methods, composi-
tions, apparatuses, devices and kits for determining an
indicator that is useful for assessing a likelihood that a type
of inflammation is present or absent in a joint of a subject.

18 Claims, 14 Drawing Sheets
(9 of 14 Drawing Sheet(s) Filed in Color)

Specification includes a Sequence Listing.

(56)  References Cited

OTHER PUBLICATIONS

Keemu et al., Novel Biomarkers for Diagnosing Periprosthetic Joint Infection from Synovial Fluid and Serum. JB JS Open Access. Apr. 20, 2021;6(2):e20.00067.

Lopez et al., Protein micro- and macroarrays: digitizing the proteome. J Chromatogr B Analyt Technol Biomed Life Sci. Apr. 5, 2003;787(1):19-27.

Mchugh et al., A Molecular Host Response Assay to Discriminate Between Sepsis and Infection-Negative Systemic Inflammation in Critically Ill Patients: Discovery and Validation in Independent Cohorts. PLoS Med. Dec. 8, 2015;12(12):e1001916.

Morrison et al., Chimeric human antibody molecules: mouse antigen-binding domains with human constant region domains. Proc Natl Acad Sci U S A. Nov. 1984;81(21):6851-5.

Nguewa et al., Identification of importin 8 (IPO8) as the most accurate reference gene for the clinicopathological analysis of lung specimens. BMC Mol Biol. Nov. 17, 2008:9:103.

Oppegaard et al., CD64 as a potential biomarker in septic arthritis. BMC Infect Dis. Jun. 19, 2013:13:278.

Pease et al., Light-generated oligonucleotide arrays for rapid DNA sequence analysis. Proc Natl Acad Sci U S A. May 24, 1994;91(11):5022-6.

Sandhu, Protein engineering of antibodies. Crit Rev Biotechnol. 1992;12(5-6):437-62.

Shi et al., NUP58 facilitates metastasis and epithelial-mesenchymal transition of lung adenocarcinoma via the GSK-3β/Snail signaling pathway. Am J Transl Res. Jan. 15, 2019;11(1):393-405.

Shoemaker et al., Quantitative phenotypic analysis of yeast deletion mutants using a highly parallel molecular bar-coding strategy. Nat Genet. Dec. 1996;14(4):450-6.

Singer et al., Optimal humanization of 1B4, an anti-CD18 murine monoclonal antibody, is achieved by correct choice of human V-region framework sequences. J Immunol. Apr. 1, 1993;150(7):2844-57.

Velculescu et al., Serial analysis of gene expression. Science. Oct. 20, 1995;270(5235):484-7.

Xu et al., Vacuolar Protein Sorting 4B (VPS4B) Regulates Apoptosis of Chondrocytes via p38 Mitogen-Activated Protein Kinases (MAPK) in Osteoarthritis. Inflammation. Dec. 2017;40(6):1924-1932.

International Search Report and Written Opinion for PCT/IB2021/000750, mailed Feb. 22, 2022, 17 pages.

International Search Report and Written Opinion for PCT/AU2022/051312, mailed Nov. 30, 2022, 12 pages.

* cited by examiner

Clusters of genes clusters.ap.correlation.mean.6000.gmt

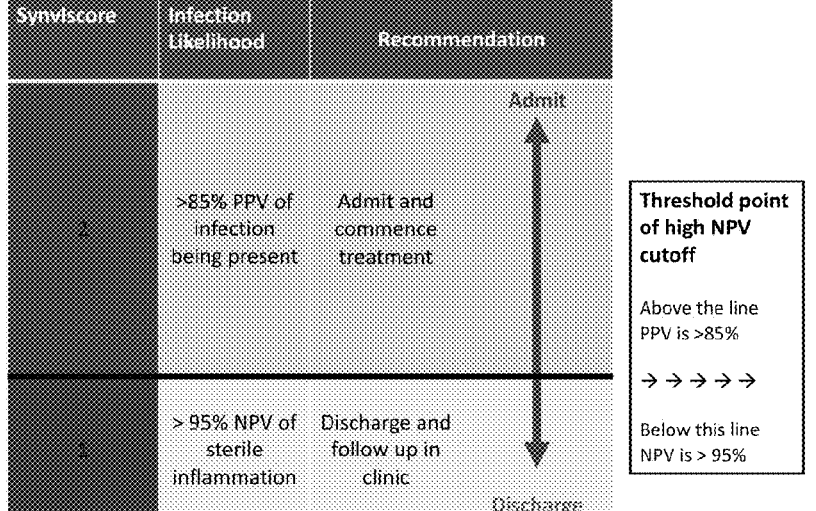

| Synviscore | Infection Likelihood | Recommendation | |
|---|---|---|---|
| 3 | > 80% PPV of infection | Admit and treat these patients urgently | Admit |
| 2 | Indeterminate | Consider re-testing and addition of antibiotics | |
| 1 | >90% NPV of sterile inflammation | Discharge and follow up in clinic | Discharge |

Legend:

Score 3 = higher likelihood of infection requiring immediate treatment with antibiotics Score 2 = increasing likelihood of infection with patient likely requiring admission and antibiotics Score 1 = low likelihood of infection with very high confidence for safe discharge

FIGURE 14

| Synviscore | Infection Likelihood | Recommendation | |
|---|---|---|---|
| 2 | >85% PPV of infection being present | Admit and commence treatment | Admit |
| 1 | > 95% NPV of sterile inflammation | Discharge and follow up in clinic | Discharge |

Threshold point of high NPV cutoff

Above the line PPV is >85%

→ → → → →

Below this line NPV is > 95%

Legend:

Score 2 = higher likelihood of infection requiring admission immediate treatment with antibiotics Score 1 = low likelihood of infection with very high confidence for safe discharge

FIGURE 15

BIOMARKERS AND USES THEREFOR

CROSS REFERENCE TO RELATED APPLICATIONS

This application is a continuation of U.S. application Ser. No. 18/705,818, filed Apr. 29, 2024, which is a § 371 National Entry Application of PCT/AU2022/051312, entitled "Biomarkers and uses therefor" filed 31 Oct. 2022, which claims priority to International Patent Application No. PCT/IB2021/000750 entitled "Biomarkers and uses therefor" filed 29 Oct. 2021 and Australian Provisional Application No. 2022901154 entitled "Biomarkers and uses therefor" filed 3 May 2022, the contents of which are incorporated herein by reference in their entirety.

SEQUENCE LISTING

The text of the computer readable sequence listing filed herewith, titled "Synovial biomarker PCT—Seqlst.xml", created Nov. 12, 2024, having a file size of 18,698 bytes, is hereby incorporated by reference in its entirety.

FIELD

This disclosure relates generally to biomarkers of inflammatory disease. More particularly, the present disclosure relates to biomarkers and their use in methods, compositions, apparatuses, devices and kits for determining an indicator that is useful for assessing a likelihood that a type of inflammation is present or absent in a joint of a subject.

BACKGROUND

Highly accurate and precise differentiation between intra-articular infection and aseptic (i.e., non-infectious) inflammation is currently unavailable and remains a clinically-vexing and challenging day-to-day medical problem. Historically, diagnostic separation of these inflammatory conditions has been based on a composite of clinical assessment/acumen, and formal laboratory testing. The former is prone to the biases and errors of basic human judgment and is considered loosely subjective. The latter is often a costly and time-consuming process with 'definitive' pathological testing results often taking days (and up to 2 weeks) to 'finalize'. This delay potentially puts patients and their joints at considerable interval risk with the potential morbidity of illness and the permanent consequence irreversible joint and cartilage damage. Thus, even with a 'final' diagnosis, conventional microbiological-based diagnosis is fraught with inaccuracy and error (i.e., high false positive and false negative rates [in the order of 80%]) or—arguably worse still—commonly results in an 'inconclusive' outcome. Instigation of incorrect treatment (i.e., treating for 'infection' in the setting of actual aseptic inflammation, or vice versa)—often based on incorrect diagnostic presumptions or test results—can have catastrophic and often permanent sequelae for the patient.

As highlighted in the 2018 International Consensus Meeting on Musculoskeletal Infection: Research Priorities from the General Assembly Questions (*J Orthop Res.* 2019 May; 37 (5): 997-1006), joint-related infections remain the bane of orthopedic surgery, resulting in grievous illness and inordinate costs that threaten healthcare systems, thus representing one of the greatest challenges facing modern orthopedics. In the context of countless presentations for undifferentiated 'joint pain' around the world each year— over 165,000 in the Australian clinical setting (clinical year 2019/2020) alone—there remains an unmet need to provide improved differentiation between infectious and non-infectious joint inflammation to permit early diagnosis, monitoring, making treatment decisions, or management of joint inflammation.

SUMMARY

The present disclosure arises from the determination that certain host response biomarkers from synovial fluid, including RNA transcripts, have strong discrimination performance for specifically differentiating between subjects with infectious inflammation and those with non-infectious or 'sterile' inflammation. In addition, these expression products have high negative predictive value (NPV) and as such, are useful in excluding infection as the cause of the presenting clinical signs of joint inflammation and/or joint pain. Based on these determinations, methods, apparatuses, compositions, devices and kits are disclosed, which take advantage of these biomarkers to determine a likelihood that a type of inflammation is present or absent in joints of subjects presenting with joint pain and/or at least one clinical sign of inflammation in or proximal to the joint. In certain embodiments, the disclosed methods, apparatuses, compositions, devices and kits are used for exclude or 'rule out' the presence of infectious joint inflammation.

Accordingly, in one aspect, disclosed herein are methods for determining an indicator used in assessing a likelihood that a type of inflammation is present or absent in a joint of a subject, wherein the type of inflammation is selected from infectious inflammation and non-infectious inflammation. These methods general comprise, consist or consist essentially of:

(1) determining a biomarker value for at least one biomarker (e.g., 1, 2, 3, 4, 5, 6, 7, 8, 9, 10, 11, 12, 13, 14, 15, 16 or more biomarkers) in a sample obtained from a site of inflammation associated with the joint, wherein a respective biomarker value is indicative of a level of a corresponding biomarker in the sample, wherein the at least one biomarker is selected from a first panel of biomarkers comprising, consisting or consisting essentially of ACO2, AP3M1, ATG4B, C5orf15, CANX, CDKN1A, CSNK1D, CWC27, CXCL8, DTNBP1, DUSP1, EIF2S1, EMP1, ERP44, FCGR3B, FFAR2, FPR1, FYB1, GBP1, H3-3B, HNRNPAB, IARS2, IPO8, IRF2, KCTD2, KCTD3, KLF13, KLHL12, LARP4, LMNA, MCL1, MLLT6, MOCS3, MRPL20, MRPL37, MXD1, MYO1F, NAGA, NAMPT, NINJ1, NUP58, PARP14, PIK3AP1, PIK3R5, PIP4K2B, PKN1, PLEC, PLXDC2, POLG2, POLR2G, PPIL2, PPP5C, PRPF19, PSMC3, RILPL2, RNASEL, RNF26, SEC24B, SLC26A6, SNIP1, SNRPF, SP1, SP2, STX11, SUSD6, TBK1, TNFRSF1B, TTYH3, TWF2, VPS4B, VPS51, WIPF2 and ZZEF1; and (2) determining the indicator using the biomarker value(s).

Advantageously, the methods distinguish between a likelihood that infectious inflammation is present or absent in a joint of a subject and a likelihood that non-infectious inflammation is present or absent in the joint of the subject. For example, the indicator determined using the biomarker value(s) may indicate a likelihood that infectious inflammation is present in the joint of the subject and/or a likelihood that non-infectious inflammation is absent in the joint of the subject. Alternatively, the determined indicator may indicate a likelihood that infectious inflammation is absent in the joint of the subject and/or a likelihood that non-infectious inflammation is present in the joint of the subject.

Suitably, the subject has joint pain and/or at least one clinical sign of inflammation (e.g., acute inflammation) in, or proximal to, the joint. The inflammation may comprise one or more of redness, increased heat, swelling, pain and loss of function in, or proximal to, the joint. The joint may be a native joint or a prosthetic joint.

In some embodiments, biomarker values are obtained for a plurality of biomarkers, wherein the plurality of biomarkers is selected from the first panel of biomarkers and optionally from a second panel of biomarkers comprising API5, AQP9, ATIC, CISH, CLIC4, CSF2RB, CSF3R, DUSP5, ETV6, GADD45B, GRINA, HCK, HLA-E, IER3, IL1B, IL1RN, IMMT, LILRB3, LRPPRC, LYN, NFKBIA, OSM, PDE4B, PI3, PLAUR, PLEK, PPIF, SEMA4D, STARD7, TNFAIP2, TNFAIP3 and ZFP36.

In some embodiments, biomarker values are determined for at least two, three, four, five, six, seven or eight biomarkers.

In some embodiments, biomarker values are determined for a first biomarker and a second biomarker, wherein the first biomarker is selected from a first set of biomarkers that are expressed at a higher level in infectious inflammation than in non-infectious inflammation, and wherein the second biomarker is selected from a second set of biomarkers that are expressed at a lower level in infectious inflammation than in non-infectious inflammation, and/or from a third set of biomarkers that improve the discrimination performance of the first biomarker, wherein the first set of biomarkers comprises, consists or consists essentially of AQP9, C5orf15, CANX, CDKN1A, CISH, CLIC4, CSF2RB, CSF3R, CXCL8, DTNBP1, DUSP1, DUSP5, ERP44, ETV6, FCGR3B, FFAR2, FPR1, FYB1, GADD45B, GBP1, GRINA, H3-3B, HCK, HLA-E, IRF2, LILRB3, LYN, MCL1, MLLT6, MXD1, NAMPT, NFKBIA, NINJ1, NUP58, PARP14, PDE4B, PI3, PIK3AP1, PIK3R5, PLAUR, PLEK, RILPL2, RNASEL, SEMA4D, SP2, STX11, SUSD6, TBK1, TNFAIP2, TNFAIP3, TNFRSF1B and WIPF2, wherein the second set of biomarkers comprises, consists or consists essentially of ACO2, AP3M1, API5, ATIC, CWC27, EIF2S1, EMP1, HNRNPAB, IARS2, KLF13, LARP4, LMNA, LRPPRC, MOCS3, MRPL20, MRPL37, NAGA, PIP4K2B, PKN1, PLEC, PLXDC2, PPIL2, PPP5C, PRPF19, RNF26, STARD7, TTYH3, TWF2, VPS51 and ZZEF1, and wherein the third set of biomarkers comprises, consists or consists essentially of CSNK1D, MYO1F and POLR2G.

In other embodiments, biomarker values are determined for a first biomarker, a second biomarker, a third biomarker and optionally a fourth biomarker, wherein the first and second biomarkers are selected from a first set of biomarkers that are expressed at a higher level in infectious inflammation than in non-infectious inflammation, and wherein the third and optional fourth biomarkers are selected from a second set of biomarkers that are expressed at a lower level in infectious inflammation than in non-infectious inflammation, and/or a third set of biomarkers that improve the discrimination performance of the first and/or second biomarkers, wherein the first set of biomarkers comprises, consists or consists essentially of AQP9, C5orf15, CANX, CDKN1A, CISH, CLIC4, CSF2RB, CSF3R, CXCL8, DTNBP1, DUSP1, DUSP5, ERP44, ETV6, FCGR3B, FFAR2, FPR1, FYB1, GADD45B, GBP1, GRINA, H3-3B, HCK, HLA-E, IRF2, LILRB3, LYN, MCL1, MLLT6, MXD1, NAMPT, NFKBIA, NINJ1, NUP58, PARP14, PDE4B, PI3, PIK3AP1, PIK3R5, PLAUR, PLEK, RILPL2, RNASEL, SEMA4D, SNIP1, SP1, SP2, STX11, SUSD6, TBK1, TNFAIP2, TNFAIP3, TNFRSF1B and WIPF2, wherein the second set of biomarkers comprises, consists or consists essentially of ACO2, AP3M1, API5, ATIC, CWC27, EIF2S1, EMP1, IMMT, KLF13, LARP4, LMNA, LRPPRC, MOCS3, MRPL20, MRPL37, NAGA, PIP4K2B, PKN1, PLEC, PLXDC2, PPIL2, PPP5C, PRPF19, PSMC3, RNF26, SNRPF, STARD7, TTYH3, TWF2 and VPS51, and wherein the third set of biomarkers comprises, consists or consists essentially of ATG4B, CSNK1D, IPO8, KCTD2, MYO1F, POLG2, POLR2G and ZZEF1.

In still other embodiments, biomarker values are determined for a first biomarker, a second biomarker, a third biomarker, optionally a fourth biomarker, a fifth biomarker, a sixth biomarker and optionally one or both of a seventh biomarker and an eighth biomarker, wherein the first biomarker, second biomarker, third biomarker and optional fourth biomarker are selected from a first set of biomarkers that are expressed at a higher level in infectious inflammation than in non-infectious inflammation, and wherein the fifth biomarker, sixth biomarker and optional seventh and eighth biomarkers are selected from a second set of biomarkers that are expressed at a lower level in infectious inflammation than in non-infectious inflammation, and/or from a third set of biomarkers that improve the discrimination performance of the first biomarker, second biomarker, third biomarker and optional fourth biomarker, wherein the first set of biomarkers comprises, consists or consists essentially of AQP9, C5orf15, CANX, CDKN1A, CISH, CLIC4, CSF2RB, CSF3R, CXCL8, DTNBP1, DUSP1, DUSP5, EMP1, ERP44, ETV6, FCGR3B, FFAR2, FPR1, FYB1, GADD45B, GRINA, H3-3B, HCK, HLA-E, IER3, IL1B, IL1RN, IRF2, LILRB3, LMNA, LYN, MCL1, MLLT6, MXD1, NAMPT, NFKBIA, NINJ1, NUP58, OSM, PDE4B, PI3, PIK3AP1, PLAUR, PLEK, PPIF, RILPL2, RNASEL, SEMA4D, SNIP1, SP1, SP2, STX11, SUSD6, TNFAIP2, TNFAIP3, TNFRSF1B, WIPF2 and ZFP36 wherein the second set of biomarkers comprises, consists or consists essentially of ACO2, AP3M1, API5, EIF2S1, IMMT, KCTD3, KLF13, MOCS3, MRPL20, PKN1, PLEC, PPP5C, PSMC3, RNF26, SNRPF, STARD7 and TTYH3, and wherein the third set of biomarkers comprises, consists or consists essentially of ATG4B, CSNK1D, IPO8, KLHL12, MYO1F, POLG2, POLR2G, SEC24B, SLC26A6, VPS4B and ZZEF1.

In some embodiments, the methods further comprise applying a function to biomarker values to yield at least one functionalized biomarker value and determining the indicator using the at least one functionalized biomarker value. In representative examples, the function includes at least one of: (a) multiplying biomarker values; (b) dividing biomarker values; (c) adding biomarker values; (d) subtracting biomarker values; (e) a weighted sum of biomarker values; (f) a log sum of biomarker values; (g) a geometric mean of biomarker values; and (h) a sigmoidal function of biomarker values.

In some embodiments, the methods further comprise combining the biomarker values to provide a composite score and determining the indicator using the composite score. In non-limiting examples of this type, the biomarker values are combined by adding, multiplying, subtracting, and/or dividing biomarker values.

Individual biomarker values may represent a measured amount or concentration of a corresponding biomarker in the sample. Alternatively, individual biomarker values may be a logarithmic representation of a measured amount or concentration of a corresponding biomarker in the sample.

In some embodiments, the methods comprise analyzing the biomarker value(s) or composite score with reference to one or more suitable corresponding controls, to determine the indicator. An individual control may comprise a reference biomarker value range or cut-off value, or a reference composite score range or cut-off value.

Suitably, the indicator indicates a likelihood of a presence of infectious inflammation if the biomarker value(s) or composite score is indicative of the level of the biomarker(s) in the sample that correlates with an increased likelihood of a presence of infectious inflammation relative to a suitable control (e.g., a predetermined reference biomarker value range or cut-off value), and wherein the indicator indicates a likelihood of the presence of non-infectious inflammation if the biomarker value(s) or composite score is (are) indicative of the level of the biomarker(s) in the sample that correlates with an increased likelihood of the presence of non-infectious inflammation relative to a suitable control (e.g., a predetermined reference biomarker value range or cut-off value). In some embodiments, the methods may comprise ruling out the likelihood of infectious joint inflammation in the subject or not, based on the indicator.

The joint may be a synovial joint, a fibrous joint or a cartilaginous joint. In some embodiments, the synovial joint is a knee joint, wrist joint, shoulder joint, hip joint, elbow joint or ankle joint. In specific embodiment, the synovial joint is a knee joint.

The sample may comprise synovial fluid, lymph fluid, joint exudate, joint transudate, or combination thereof. Suitably, the sample comprises leukocytes.

Disclosed herein in another aspect are apparatuses for determining an indicator used in assessing a likelihood that a type of inflammation is present or absent in a joint of a subject, wherein the type of inflammation is selected from infectious inflammation and non-infectious inflammation. These apparatuses general comprise, consist or consist essentially of at least one electronic processing device that performs steps of the indicator-determining methods described herein. For example, the at least one electronic processing device may:

determine a biomarker value for at least one biomarker (e.g., 1, 2, 3, 4, 5, 6, 7, 8, 9, 10, 11, 12, 13, 14, 15, 16 or more biomarkers) in a sample obtained from a site of inflammation associated with the joint, wherein a respective biomarker value is indicative of a level of a corresponding biomarker in the sample, wherein the at least one biomarker is selected from a first panel of biomarkers comprising, consisting or consisting essentially of ACO2, AP3M1, ATG4B, C5orf15, CANX, CDKN1A, CSNK1D, CWC27, CXCL8, DTNBP1, DUSP1, EIF2S1, EMP1, ERP44, FCGR3B, FFAR2, FPR1, FYB1, GBP1, H3-3B, HNRNPAB, IARS2, IPO8, IRF2, KCTD2, KCTD3, KLF13, KLHL12, LARP4, LMNA, MCL1, MLLT6, MOCS3, MRPL20, MRPL37, MXD1, MYO1F, NAGA, NAMPT, NINJ1, NUP58, PARP14, PIK3AP1, PIK3R5, PIP4K2B, PKN1, PLEC, PLXDC2, POLG2, POLR2G, PPIL2, PPP5C, PRPF19, PSMC3, RILPL2, RNASEL, RNF26, SEC24B, SLC26A6, SNIP1, SNRPF, SP1, SP2, STX11, SUSD6, TBK1, TNFRSF1B, TTYH3, TWF2, VPS4B, VPS51, WIPF2 and ZZEF1; and.

determine the indicator using the derived biomarker value(s).

In some embodiments, the at least one electronic processing device:

determines biomarker values for a plurality of biomarkers, wherein the plurality of biomarkers is selected from the first panel of biomarkers and optionally from a second panel of biomarkers comprising API5, AQP9, ATIC, CISH, CLIC4, CSF2RB, CSF3R, DUSP5, ETV6, GADD45B, GRINA, HCK, HLA-E, IER3, IL1B, IL1RN, IMMT, LILRB3, LRPPRC, LYN, NFKBIA, OSM, PDE4B, PI3, PLAUR, PLEK, PPIF, SEMA4D, STARD7, TNFAIP2, TNFAIP3 and ZFP36.

In yet another aspect, disclosed herein are compositions for determining an indicator used in assessing a likelihood that a type of inflammation is present or absent in a joint of a subject, wherein the type of inflammation is selected from infectious inflammation and non-infectious inflammation. These compositions generally comprise, consist or consist essentially of a mixture of a DNA polymerase (e.g., a thermostable DNA polymerase), synovial fluid leukocyte cDNA from a subject with joint pain and/or at least one clinical sign of inflammation (e.g., acute inflammation) in, or proximal to, the joint, wherein the synovial fluid leukocyte cDNA comprises at least one cDNA (e.g., 1, 2, 3, 4, 5, 6, 7, 8, 9, 10, 11, 12, 13, 14, 15, 16 or more cDNA) selected from a first panel of cDNA biomarkers comprising, consisting or consisting essentially of ACO2, AP3M1, ATG4B, C5orf15, CANX, CDKN1A, CSNK1D, CWC27, CXCL8, DTNBP1, DUSP1, EIF2S1, EMP1, ERP44, FCGR3B, FFAR2, FPR1, FYB1, GBP1, H3-3B, HNRNPAB, IARS2, IPO8, IRF2, KCTD2, KCTD3, KLF13, KLHL12, LARP4, LMNA, MCL1, MLLT6, MOCS3, MRPL20, MRPL37, MXD1, MYO1F, NAGA, NAMPT, NINJ1, NUP58, PARP14, PIK3AP1, PIK3R5, PIP4K2B, PKN1, PLEC, PLXDC2, POLG2, POLR2G, PPIL2, PPP5C, PRPF19, PSMC3, RILPL2, RNASEL, RNF26, SEC24B, SLC26A6, SNIP1, SNRPF, SP1, SP2, STX11, SUSD6, TBK1, TNFRSF1B, TTYH3, TWF2, VPS4B, VPS51, WIPF2 and ZZEF1, and wherein the composition further comprises for the at least one cDNA of the first panel of cDNA biomarkers at least one oligonucleotide primer and/or at least one probe that hybridizes to the cDNA.

In some embodiments, the synovial fluid leukocyte cDNA comprises at least one cDNA (e.g., 1, 2, 3, 4, 5, 6, 7, 8, 9, 10, 11, 12, 13, 14, 15, 16 or more cDNA) selected from a second panel of cDNA biomarkers comprising API5, AQP9, ATIC, CISH, CLIC4, CSF2RB, CSF3R, DUSP5, ETV6, GADD45B, GRINA, HCK, HLA-E, IER3, IL1B, IL1RN, IMMT, LILRB3, LRPPRC, LYN, NFKBIA, OSM, PDE4B, PI3, PLAUR, PLEK, PPIF, SEMA4D, STARD7, TNFAIP2, TNFAIP3 and ZFP36, and wherein the composition further comprises for the at least one cDNA of the second panel of cDNA biomarkers at least one oligonucleotide primer or probe that hybridizes to the cDNA.

In some embodiments, the compositions comprise for a respective cDNA two oligonucleotide primers that hybridize to opposite complementary strands of the cDNA. In some embodiments, the compositions comprise for a respective cDNA two pairs of oligonucleotide primers, wherein the oligonucleotide primers of a respective pair hybridize to opposite complementary strands of the cDNA, and wherein the oligonucleotide primers of one pair are nested ("nested oligonucleotide primers") relative the oligonucleotide primers of the other pair. In some of the same or other embodiments, the compositions comprise for a respective cDNA an oligonucleotide probe that hybridizes to the cDNA or a polynucleotide corresponding thereto (e.g., a polynucleotide product resulting from nucleic acid amplification of the cDNA). The oligonucleotide probe may comprise a heterologous label (e.g., a fluorescent label). In embodiments in which the oligonucleotide probe comprises a heterologous label, the labeled oligonucleotide probe may comprise a fluorophore. In representative examples of this type, the labeled oligonucleotide probe further comprises a quencher. In certain embodiments, different labeled oligonucleotide probes are included in the composition for hybridizing to different cDNAs, wherein individual oligonucleotide probes comprise detectably distinct labels (e.g. different fluorophores), or at least a subset of oligonucleotide probes comprises the same label (e.g. same fluorophore). In some embodiments, the compositions comprise for each of at least 2, 3, 4, 5, 6, 7, 8, 9, 10, 11, 12, 13, 14, 15 or 16 of the cDNAs at least one oligonucleotide primer and/or at least one oligonucleotide probe that hybridizes to the cDNA. In other embodiments, the compositions comprise for each of up to 2, 3, 4, 5, 6, 7, 8, 9, 10, 11, 12, 13, 14, 15 or 16 of the cDNAs at least one oligonucleotide primer and/or at least one oligonucleotide probe that hybridizes to the cDNA. Individual cDNAs and their corresponding oligonucleotide primer(s) and/or probe(s) may be present in separate reaction vessels or in the same reaction vessel.

In still another aspect, devices are disclosed for nucleic acid amplification of synovial fluid leukocyte cDNA. These devices comprise a plurality of reaction vessels, wherein individual reaction vessels comprise a composition as broadly described above and elsewhere herein. Devices disclosed herein may consist of 2 to 100, 2 to 50, 2 to 40, 2 to 30, 2 to 20, 2 to 15, 2 to 12, 2 to 10 or 2 to 8 reaction vessels (and all integer vessels in between). In non-limiting examples, the devices consist of 2, 4, 5, 6, 7, 8, 9, 10, 11, 12, 13, 14, 15 or 16 reaction vessels. In representative examples of this type, one or more reaction vessels are used for single-plex amplification of cDNA, and/or one or more reaction vessels are used for multiplex amplification of CDNA (e.g., 2-plex, 3-plex, 4-plex, 5-plex or 6-plex amplifications).

In a further aspect, methods are disclosed for inhibiting the development or progression of infectious inflammation or non-infectious inflammation in a subject with joint pain and/or at least one clinical sign of inflammation (e.g., acute inflammation) in, or proximal to, the joint. These methods generally comprise, consist or consist essentially of:

(1) exposing the subject to a treatment regimen for infectious inflammation at least in part on the basis that the subject is determined by the indicator-determining method as broadly described above and elsewhere herein as having a likelihood of a presence of infectious inflammation; or (2) exposing the subject to a treatment regimen for non-infectious inflammation at least in part on the basis that the subject is determined by the indicator-determining method as broadly described above and elsewhere herein as having a likelihood of a presence of non-infectious inflammation.

In some embodiments, the methods further comprise: taking a sample from the subject and determining an indicator indicative of a likelihood of a presence of infectious inflammation or indicative of a likelihood of a presence of non-infectious inflammation using the indicator-determining method. In some of the same or other embodiments, the methods further comprise: sending a sample obtained from the subject to a laboratory at which the indicator is determined according to the indicator-determining method, and optionally receiving the indicator from the laboratory.

Disclosed herein in still another aspect are kits for determining an indicator used in assessing a likelihood that a type of inflammation is present or absent in a joint of a subject, wherein the type of inflammation is selected from infectious inflammation and non-infectious inflammation, the kit comprising: (1) for each of at least one nucleic acid biomarker (e.g., 1, 2, 3, 4, 5, 6, 7, 8, 9, 10, 11, 12, 13, 14, 15, 16 or more biomarkers) at least one oligonucleotide primer and/or at least one oligonucleotide probe that hybridizes to the nucleic acid biomarker, wherein the at least one biomarker is selected from a first panel of biomarkers comprising, consisting or consisting essentially of ACO2, AP3M1, ATG4B, C5orf15, CANX, CDKN1A, CSNK1D, CWC27, CXCL8, DTNBP1, DUSP1, EIF2S1, EMP1, ERP44, FCGR3B, FFAR2, FPR1, FYB1, GBP1, H3-3B, HNRNPAB, IARS2, IPO8, IRF2, KCTD2, KCTD3, KLF13, KLHL12, LARP4, LMNA, MCL1, MLLT6, MOCS3, MRPL20, MRPL37, MXD1, MYO1F, NAGA, NAMPT, NINJ1, NUP58, PARP14, PIK3AP1, PIK3R5, PIP4K2B, PKN1, PLEC, PLXDC2, POLG2, POLR2G, PPIL2, PPP5C, PRPF19, PSMC3, RILPL2, RNASEL, RNF26, SEC24B, SLC26A6, SNIP1, SNRPF, SP1, SP2, STX11, SUSD6, TBK1, TNFRSF1B, TTYH3, TWF2, VPS4B, VPS51, WIPF2 and ZZEF1.

In some embodiments, the kits comprise at least one oligonucleotide primer and/or at least one oligonucleotide probe for each of a plurality of biomarkers (e.g., at least 2, 3, 4, 5, 6, 7, 8, 9, 10, 11, 12, 13, 14, 15 or 16 biomarkers, or up to 2, 3, 4, 5, 6, 7, 8, 9, 10, 11, 12, 13, 14, 15 or 16 biomarkers), wherein the plurality of biomarkers is selected from the first panel of biomarkers and optionally from a second panel of biomarkers comprising API5, AQP9, ATIC, CISH, CLIC4, CSF2RB, CSF3R, DUSP5, ETV6, GADD45B, GRINA, HCK, HLA-E, IER3, IL1B, IL1RN, IMMT, LILRB3, LRPPRC, LYN, NFKBIA, OSM, PDE4B, PI3, PLAUR, PLEK, PPIF, SEMA4D, STARD7, TNFAIP2, TNFAIP3 and ZFP36.

The kits may further comprise any one or more of: a DNA polymerase (e.g., a thermostable DNA polymerase); for each nucleic acid biomarker a pair of forward and reverse oligonucleotide primers that permit nucleic acid amplification of at least a portion of the nucleic acid biomarker to produce an amplicon; for each nucleic acid biomarker two pairs of forward and reverse oligonucleotide primers, wherein the oligonucleotide primers of one pair are nested ("nested oligonucleotide primers") relative to the oligonucleotide primers of the other pair, wherein a respective pair of oligonucleotide primers permits nucleic acid amplification of at least a portion of the nucleic acid biomarker to produce an amplicon; for each nucleic acid biomarker an oligonucleotide probe that comprises a heterologous label and hybridizes to the nucleic acid biomarker or an amplicon of the nucleic acid biomarker; one or more reagents for preparing mRNA from a cell or cell population from a sample obtained from a site of inflammation associated with the joint of the subject; one or more reagents for preparing cDNA from the mRNA; one or more reagents for amplifying cDNA; and one or more of deoxynucleotides, buffer(s), positive and negative controls, and reaction vessel(s). Suitably, the kits may further comprise instructions for performing the indicator-determining method as broadly described above and elsewhere herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 14 is an illustration of one example output depicting an indicator that is useful for assessing the likelihood of infectious joint inflammation or non-infectious joint inflammation in a patient.

FIG. 15 is an illustration of another example output depicting an indicator that is useful for assessing the likelihood of infectious joint inflammation or non-infectious joint inflammation in a patient.

DETAILED DESCRIPTION

1. Definitions

Figure 1:
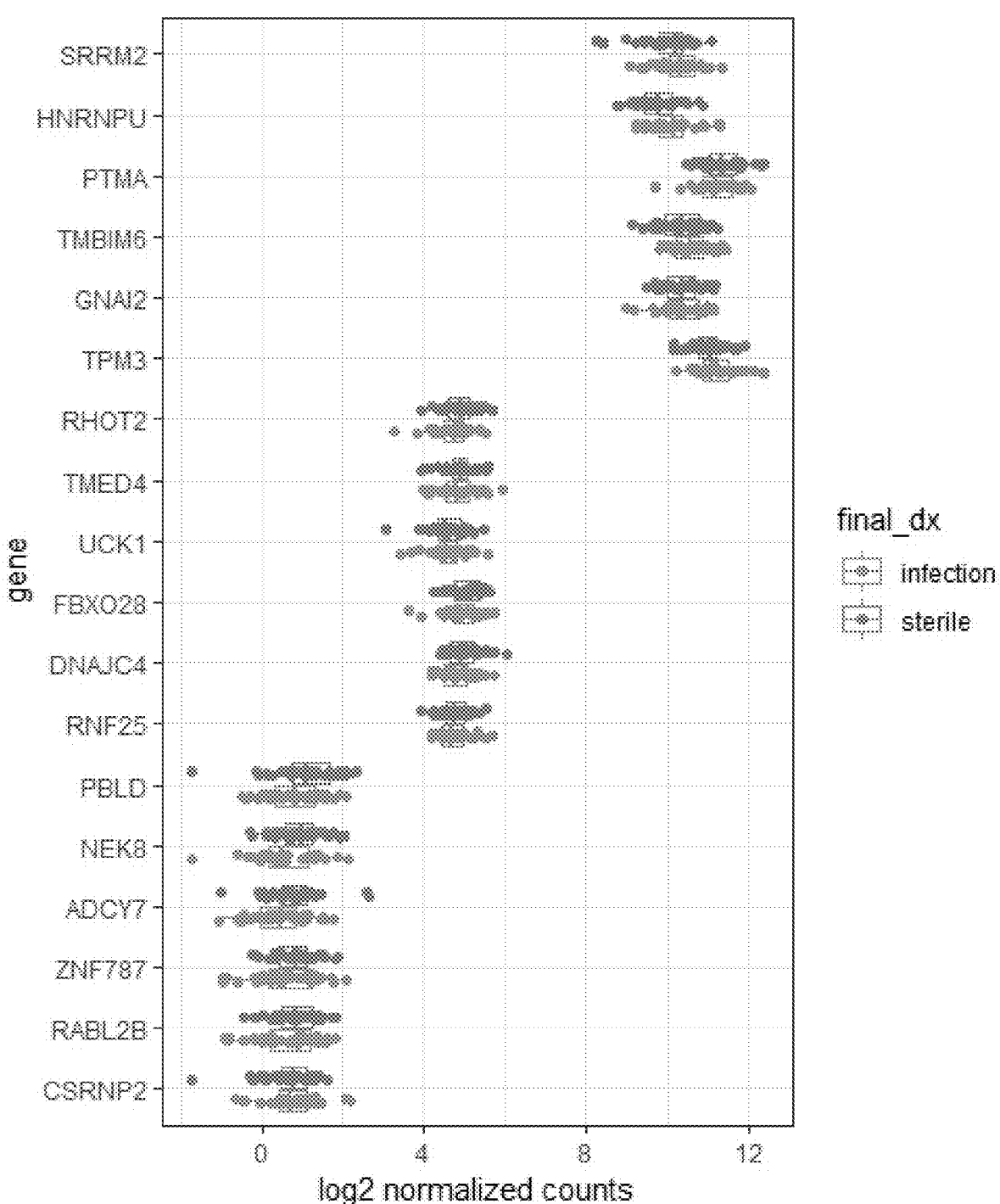
FIG. 1 is a graphical representation showing expression levels of ADCY7, CSRNP2, DNAJC4, FBXO28, GNAI2, HNRNPU, NEK8, PBLD, PTMA, RABL2B, RHOT2, RNF25, SRRM2, TMBIM6, TMED4, TPM3, UCK1, ZNF787 in subjects with infectious joint inflammation and in subjects with non-infectious joint inflammation.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, preferred methods and materials are described. For the purposes of the present disclosure, the following terms are defined below.

Unless defined otherwise, all technical and scientific terms used herein have the same meaning as commonly understood by those of ordinary skill in the art to which the present disclosure belongs. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

The term "aiding diagnosis" is used herein to refer to methods that assist in making a clinical determination regarding the presence, or nature, of a particular type of symptom or condition of a disease or disorder (e.g., infectious joint inflammation or non-infectious joint inflammation). For example, a method of aiding diagnosis of a disease or condition (e.g., infectious joint inflammation or non-infectious joint inflammation) can comprise measuring certain biomarkers (e.g., the joint inflammation biomarkers disclosed herein) in a biological sample of an individual.

The "amount" or "level" of a biomarker is a detectable level or amount in a sample. These can be measured by methods known to one skilled in the art and also disclosed herein. These terms encompass a quantitative amount or level (e.g., weight or moles), a semi-quantitative amount or level, a relative amount or level (e.g., weight % or mole % within class), a concentration, and the like. Thus, these terms encompass absolute or relative amounts or levels or concentrations of a biomarker in a sample. The expression level or amount of biomarker assessed can be used to determine the response to treatment.

"Amplification," as used herein generally refers to the process of producing multiple copies of a desired sequence.

"Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

As used herein, the term "amplicon" refers to a nucleic acid that is the product of amplification. Thus an amplicon may be homologous to a reference sequence, a target sequence, or any sequence of nucleic acid that has been subjected to amplification. Generally, within a reaction sample, the concentration of amplicon sequence will be significantly greater than the concentration of original (template) nucleic acid sequence.

As used herein, "and/or" refers to and encompasses any and all possible combinations of one or more of the associated listed items, as well as the lack of combinations when interpreted in the alternative (or).

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity. Representative antigen-binding molecules that are useful in the practice of the present disclosure include polyclonal and monoclonal antibodies as well as their fragments (such as Fab, Fab', F(ab')$_2$, Fv), single chain (scFv) and domain antibodies (including, for example, shark and camelid antibodies), and fusion proteins comprising an antibody, and any other modified configuration of the immunoglobulin molecule that comprises an antigen binding/recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called α, δ, ε, γ, and μ, respectively. The subunit structures and three-dimensional configurations of different classes of immunoglobulins are well known. Antigen-binding molecules also encompass dimeric antibodies, as well as multivalent forms of antibodies. In some embodiments, the antigen-binding molecules are chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, for example, U.S. Pat. No. 4,816,567; and Morrison et al., 1984, *Proc. Natl. Acad. Sci. USA* 81:6851-6855). Also contemplated, are humanized antibodies, which are generally produced by transferring complementarity determining regions (CDRs) from heavy and light variable chains of a non-human (e.g., rodent, preferably mouse) immunoglobulin into a human variable domain. Typical residues of human antibodies are then substituted in the framework regions of the non-human counterparts. The use of antibody components derived from humanized antibodies obviates potential problems associated with the immunogenicity of non-human constant regions. General techniques for cloning non-human, particularly murine, immunoglobulin variable domains are described, for example, by Orlandi et al. (1989, *Proc. Natl. Acad. Sci. USA* 86:3833). Techniques for producing humanized monoclonal antibodies are described, for example, by Jones et al. (1986, *Nature* 321: 522), Carter et al. (1992, *Proc. Natl. Acad. Sci. USA* 89:4285), Sandhu (1992, *Crit. Rev. Biotech.* 12:437), Singer et al. (1993, *J. Immun.* 150:2844), Sudhir (ed., Antibody Engineering Protocols, Humana Press, Inc. 1995), Kelley ("Engineering Therapeutic Antibodies," in Protein Engineering: Principles and Practice Cleland et al. (eds.), pages 399-434 (John Wiley & Sons, Inc. 1996), and by Queen et al., U.S. Pat. No. 5,693,762 (1997). Humanized antibodies include "primatized" antibodies in which the antigen-binding region of the antibody is derived from an antibody produced by immunizing macaque monkeys with the antigen of interest. Also contemplated as antigen-binding molecules are humanized antibodies.

The term "biomarker" as used herein refers to an indicator agent, substance, compound or molecule, e.g., a predictive, diagnostic, and/or prognostic agent, substance, compound or molecule, which can be detected in a sample. The presence absence or level of the biomarker may serve as an indicator of a particular subtype of a disease or disorder (e.g., infectious inflammation or non-infectious inflammation, etc.), characterized by certain, molecular, pathological, histological, and/or clinical features, and/or may serve as an indicator of a particular cell type or state and/or or response to therapy. Biomarkers include, but are not limited to, polynucleotides (e.g., DNA, and/or RNA), polynucleotide copy number alterations (e.g., DNA copy numbers), polypeptides, polypeptide and polynucleotide modifications (e.g., posttranslational modifications), carbohydrates, and/or glycolipid-based molecular markers. A biomarker may be present in a sample obtained from a subject before the onset of a physiological or pathophysiological state (e.g., infectious inflammation or non-infectious inflammation, etc.), including a symptom, thereof (e.g., joint pain, joint inflammation, etc.). Thus, the presence of the biomarker in a sample obtained from the subject can be indicative of an increased risk that the subject will develop the physiological or pathophysiological state or symptom thereof. Alternatively, or in addition, the biomarker may be normally expressed in an individual, but its expression may change (i.e., it is increased (upregulated; over-expressed) or decreased (downregulated; under-expressed) before the onset of a physiological or pathophysiological state, including a symptom thereof. Thus, a change in the level of the biomarker may be indicative of an increased risk that the subject will develop the physiological or pathophysiological state or symptom thereof. Alternatively, or in addition, a change in the level of a biomarker may reflect a change in a particular physiological or pathophysiological state, or symptom thereof, in a subject, thereby allowing the nature (e.g., severity) of the physiological or pathophysiological state, or symptom thereof, to be tracked over a period of time. This approach may be useful in, for example, monitoring a treatment regimen for the purpose of assessing its effectiveness (or otherwise) in a subject. As herein described, reference to the level of a biomarker includes the concentration of a biomarker, or the level of expression of a biomarker, or the activity of the biomarker.

The term "biomarker value" refers to a value measured or functionalized for at least one corresponding biomarker of a subject and which is typically indicative of an abundance or concentration of a biomarker in a sample obtained from the subject. Thus, the biomarker values could be measured biomarker values, which are values of biomarkers measured for the subject. These values may be quantitative or qualitative. For example, a measured biomarker value may refer to the presence or absence of a biomarker or may refer to a level of a biomarker, in a sample. The measured biomarker values can be values relating to raw or normalized biomarker levels (e.g., a raw, non-normalized biomarker level, or a normalized biomarker levels that is determined relative to an internal or external control biomarker level) and to mathematically transformed biomarker levels (e.g., a logarithmic representation of a biomarker level such as amplification amount, cycle time, etc.). Alternatively, the biomarker values could be functionalized biomarker values, which are values that have been functionalized from one or more measured biomarker values, for example by applying a function to the one or more measured biomarker values. Biomarker values can be of any appropriate form depending on the manner in which the values are determined. For example, the biomarker values could be determined using high-throughput technologies such as mass spectrometry, sequencing platforms, array and hybridization platforms, immunoassays, flow cytometry, or any combination of such technologies and in representative examples, the biomarker values relate to a level of activity or abundance of an expression product or other measurable molecule, quantified using a nucleic acid assay such as real-time polymerase chain reaction (RT-PCR), sequencing or the like. In the context of nucleic acid amplification assays such as PCR-based assays, the biomarker values can be in the form of amplification amounts, or cycle times, which are a logarithmic representation of the levels of the biomarker within a sample and which thus correspond to mathematical transformations of raw or normalized biomarker levels, as will be appreciated by persons skilled in the art. Thus, in situations in which mathematically transformed biomarker values are used as measured biomarker values, the expression "functionalized biomarker value" in the context, for example, of a ratio of levels of a pair of biomarkers in a sample obtained from a subject does not necessarily mean that the functionalized biomarker value is one that results from a division of one measured biomarker value by another measured biomarker value. Instead, the measured biomarker values can be combined using any suitable function, whereby the resulting functionalized biomarker value is one that corresponds to or reflects a ratio of non-normalized (e.g., raw) or normalized biomarker levels.

The terms "biomarker signature", "signature", "biomarker expression signature", or "expression signature" are used interchangeably herein and refer to one or a combination of biomarkers the expression of which provides an indicator, e.g., a predictive, diagnostic, and/or prognostic indicator. The biomarker signature may serve as an indicator of a particular subtype of a disease or disorder (e.g., infectious inflammation or non-infectious inflammation, etc.) or symptom thereof (e.g., response to therapy, drug resistance, and/or disease burden) characterized by certain molecular, pathological, histological, and/or clinical features. In some embodiments, the biomarker signature is a "gene signature". The term "gene signature" is used interchangeably with "gene expression signature" and refers to one or a combination of polynucleotides whose expression is an indicator, e.g., predictive, diagnostic, and/or prognostic. In some embodiments, the biomarker signature is a "protein signature." The term "protein signature" is used interchangeably with "protein expression signature" and refers to one or a combination of polypeptides whose expression is an indicator, e.g., predictive, diagnostic, and/or prognostic. A biomarker signature may comprise at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 or more biomarkers. In some embodiments, a biomarker signature comprises hundreds, or even thousands, of biomarkers or indications thereof. A biomarker signature can further comprise one or more controls or internal standards. In certain embodiments, a biomarker signature comprises at least one biomarker, or indication thereof, that serves as an internal standard. In other embodiments, a biomarker signature comprises an indication of one or more types of biomarkers. The term "indication" as used herein in this context merely refers to a situation where the biomarker signature contains symbols, data, abbreviations or other similar indicia for a biomarker, rather than the biomarker molecular entity itself. The term "biomarker signature" is also used herein to refer to a biomarker value or combination of at least two biomarker values, wherein individual biomarker values correspond to values of biomarkers that can be measured or functionalized from one or more subjects, which combination is characteristic of a discrete condition, stage of condition, subtype of condition or a prognosis for a discrete condition, stage of condition, subtype of condition. The term "signature biomarkers" is used to refer to a subset of the biomarkers that have been identified for use in a biomarker signature that can be used in performing a clinical assessment, such as to rule in or rule out a specific condition, different stages or severity of conditions, subtypes of different conditions or different prognoses. The number of signature biomarkers will vary, but is typically of the order of 16 or less (e.g., 16, 15, 14, 13, 12, 11, 10, 9, 8, 7, 6, 5, 4, 3, 2 or 1).

The term "clinical parameter", as used herein, refers any clinical measure of a disease state (e.g., joint inflammation) of a patient; for example, joint pain, joint stiffness, tenderness, swelling, warmth, patient global health assessment, erythrocyte sedimentation rate (ESR), C-reactive protein (CRP) levels, patient imaging (including any suitable imaging modality, such as x-ray (projectional radiographs), fluoroscopes, magnetic resonance imaging (MRI) instruments or nuclear magnetic resonance (NMR) scanners, x-ray computed tomography (CT) or computed axial tomography (CAT) scanners, positron emission tomography (PET) scanners, and ultrasonography (ultrasound) scanners) etc.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "composite score" refers to an aggregation of the obtained values for biomarkers measured in a sample from a subject optionally in combination with one or more patient clinical parameters. In some embodiments, the obtained biomarker values are normalized to provide a composite score for each subject tested. When used in the context of a risk categorization table and correlated to a stratified population grouping or cohort population grouping based on a range of composite scores in a risk categorization table, the "biomarker composite score" is used, at least in part, for example, by a machine learning system to determine the "risk score" for each subject tested wherein the numerical value (e.g., a multiplier, a percentage, etc.) indicating increased likelihood of having a type of joint inflammation disclosed herein for the stratified grouping becomes the "risk score".

As used herein, the term "correlates" or "correlates with" and like terms, refers to a statistical association between two or more things, such as events, characteristics, outcomes, numbers, data sets, etc., which may be referred to as "variables". It will be understood that the things may be of different types. Often the variables are expressed as numbers (e.g., measurements, values, likelihood, risk), wherein a positive correlation means that as one variable increases, the other also increases, and a negative correlation (also called anti-correlation) means that as one variable increases, the other variable decreases. In various embodiments, correlating a biomarker signature with the presence or absence of a condition (e.g., a condition selected from infectious joint inflammation and non-infectious joint inflammation) comprises determining the presence, absence, level or amount of at least one biomarker in a subject that has that condition; or in persons known to be free of that condition. In specific embodiments, a profile of IRS biomarker levels, absences or presences is correlated to a global probability or a particular outcome, using receiver operating characteristic (ROC) curves.

The term "cut-off value" as used herein is a level (or concentration) which may be an absolute level or a relative level, which is indicative of whether a subject has a particular disease or condition (e.g., infectious joint inflammation or non-infectious joint inflammation), or is at risk of having a particular disease or condition (e.g., infectious joint inflammation or non-infectious joint inflammation). Depending on the biomarker or combination of biomarkers, a subject is regarded as having the disease or condition or being at risk of having the disease or condition if either the level of the biomarker(s) detected and determined, respectively, is lower than the cut-off value, or the level of the biomarker(s) detected and determined, respectively, is higher than the cut-off value.

As used herein, the terms "detectably distinct" and "detectably different" are used interchangeably herein to refer to a signal that is distinguishable or separable by a physical property either by observation or by instrumentation. For example, a fluorophore is readily distinguishable either by spectral characteristics or by fluorescence intensity, lifetime, polarization or photo-bleaching rate from another fluorophore in a sample, as well as from additional materials that are optionally present. In certain embodiments, the terms "detectably distinct" and "detectably different" refer to a set of labels (such as dyes, suitably organic dyes) that can be detected and distinguished simultaneously.

As used herein, the phrase "developing a classifier" refers to using input variables to generate an algorithm or classifier capable of distinguishing between two or more states (e.g., infectious joint inflammation and non-infectious joint inflammation).

As used herein, the terms "diagnosis", "diagnosing" and the like are used interchangeably herein to encompass determining a likelihood that a subject will develop a condition, or the existence or nature of a condition in a subject. These terms also encompass determining a severity of disease or episode of disease, as well as in the context of rational therapy, in which the diagnosis guides therapy, including initial selection of therapy, modification of therapy (e.g., adjustment of dose or dosage regimen), and the like. By "likelihood" is meant a measure of whether a subject with particular measured or derived biomarker values actually has a condition (or not) based on a given mathematical model. An increased likelihood for example may be relative or absolute and may be expressed qualitatively or quantitatively. For instance, an increased likelihood may be determined simply by determining the subject's measured or derived biomarker values for at least two biomarkers and placing the subject in an "increased likelihood" category, based upon previous population studies. The term "likelihood" is also used interchangeably herein with the term "probability". The term "risk" relates to the possibility or probability of a particular event occurring at some point in the future. "Risk stratification" refers to an arraying of known clinical risk factors to allow physicians to classify patients into a low, moderate, high or highest risk of developing a particular disease or condition.

As used herein, a "diagnostic amount" of a biomarker refers to an amount of a biomarker in a subject's sample that is consistent with a diagnosis of infectious joint inflammation or non-infectious joint inflammation. A diagnostic amount can be either an absolute amount (e.g., ug/mL) or a relative amount (e.g., relative intensity of signals).

The term "differentially expressed" refers to differences in the quantity and/or the frequency of a biomarker present in a sample obtained from patients having, for example, infectious joint inflammation as compared to subjects with non-infectious joint inflammation. For example, a biomarker can be a polynucleotide or polypeptide which is present at an elevated level or at a decreased level in samples of patients with infectious joint inflammation compared to samples of subjects with non-infectious joint inflammation. Alternatively, a biomarker can be a polynucleotide or polypeptide which is detected at a higher frequency or at a lower frequency in samples of patients with infectious joint inflammation compared to samples of subjects with non-infectious joint inflammation. A biomarker can be differentially present in terms of quantity, frequency or both.

The term "discrimination performance" refers to numeric representation of the index including, for example, sensitivity, specificity, positive predictability, negative predictability or accuracy. The term "discrimination performance" may also refer to a value computed by the functions of the indexes. For example, sensitivity, specificity, positive predictive value, negative predictive value and accuracy may each be used as the discrimination performance, or alternatively, the sum of two or more indexes, e.g., the sum of sensitivity and specificity, the sum of sensitivity and positive predictive value, or the sum of negative predictive value and accuracy, may be used as the discrimination performance.

The term "expression product", as used herein, refers to any product produced during the process of gene expression including polypeptide products and polynucleotide products.

"Fluorophore" as used herein to refer to a moiety that absorbs light energy at a defined excitation wavelength and emits light energy at a different defined wavelength. Examples of fluorescence labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine 6G, Rhodamine Green, Rhodamine Red, Rhodol Green, 2',4',5', 7'-Tetra-bromosulfone-fluorescein, Tetramethyl-rhodamine (TMR), Carboxytetramethylrhodamine (TAMRA), Texas Red and Texas Red-X.

The term "gene", as used herein, refers to a stretch of nucleic acid that codes for a polypeptide or for an RNA chain that has a function. While it is the exon region of a gene that is transcribed to form mRNA, the term "gene" also includes regulatory regions such as promoters and enhancers that govern expression of the exon region.

As used herein, the term "higher" with reference to a biomarker measurement refers to a statistically significant and measurable difference in the level of a biomarker compared to the level of another biomarker or to a control level where the biomarker measurement is greater than the level of the other biomarker or the control level. The difference is suitably at least about 10%, or at least about 20%, or of at least about 30%, or of at least about 40%, or at least about 50%.

As used herein the terms "homology", "homologous" and the like refer to the level of similarity between two or more nucleic acid sequences in terms of percent of sequence identity. Generally, homologous sequences or sequences with homology refer to nucleic acid sequences that exhibit at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to one another. Alternatively, or in addition, homologs, homologous sequences or sequences with homology refer to nucleic acid sequences that hybridize under high stringency conditions to one another. High stringency conditions include and encompass from at least about 31% v/v to at least about 50% v/v formamide and from at least about 0.01 M to at least about 0.15 M salt for hybridization at 42° C., and at least about 0.01 M to at least about 0.15 M salt for washing at 42° C. High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5%

BSA, 1 mM EDTA, 40 mM NaHPO$_4$ (pH 7.2), 1% SDS for washing at a temperature in excess of 65° C.

The term "immobilized" means that a molecular species of interest is fixed to a solid support, suitably by covalent linkage. This covalent linkage can be achieved by different means depending on the molecular nature of the molecular species. Moreover, the molecular species may be also fixed on the solid support by electrostatic forces, hydrophobic or hydrophilic interactions or Van-der-Waals forces. The above described physicochemical interactions typically occur in interactions between molecules. In particular embodiments, all that is required is that the molecules (e.g., nucleic acids or polypeptides) remain immobilized or attached to a support under conditions in which it is intended to use the support, for example in applications requiring nucleic acid amplification and/or sequencing or in in antibody-binding assays. For example, oligonucleotides or primers are immobilized such that a 3' end is available for enzymatic extension and/or at least a portion of the sequence is capable of hybridizing to a complementary sequence. In some embodiments, immobilization can occur via hybridization to a surface attached primer, in which case the immobilized primer or oligonucleotide may be in the 3'-5' orientation. In other embodiments, immobilization can occur by means other than base-pairing hybridization, such as the covalent attachment.

As used herein, the term "increase" or "increased" with reference to a biomarker level refers to a statistically significant and measurable increase in the biomarker level compared to the level of another biomarker or to a control level. The increase is suitably an increase of at least about 10%, or an increase of at least about 20%, or an increase of at least about 30%, or an increase of at least about 40%, or an increase of at least about 50%.

The term "indicator", as used herein with reference to the indicator-determining methods of the present disclosure, refers to a result or representation of a result, including any information, number (e.g., biomarker value, functionalized biomarker value and/or composite score), ratio, signal, sign, mark, or note by which a skilled artisan can estimate and/or determine a likelihood or risk of whether or not a subject is suffering from a given disease or condition. In the case of the present disclosure, the "indicator" may optionally be used together with other clinical characteristics, to arrive at a diagnosis (that is, the occurrence or nonoccurrence) of infectious inflammation or non-infectious inflammation or a prognosis for infectious inflammation or non-infectious inflammation in a subject. That such an indicator is "determined" is not meant to imply that the indicator is 100% accurate. The skilled clinician may use the indicator together with other clinical indicia, including clinical parameters disclosed for example herein, to arrive at a diagnosis.

The term "inflammation" generally refers to a response in vasculated tissues to cellular or tissue injury usually caused by physical, chemical and/or biological agents, that is marked in the acute form by the classical sequences of pain, heat, redness, swelling, and loss of function (e.g., limb movement, weight bearing, etc.) and usually serves as a mechanism initiating the elimination, dilution or walling-off of noxious agents and/or of damaged tissue. Inflammation histologically involves a complex series of events, including dilation of the arterioles, capillaries, and venules with increased permeability and blood flow, exudation of fluids including plasma proteins, and leukocyte migration into the inflammatory focus. Inflammation may be caused by extraneous physical or chemical injury or by biological agents, e.g., viruses, bacteria, fungi, protozoan or metazoan parasite infections, as well as inflammation which is seemingly unprovoked, e.g., which occurs in the absence of demonstrable injury or infection, inflammation responses to self-antigens (auto-immune inflammation), inflammation responses to engrafted xenogeneic or allogeneic cells, tissues or organs, inflammation responses to allergens, etc. The term covers both acute inflammation and chronic inflammation. Also, the term includes both local or localized inflammation, as well as systemic inflammation, i.e., where one or more inflammatory processes are not confined to a particular tissue but occur generally in the endothelium and/or other organ systems. In some embodiments, the inflammation is acute inflammation, which is usually of sudden onset, marked by the classical signs of heat, redness, swelling, pain, and loss of function (e.g., limb movement, weight bearing, etc.), and in which vascular and exudative processes predominate; catarrhal inflammation, which is a form affecting mainly a mucous surface, marked by a copious discharge of mucus and epithelial debris; chronic inflammation, which is prolonged and persistent inflammation marked chiefly by new connective tissue formation; it may be a continuation of an acute form or a prolonged low-grade form; interstitial inflammation, which is inflammation affecting chiefly the stroma of an organ; traumatic inflammation, which is one that follows a wound or injury; ulcerative inflammation, in which necrosis on or near the surface leads to loss of tissue and creation of a local defect (e.g., ulcer). In accordance with the present disclosure, biomarkers are provided that are useful for stratifying inflammation into infectious inflammation and non-infectious inflammation. As used herein, "infectious inflammation" refers to inflammation that is associated with and/or is caused by the invasion and multiplication of microorganisms such as bacteria, viruses, fungi and parasites that are not normally present within the body. In contrast, "non-infectious inflammation" (also referred to herein as "sterile inflammation") refers to inflammation that is not associated with and/or is not caused by the invasion and multiplication of microorganisms such as bacteria, viruses, fungi and parasites that are not normally present within the body.

The term "joint pain" refers to a joint disorder or condition that involves inflammation and/or pain of one or more joints, suitably synovial joints. The term "joint pain", as used herein, encompasses a variety of types and subtypes of arthritis of various etiologies and causes, either known or unknown, including, but not limited to, infectious arthritis and non-infectious arthritis. Non-limiting examples of non-infectious arthritis include, arthritis resulting from joint surgery (e.g., joint repair or joint replacement), autoimmune arthropathies including for example rheumatoid arthritis, psoriatic arthritis and lupus-related arthritis, gouty arthritis, osteoarthritis, seronegative arthritis, reactive arthritis, Reiter's disease, calcium pyrophosphate disease, carcinomatous polyarthritis and chondrocalcinosis, or painful local tissues affected by bursitis, tenosynovitis, epicondylitis, synovitis and/or other disorders.

The term "label" is used herein in a broad sense to refer to an agent, substance, compound or molecule that is capable of providing a detectable signal, either directly or through interaction with one or more additional members of a signal producing system and that has been artificially added, linked or attached via chemical manipulation to a molecule. Labels can be visual, optical, photonic, electronic, acoustic, optoacoustic, by mass, electro-chemical, electro-optical, spectrometry, enzymatic, or otherwise chemically, biochemically hydrodynamically, electrically or physically detectable. Labels can be, for example tailed reporter, marker or adapter molecules. In specific embodiments, a molecule such as a nucleic acid molecule is labeled with a detectable molecule selected form the group consisting of radioisotopes, fluorescent compounds, bioluminescent compounds, chemiluminescent compounds, metal chelators or enzymes. Examples of labels include, but are not limited to, the following radioisotopes (e.g., $^3$H, $^{14}$C, $^{35}$S, $^{125}$I, $^{131}$I), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin, e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags).

As used herein, the term "lower" with reference to a biomarker measurement refers to a statistically significant and measurable difference in the level of a biomarker compared to the level of another biomarker or to a control level where the biomarker measurement is less than the level of the other biomarker or the control level. The difference is suitably at least about 10%, or at least about 20%, or of at least about 30%, or of at least about 40%, or at least about 50%.

The term "microarray" refers to an arrangement of array elements, e.g., probes (including primers), ligands, biomarker nucleic acid sequence or protein sequences on a substrate. The term "microarray" includes within its scope "high-density arrays" and "low-density arrays". In specific embodiments, the microarray refers to a substrate or collection of substrates or surfaces bearing a plurality of array elements (e.g., discrete regions having particular moieties, e.g., proteins (e.g., antibodies), nucleic acids (e.g., oligonucleotide probes), etc., immobilized thereto), where the array elements are present at a density of about 100 elements/cm$^2$ or more, about 1,000 elements/cm$^2$ or more, about 10,000 elements/cm$^2$ or more, or about 100,000 elements/cm$^2$ or more. In specific embodiments, a "high-density array" is one that comprises a plurality of array elements for detecting about 100 or more different biomarkers, about 1,000 or more different biomarkers, about 10,000 or more different biomarkers, or about 100,000 or more different biomarkers. In representative example of these embodiments, a "high-density array" is one that comprises a plurality of array elements for detecting biomarkers of about 100 or more different genes, of about 1,000 or more different genes, of about 10,000 or more different genes, or of about 100,000 or more different genes. Generally, the elements of a high-density array are not labeled. The term "low-density array" refers to a substrate or collection of substrates or surfaces bearing a plurality of array elements (e.g., discrete regions having particular moieties, e.g., proteins (e.g., antibodies), nucleic acids (e.g., oligonucleotide probes), etc., immobilized thereto), where the array elements are present at a density of about 100 elements/cm$^2$ or less, about 50 elements/cm$^2$ or less, about 20 elements/cm$^2$ or less, or about 10 elements/cm$^2$ or less. In specific embodiments, a "low-density array" is one that comprises a plurality of array elements for detecting about 100 or less different biomarkers, about 50 or less different biomarkers, about 20 or less different biomarkers (e.g., 20, 19, 18, 17, 16, 15, 14, 13, 12, 11, 10, 9, 8, 7, 6, 5, 4, 3, 2 or 1 distinct biomarker(s)), or about 10 or less different biomarkers (e.g., 10, 9, 8, 7, 6, 5, 4, 3, 2 or 1 distinct biomarker(s)). In representative example of these embodiments, a "low-density array" is one that comprises a plurality of array elements for detecting biomarkers of about 100 or less different genes, of about 50 or less different genes, of about 20 or less different genes (e.g., 20, 19, 18, 17, 16, 15, 14, 13, 12, 11, 10, 9, 8, 7, 6, 5, 4, 3, 2 or 1 distinct gene(s)), or of about 10 or less different genes (e.g., 10, 9, 8, 7, 6, 5, 4, 3, 2 or 1 distinct gene(s)). Generally, the elements of a low-density array are not labeled.

As referred to herein, the term "microbial" refers to a microscopic organism comprising either a single cell or a plurality of cells and encompasses, but is not limited to, prokaryotes such as bacteria, viruses and archaea; and forms of eukaryotes such as protozoan, yeast, fungi and algae.

As used herein, the term "nested" is used to describe a positional relationship between the annealing site of a primer of a primer pair and the annealing site of another primer of another primer pair. For example, a second primer may be nested by 1, 2, 3, 4, 5, 6, 7, 8, 9, 10, 20, 30, 40, 50, 60, 70, 80, 90, 100 or more nucleotides relative to a first primer, meaning that it binds to a site on the template strand that is frame-shifted by 1, 2, 3, 4, 5, 6, 7, 8, 9, 10, 20, 30, 40, 50, 60, 70, 80, 90, 100 or more nucleotides.

As used herein, the term "nested primers" or "nested oligonucleotide primers" refers to primers that anneal to a target sequence in an area that is inside the annealing boundaries of another pair of primers, which are typically a primer pair that is used to start a nucleic acid amplification ("also known as "starting primers"). Because the nested primers anneal to the target sequence inside the annealing boundaries of the starting primers, the predominant amplified product of the starting primers is necessarily a longer sequence, than that defined by the annealing boundaries of the nested primers. The amplified product of the nested primers is an amplified segment of the target sequence that cannot, therefore, anneal with the starting primers. Advantages to the use of nested primers include the large degree of specificity, as well as the fact that a smaller sample portion may be used and yet obtain specific and efficient amplification.

As used herein, the term "normalization" and its derivatives, when used in conjunction with measurement of biomarkers across samples and time, refer to mathematical methods, including but not limited to multiple of the median (MoM), standard deviation normalization, sigmoidal normalization, etc., where the intention is that these normalized values allow the comparison of corresponding normalized values from different datasets in a way that eliminates or minimizes differences and gross influences.

The term "nucleic acid" or "polynucleotide" as used herein includes RNA, mRNA, miRNA, CRNA, cDNA, mtDNA, or DNA. The term typically refers to a polymeric form of nucleotides of at least 10 bases in length, either ribonucleotides or deoxynucleotides or a modified form of either type of nucleotide. The term includes single and double stranded forms of DNA or RNA.

By "obtained" is meant to come into possession. Samples so obtained include, for example, nucleic acid extracts or polypeptide extracts isolated or derived from a particular source. For instance, the extract may be isolated directly from a biological fluid or tissue of a subject.

As used herein, the term "panel" refers to specific combination of biomarkers used to determine an indicator for assessing a likelihood that a type of inflammation is present or absent in a joint of a subject. The term "panel" may also refer to an assay comprising a set of biomarkers used for such a determination. This term can also refer to a profile or index of expression patterns of one or more biomarkers described herein. The number of biomarkers useful for a biomarker panel is based on the sensitivity and specificity value for the particular combination of biomarker values.

As used herein, the term "positive response" means that the result of a treatment regimen includes some clinically significant benefit, such as the prevention, or reduction of severity, of symptoms, or a slowing of the progression of the condition. By contrast, the term "negative response" means that a treatment regimen provides no clinically significant benefit, such as the prevention, or reduction of severity, of symptoms, or increases the rate of progression of the condition.

"Protein", "polypeptide" and "peptide" are used interchangeably herein to refer to a polymer of amino acid residues and to variants and synthetic analogues of the same.

By "primer" is meant an oligonucleotide which, when paired with a strand of DNA, is capable of initiating the synthesis of a primer extension product in the presence of a suitable polymerizing agent. The primer is preferably single-stranded for maximum efficiency in amplification but can alternatively be double-stranded. A primer must be sufficiently long to prime the synthesis of extension products in the presence of the polymerization agent. The length of the primer depends on many factors, including application, temperature to be employed, template reaction conditions, other reagents, and source of primers. For example, depending on the complexity of the target sequence, the primer may be at least about 5, 6, 7, 8, 9, 10, 11, 12, 13, 14, 15, 16, 17, 18, 19, 20, 21, 22, 23, 24, 25, 26, 27, 28, 29, 30, 35, 40, 50, 75, 100, 150, 200, 300, 400, 500, to one base shorter in length than the template sequence at the 3' end of the primer to allow extension of a nucleic acid chain, though the 5' end of the primer may extend in length beyond the 3' end of the template sequence. In certain embodiments, primers can be large polynucleotides, such as from about 35 nucleotides to several kilobases or more. Primers can be selected to be "substantially complementary" to the sequence on the template to which it is designed to hybridize and serve as a site for the initiation of synthesis. By "substantially complementary", it is meant that the primer is sufficiently complementary to hybridize with a target polynucleotide. Desirably, the primer contains no mismatches with the template to which it is designed to hybridize but this is not essential. For example, non-complementary nucleotide residues can be attached to the 5' end of the primer, with the remainder of the primer sequence being complementary to the template. Alternatively, non-complementary nucleotide residues or a stretch of non-complementary nucleotide residues can be interspersed into a primer, provided that the primer sequence has sufficient complementarity with the sequence of the template to hybridize therewith and thereby form a template for synthesis of the extension product of the primer.

As used herein, the term "probe" refers to a molecule that binds to a specific sequence or sub-sequence or other moiety of another molecule. Unless otherwise indicated, the term "probe" typically refers to a nucleic acid probe that binds to another nucleic acid, also referred to herein as a "target polynucleotide", through complementary base pairing. Probes can bind target polynucleotides lacking complete sequence complementarity with the probe, depending on the stringency of the hybridization conditions. Probes can be labeled directly or indirectly and include primers within their scope.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. The skilled artisan will understand that the term "prognosis" refers to an increased probability that a certain course or outcome will occur; that is, that a course or outcome is more likely to occur in a subject exhibiting a given condition, when compared to those individuals not exhibiting the condition.

The term "proximal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. In general, the term indicates an element is located relatively near to the reference point than another element.

As used herein, the term "quencher" includes any moiety that in close proximity to a donor fluorophore, takes up emission energy generated by the donor fluorophore and either dissipates the energy as heat or emits light of a longer wavelength than the emission wavelength of the donor fluorophore. In the latter case, the quencher is considered to be an acceptor fluorophore. The quenching moiety can act via proximal (i.e., collisional) quenching or by Forster or fluorescence resonance energy transfer ("FRET"). Quenching by FRET is generally used in TaqMan™ probes while proximal quenching is used in molecular beacon and Scorpion™ type probes. Suitable quenchers are selected based on the fluorescence spectrum of the particular fluorophore. Useful quenchers include, for example, the Black Hole™ quenchers BHQ-1, BHQ-2, and BHQ-3 (Biosearch Technologies, Inc.), and the ATTO-series of quenchers (ATTO 540Q, ATTO 580Q, and ATTO 612Q; Atto-Tec GmbH).

As used herein, a "reaction vessel" refers to any container, chamber, device, or assembly, in which a reaction can occur in accordance with the present disclosure. In some embodiments, a reaction vessel may be a microtube, for example, but not limited to, a 0.2 mL or a 0.5 mL reaction tube such as a MicroAmp™ Optical tube (Applied Biosystems™, Thermo Fisher Scientific) or a micro-centrifuge tube, or other containers of the sort in common practice in molecular biology laboratories. In some embodiments, a reaction vessel may be a well in a microtiter plate (e.g., 96-well plate, 384-well plate) such as a TaqMan™ Array plate (Applied Biosystems™; Thermo Fisher Scientific), a spot on a glass slide, a well in an Applied Biosystems™ TaqMan™ Array Card or Plate (Thermo Fisher Scientific) or a through-hole of an Applied Biosystems™ TaqMan™ OpenArray™ plate (Thermo Fisher Scientific). For example, a plurality of reaction vessels may reside on the same support. In some embodiments, lab-on-a-chip-like devices, available for example from Caliper, Fluidigm and Life Technologies Corp., including the Ion 316™ and Ion 318™ Chip, may serve as reaction vessels in the disclosed methods and devices. In some embodiments, various microfluidic approaches may be employed. It will be recognized that a variety of reaction vessels are available in the art and fall within the scope of the present disclosure.

As used herein, the term "reduce" or "reduced" with reference to a biomarker level refers to a statistically significant and measurable reduction in the biomarker level compared to the level of another biomarker or to a control level. The reduction is suitably a reduction of at least about 10%, or a reduction of at least about 20%, or a reduction of at least about 30%, or a reduction of at least about 40%, or a reduction of at least about 50%.

The term "rule-out" and its grammatical equivalents refer to a diagnostic test with high sensitivity that optionally coupled with a clinical assessment indicates a lower likelihood of a particular condition (e.g., infectious inflammation or non-infectious inflammation). Accordingly, the term "ruling out" as used herein is meant that the subject is selected not to receive a treatment protocol or regimen for treating a specified condition (e.g., infectious inflammation or non-infectious inflammation).

The term "sample" as used herein includes any biological specimen that may be extracted, untreated, treated, diluted or concentrated from a subject. Such biological samples may include, without limitation, biological fluids such as whole blood, serum, red blood cells, white blood cells, plasma, joint exudate, synovial fluid, cell lysates, cellular secretion products and inflammation fluid. Samples may include tissue samples (e.g., synovial tissue samples) and biopsies, tissue homogenates and the like. Exemplary samples for use in accordance with the present disclosure, include fluid samples, particularly fluid samples from, or adjacent to, a synovial joint. Advantageous samples may include ones comprising any one or more biomarkers as taught herein in detectable quantities. Suitably, the sample is readily obtainable by minimally invasive methods, allowing the removal or isolation of the sample from the subject. In some embodiments, the sample may contain blood such as peripheral blood, or a fraction or extract thereof. The sample may comprise blood cells such as mature, immature or developing leukocytes, including lymphocytes, polymorphonuclear leukocytes, neutrophils, monocytes, reticulocytes, basophils, coelomocytes, hemocytes, eosinophils, megakaryocytes, macrophages, dendritic cells natural killer cells, or fraction of such cells (e.g., a nucleic acid or protein fraction). In specific embodiments, the sample comprises synovial fluid.

The term "solid support" as used herein refers to a solid inert surface or body to which a molecular species, such as a nucleic acid and polypeptides can be immobilized. Non-limiting examples of solid supports include glass surfaces, plastic surfaces, latex, dextran, polystyrene surfaces, polypropylene surfaces, polyacrylamide gels, gold surfaces, and silicon wafers. In some embodiments, the solid supports are in the form of membranes, chips or particles. For example, the solid support may be a glass surface (e.g., a planar surface of a flow cell channel). In some embodiments, the solid support may comprise an inert substrate or matrix which has been "functionalized", such as by applying a layer or coating of an intermediate material comprising reactive groups which permit covalent attachment to molecules such as polynucleotides. By way of non-limiting example, such supports can include polyacrylamide hydrogels supported on an inert substrate such as glass. The molecules (e.g., polynucleotides) can be directly covalently attached to the intermediate material (e.g., a hydrogel) but the intermediate material can itself be non-covalently attached to the substrate or matrix (e.g., a glass substrate). The support can include a plurality of particles or beads each having a different attached molecular species.

The terms "subject", "individual" and "patient" are used interchangeably herein to refer to an animal subject, particularly a vertebrate subject, and even more particularly a mammalian subject. Suitable vertebrate animals that fall within the scope of the present disclosure include, but are not restricted to, any member of the phylum Chordata, subphylum vertebrata including primates, rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (snakes, frogs, lizards, etc.), and fish. A preferred subject is a primate (e.g., a human, ape, monkey, chimpanzee). The subject suitably has joint pain and/or at least one (e.g., 1, 2, 3, 4, 5 or more) clinical sign of inflammation.

The term "synovial fluid" refers to the liquid produced by the synovial membranes of a joint. Synovial fluid lubricates and facilitates movement of the joint. The term "synovium" refers to the thin layer of connective tissue with a free smooth surface that lines the capsule of a joint. The "synovial membrane" refers to the connective-tissue membrane that lines the cavity of a synovial joint and produces the synovial fluid. Synovial fluid typically comprises nucleated cells such as leukocytes, non-limiting examples of which include neutrophils, lymphocytes (e.g., T and/or B lymphocytes), monocytes, and macrophages.

The term "synovial joint" as used herein refers to a joint between two bones that includes an articular capsule forming a synovial cavity typically containing synovial fluid (although it is contemplated that a joint having an articular capsule absent synovial fluid (e.g., where the fluid may have been removed surgically) is still considered a synovial joint). The term "intra-articular" or "intra-articular space" refers to the space (whether or not containing synovial fluid) confined by the articular capsule where two surfaces of adjacent bones articulate with one another. The term "synovial joint" encompasses joints lined with articular cartilage or joint that were previously lined with articular cartilage, wherein the cartilage has been degraded through pathological processes conditions (e.g., rheumatoid arthritis, or infection) or artificially removed (e.g., by surgery). A synovial joint may be native or artificial (i.e., prosthetic).

As used herein the terms "synovial tissue" and "synovium" refer to the thin, loose vascular connective tissue that makes up, more specifically lines the interior of all joints and also the sheaths surrounding tendons such as in the hands and feet. Synovial tissue contains synovial cells (synovicytes), which secrete a viscous liquid called synovial fluid; this liquid contains proteins and hyaluronic acid and serves as a lubricant and nutrient for the joint cartilage surfaces.

As used herein, the term "treatment regimen" refers to prophylactic and/or therapeutic (i.e., after onset of a specified condition) treatments, unless the context specifically indicates otherwise. The term "treatment regimen" encompasses natural substances and pharmaceutical agents (i.e., "drugs") as well as any other treatment regimen including but not limited to dietary treatments, physical therapy or exercise regimens, surgical interventions, and combinations thereof.

It will be appreciated that the terms used herein and associated definitions are used for the purpose of explanation only and are not intended to be limiting.

2. Joint Inflammation Biomarkers and their Use for Stratifying Joint Inflammation into Infectious Joint Inflammation or Non-Infectious Joint Inflammation Disclosed herein are methods, compositions, apparatuses, devices and kits for aiding in distinguishing subjects with infectious joint inflammation from subjects with non-infectious joint inflammation. These methods, compositions, apparatuses, devices and kits are useful for early detection of infectious joint inflammation or non-infectious joint inflammation, thus allowing better treatment decisions for subjects with symptoms of joint inflammation (e.g., joint pain) that stem at least in part from microbial infection or non-infectious causes.

The present inventors have determined that certain biomarkers are commonly, specifically and differentially expressed in samples obtained from sites of joint inflammation. The results presented herein provide clear evidence that specific biomarkers can be used, optionally in combination with clinical parameters, to differentiate between infectious joint inflammation and non-infectious joint inflammation with a remarkable degree of accuracy. Additionally, it has been determined that the disclosed biomarkers can exclude joint inflammation with a NPV greater than 95% at a prevalence of infectious joint inflammation set at 33%, and may thus be useful for triaging treatment decisions for subjects with joint inflammation.

Based on these findings, the biomarkers disclosed herein are proposed to have utility in laboratory and point-of-care diagnostics that allow for rapid screening for infectious joint inflammation or non-infectious joint inflammation, or for ruling out infectious joint inflammation, which may result in significant cost savings to the medical system, as subjects with joint inflammation can be categorized with increased accuracy and exposed to management procedures and therapeutic agents that are suitable for treating a particular type or source of joint inflammation.

Biomarkers that can be used in the practice of the methods, compositions, apparatuses, devices and kits disclosed herein include expression products of genes (also referred to herein as ("joint inflammation host response genes"), including but not limited to: ACO2, AP3M1, API5, AQP9, ATG4B, ATIC, C5orf15, CANX, CDKN1A, CISH, CLIC4, CSF2RB, CSF3R, CSNK1D, CWC27, CXCL8, DTNBP1, DUSP1, DUSP5, EIF2S1, EMP1, ERP44, ETV6, FCGR3B, FFAR2, FPR1, FYB1, GADD45B, GBP1, GRINA, H3-3B, HCK, HLA-E, HNRNPAB, IARS2, IER3, IL1B, IL1RN, IMMT, IPO8, IRF2, KCTD2, KCTD3, KLF13, KLHL12, LARP4, LILRB3, LMNA, LRPPRC, LYN, MCL1, MLLT6, MOCS3, MRPL20, MRPL37, MXD1, MYO1F, NAGA, NAMPT, NFKBIA, NINJ1, NUP58, OSM, PARP14, PDE4B, PI3, PIK3AP1, PIK3R5, PIP4K2B, PKN1, PLAUR, PLEC, PLEK, PLXDC2, POLG2, POLR2G, PPIF, PPIL2, PPP5C, PRPF19, PSMC3, RILPL2, RNASEL, RNF26, SEC24B, SEMA4D, SLC26A6, SNIP1, SNRPF, SP1, SP2, STARD7, STX11, SUSD6, TBK1, TNFAIP2, TNFAIP3, TNFRSF1B, TTYH3, TWF2, VPS4B, VPS51, WIPF2, ZFP36 and ZZEF1, which are differentially expressed in the joints of patients with infectious inflammation as compared to the joints of patients with non-infectious inflammation. Differential expression of one or more of these "joint inflammation biomarkers" is useful therefore for providing an indicator that aids in the diagnosis of, and distinguishing between, joint inflammations that is associated with a microbial infection and non-infectious joint inflammatory conditions, such as caused by traumatic injury, surgery, autoimmune disease, gout or painful local tissues proximal to a joint affected by bursitis, tenosynovitis, epicondylitis, synovitis and/or other disorders.

In one aspect, methods are disclosed for determining an indicator used in assessing a likelihood that a type of inflammation is present or absent in a joint of a subject, wherein the type of inflammation is selected from infectious inflammation and non-infectious inflammation. These methods general comprise, consist or consist essentially of: (1) determining a biomarker value for at least one biomarker (e.g., 1 to 100 biomarkers, and all integer biomarkers in between) in a sample obtained from a site of inflammation associated with the joint, wherein a respective biomarker
value is indicative of a level of a corresponding biomarker
in the sample, wherein the at least one biomarker is selected
from a first panel of biomarkers comprising, consisting or
consisting essentially of ACO2, AP3M1, ATG4B, C5orf15, CANX, CDKN1A, CSNK1D, CWC27, CXCL8, DTNBP1,
DUSP1, EIF2S1, EMP1, ERP44, FCGR3B, FFAR2, FPR1,
FYB1, GBP1, H3-3B, HNRNPAB, IARS2, IPO8, IRF2,
KCTD2, KCTD3, KLF13, KLHL12, LARP4, LMNA,
MCL1, MLLT6, MOCS3, MRPL20, MRPL37, MXD1, MYO1F, NAGA, NAMPT, NINJ1, NUP58, PARP14,
PIK3AP1, PIK3R5, PIP4K2B, PKN1, PLEC, PLXDC2,
POLG2, POLR2G, PPIL2, PPP5C, PRPF19, PSMC3,
RILPL2, RNASEL, RNF26, SEC24B, SLC26A6, SNIP1,
SNRPF, SP1, SP2, STX11, SUSD6, TBK1, TNFRSF1B,
TTYH3, TWF2, VPS4B, VPS51, WIPF2 and ZZEF1; and
(2) determining the indicator using the biomarker value(s).
In accordance with the present disclosure, the indicator-
determining methods advantageously distinguish between a
likelihood that infectious inflammation is present or absent
in a joint of a subject and a likelihood that non-infectious
inflammation is present or absent in the joint of the subject.
For example, the indicator determined using the biomarker
value(s) may indicate a likelihood that infectious inflamma-
tion is present in the joint of the subject and a likelihood that
non-infectious inflammation is absent in the joint of the
subject. Alternatively, the determined indicator may indicate
a likelihood that infectious inflammation is absent in the
joint of the subject and a likelihood that non-infectious
inflammation is present in the joint of the subject.

In some embodiments, biomarker values are obtained for
a plurality of biomarkers, wherein the plurality of biomark-
ers is selected from the first panel of biomarkers and
optionally from a second panel of biomarkers comprising
API5, AQP9, ATIC, CISH, CLIC4, CSF2RB, CSF3R,
DUSP5, ETV6, GADD45B, GRINA, HCK, HLA-E, IER3,
IL1B, IL1RN, IMMT, LILRB3, LRPPRC, LYN, NFKBIA,
OSM, PDE4B, PI3, PLAUR, PLEK, PPIF, SEMA4D,
STARD7, TNFAIP2, TNFAIP3 and ZFP36.

Biomarker panels disclosed herein typically comprise at least 2 biomarkers and up to 30 biomarkers, including any
number of biomarkers in between, such as 3, 4, 5, 6, 7, 8, 9,
10, 11, 12, 13, 14, 15, 16, 17, 18, 19, 20, 21, 22, 23, 24, 25,
26, 27, 28, 29, or 30 biomarkers. In certain embodiments, a
biomarker panel comprises at least 2, or least 3, or at least
4, or at least 5, or at least 6, or at least 7, or at least 8, or at
least 9, or at least 10, or at least 11, or at least 12, or at least
13, or at least 14, or at least 15 or at least 16 or more
biomarkers. In some embodiments, a biomarker panel com-
prises up to 4, or up to 5, or up to 6, or up to 7, or up to 8, or up to 9, or up to 10, or up to 11, or up to 12, or up to 13,
or up to 14, or up to 15, or up to 16 biomarkers.

Biomarker values that are indicative of the levels of
biomarkers in a patient sample may be obtained by any
suitable means known in the art. The sample may obtained
from any accessible site of joint inflammation. The joint may
be a synovial joint, a fibrous joint or a cartilaginous joint. In
specific embodiments, the joint is a synovial joint, repre-
sentative examples of which include a knee joint, wrist joint,
shoulder joint, hip joint, elbow joint or ankle joint. The
sample may comprise synovial fluid, lymph fluid, joint
exudate, joint transudate, or combination thereof.

Measurement of the expression level of a biomarker in the
sample can be direct or indirect. For example, the abundance
levels of RNAs or proteins can be directly quantitated.
Alternatively, the amount of a biomarker can be determined
indirectly by measuring abundance levels of cDNAs, amplified or messenger RNAs or DNAs, or by measuring quan-
tities or activities of RNAs, proteins, or other molecules
(e.g., metabolites) that are indicative of the expression level
of the biomarker. The methods for measuring biomarkers in
a sample have many applications. For example, one or more
biomarkers can be measured to aid in the diagnosis of
infectious joint inflammation or non-infectious joint inflam-
mation, to determine the appropriate treatment for a subject,
to monitor responses in a subject to treatment, or to identify
therapeutic compounds that modulate expression of the
biomarkers in vivo or in vitro.

2.1 Polynucleotide Assays

In some embodiments, the expression levels of joint
inflammation biomarkers are determined by measuring bio-
marker polynucleotide levels. The levels of transcripts of
specific biomarker genes can be determined from the
amount of mRNA, or polynucleotides derived therefrom,
present in a biological sample. Polynucleotides can be
detected and quantitated by a variety of methods including,
but not limited to, microarray analysis, polymerase chain
reaction (PCR), reverse transcriptase polymerase chain reac-
tion (RT-PCR), Northern blot, and serial analysis of gene
expression (SAGE).

In illustrative polynucleotide assays, nucleic acid is iso-
lated from cells contained in the biological sample according
to standard methodologies (Sambrook, et al., "MOLECU-
LAR CLONING. A LABORATORY MANUAL", Cold
Spring Harbor Press, 1989; and Ausubel et al., "CURRENT
PROTOCOLS IN MOLECULAR BIOLOGY", John Wiley
& Sons Inc., 1994-1998). The nucleic acid is typically
fractionated (e.g., poly A+ RNA) or whole cell RNA. Where
RNA is used as the subject of detection, it may be desired to
convert the RNA to a complementary DNA. In some
embodiments, the nucleic acid is amplified by a template-
dependent nucleic acid amplification technique. Numerous
template dependent processes are available to amplify the
joint inflammation biomarker sequences present in a given
template sample. An exemplary nucleic acid amplification
technique is PCR, which is described in detail in U.S. Pat.
Nos. 4,683,195, 4,683,202 and 4,800,159, Ausubel et al.
(supra), and in Innis et al., ("PCR Protocols", Academic
Press, Inc., San Diego Calif., 1990). Briefly, in PCR, two
primer sequences are prepared that are complementary to
regions on opposite complementary strands of the biomarker
sequence. An excess of deoxynucleotide triphosphates is
added to a reaction mixture along with a DNA polymerase,
e.g., Taq polymerase. If a cognate joint inflammation bio-
marker sequence is present in a sample, the primers will bind
to the biomarker and the polymerase will cause the primers
to be extended along the biomarker sequence by adding on
nucleotides. By raising and lowering the temperature of the
reaction mixture, the extended primers will dissociate from
the biomarker to form reaction products, excess primers will
bind to the biomarker and to the reaction products and the
process is repeated. A reverse transcriptase PCR amplifica-
tion procedure may be performed in order to quantify the
amount of mRNA amplified. Methods of reverse transcrib-
ing RNA into cDNA are well known and described in
Sambrook et al., 1989, supra. Alternative methods for
reverse transcription utilize thermostable, RNA-dependent
DNA polymerases. These methods are described in WO
90/07641. Polymerase chain reaction methodologies are
well known in the art. In specific embodiments in which
whole cell RNA is used, cDNA synthesis using whole cell
RNA as a sample produces whole cell cDNA.

In certain advantageous embodiments, the template-de-
pendent amplification involves quantification of transcripts in real-time. For example, RNA or DNA may be quantified using the Real-Time PCR (RT-PCR) technique (Higuchi, 1992, et al., Biotechnology 10:413-417). By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundance of the specific mRNA from which the target sequence was derived can be determined for the respective tissues or cells. This direct proportionality between the concentration of the PCR products and the relative mRNA abundance is only true in the linear range of the PCR reaction. The final concentration of the target DNA in the plateau portion of the curve is determined by the availability of reagents in the reaction mix and is independent of the original concentration of target DNA. In some embodiments, multiplexed, tandem PCR (MT-PCR) is employed, which uses a two-step process for gene expression profiling from small quantities of RNA or DNA, as described for example in US Pat. Appl. Pub. No. 20070190540. In the first step, RNA is converted into cDNA and amplified using multiplexed gene specific primers. In the second step each individual gene is quantitated by RT-PCR. Real-time PCR is typically performed using any PCR instrumentation available in the art. Typically, instrumentation used in real-time PCR data collection and analysis comprises a thermal cycler, optics for fluorescence excitation and emission collection, and optionally a computer and data acquisition and analysis software.

In some embodiments of RT-PCR assays, a TaqMan™ probe is used for quantitating nucleic acid. Such assays may use energy transfer ("ET"), such as fluorescence resonance energy transfer ("FRET"), to detect and quantitate the synthesized PCR product. Typically, the TaqMan™ probe comprises a fluorescent label (e.g., a fluorescent dye) coupled to one end (e.g., the 5'-end) and a quencher molecule is coupled to the other end (e.g., the 3'-end), such that the fluorescent label and the quencher are in close proximity, allowing the quencher to suppress the fluorescence signal of the dye via FRET. When a polymerase replicates the chimeric amplicon template to which the fluorescent labeled probe is bound, the 5'-nuclease of the polymerase cleaves the probe, decoupling the fluorescent label and the quencher so that label signal (such as fluorescence) is detected. Signal (such as fluorescence) increases with each PCR cycle proportionally to the amount of probe that is cleaved.

TaqMan™ probes typically comprise a region of contiguous nucleotides having a sequence that is identically present in or complementary to a region of a joint inflammation biomarker polynucleotide such that the probe is specifically hybridizable to the resulting PCR amplicon. In some embodiments, the probe comprises a region of at least 6 contiguous nucleotides having a sequence that is fully complementary to or identically present in a region of a target joint inflammation biomarker polynucleotide, such as comprising a region of at least 8 contiguous nucleotides, at least 10 contiguous nucleotides, at least 12 contiguous nucleotides, at least 14 contiguous nucleotides, or at least 16 contiguous nucleotides having a sequence that is complementary to or identically present in a region of a target joint inflammation biomarker polynucleotide to be detected and/or quantitated.

In addition to the TaqMan™ assays, other real-time PCR chemistries useful for detecting PCR products in the methods presented herein include, but are not limited to, Molecular Beacons, Scorpion probes and intercalating dyes, such as SYBR Green, EvaGreen, thiazole orange, YO-PRO, TO-PRO, etc. For example, Molecular Beacons, like TaqMan™ probes, use FRET to detect and quantitate a PCR product via a probe having a fluorescent label (e.g., a fluorescent dye) and a quencher attached at the ends of the probe. Unlike TaqMan™ probes, however, Molecular Beacons remain intact during the PCR cycles. Molecular Beacon probes form a stem-loop structure when free in solution, thereby allowing the fluorescent label and quencher to be in close enough proximity to cause fluorescence quenching. When the Molecular Beacon hybridizes to a target, the stem-loop structure is abolished so that the fluorescent label and the quencher become separated in space and the fluorescent label fluoresces. Molecular Beacons are available, e.g., from Gene Link™ (see, www<dot>genelink<dot>com).

In some embodiments, Scorpion probes can be used as both sequence-specific primers and for PCR product detection and quantitation. Like Molecular Beacons, Scorpion probes form a stem-loop structure when not hybridized to a target nucleic acid. However, unlike Molecular Beacons, a Scorpion probe achieves both sequence-specific priming and PCR product detection. A fluorescent label (e.g., a fluorescent dye molecule) is attached to the 5'-end of the Scorpion probe, and a quencher is attached to the 3'-end. The 3' portion of the probe is complementary to the extension product of the PCR primer, and this complementary portion is linked to the 5'-end of the probe by a non-amplifiable moiety. After the Scorpion primer is extended, the target-specific sequence of the probe binds to its complement within the extended amplicon, thus opening up the stem-loop structure and allowing the fluorescent label on the 5'-end to fluoresce and generate a signal. Scorpion probes are available from, e.g., Premier Biosoft International (see www<dot>premierbiosoft<dot>com/tech_notes/ Scorpion<dot>html).

In some embodiments, labels that can be used on the FRET probes include colorimetric and fluorescent dyes such as Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Examples of dye/quencher pairs (i.e., donor/acceptor pairs) include, but are not limited to, fluorescein/tetramethylrhodamine; IAEDANS/fluorescein; EDANS/dabcyl; fluorescein/fluorescein; BODIPY FL/BODIPY FL; fluorescein/QSY 7 or QSY 9 dyes. When the donor and acceptor are the same, FRET may be detected, in some embodiments, by fluorescence depolarization. Certain specific examples of dye/quencher pairs (i.e., donor/acceptor pairs) include, but are not limited to, Alexa Fluor 350/Alexa Fluor488; Alexa Fluor 488/Alexa Fluor 546; Alexa Fluor 488/Alexa Fluor 555; Alexa Fluor 488/Alexa Fluor 568; Alexa Fluor 488/Alexa Fluor 594; Alexa Fluor 488/Alexa Fluor 647; Alexa Fluor 546/Alexa Fluor 568; Alexa Fluor 546/Alexa Fluor 594; Alexa Fluor 546/Alexa Fluor 647; Alexa Fluor 555/Alexa Fluor 594; Alexa Fluor 555/Alexa Fluor 647; Alexa Fluor 568/Alexa Fluor 647; Alexa Fluor 594/Alexa Fluor 647; Alexa Fluor 350/QSY35; Alexa Fluor 350/dabcyl; Alexa Fluor 488/QSY 35; Alexa Fluor 488/dabcyl; Alexa Fluor 488/QSY 7 or QSY 9; Alexa Fluor 555/QSY 7 or QSY9; Alexa Fluor 568/QSY 7 or QSY 9; Alexa Fluor 568/QSY 21; Alexa Fluor 594/QSY 21; and Alexa Fluor 647/QSY 21. In some embodiments, the same quencher may be used for multiple dyes, for example, a broad spectrum quencher, such as an Iowa Black™ quencher (Integrated DNA Technologies, Coralville, Iowa) or a Black Hole Quencher™ (BHQ™; Sigma-Aldrich, St. Louis, Mo.).

In some embodiments, for example, in a multiplex reaction in which two or more moieties (such as amplicons) are detected simultaneously, each probe comprises a detectably different dye such that the dyes may be distinguished when detected simultaneously in the same reaction. One skilled in the art can select a set of detectably different dyes for use in a multiplex reaction. In some embodiments, multiple target joint inflammation biomarker polynucleotides are detected and/or quantitated in a single multiplex reaction. In some embodiments, each probe that is targeted to a different joint inflammation biomarker polynucleotide is spectrally distinguishable when released from the probe. Thus, each target joint inflammation biomarker polynucleotide is detected by a unique fluorescence signal.

Specific examples of fluorescently labeled ribonucleotides useful in the preparation of real-time PCR probes for use in some embodiments of the methods described herein are available from Molecular Probes (Invitrogen), and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences (GE Healthcare), such as Cy3-UTP and Cy5-UTP.

Examples of fluorescently labeled deoxyribonucleotides useful in the preparation of real-time PCR probes for use in the methods described herein include Dinitrophenyl (DNP)-1'-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP. Fluorescently labeled nucleotides are commercially available and can be purchased from, e.g., Invitrogen.

In some embodiments, SAGE analysis is used to determine RNA abundances in a cell sample (see, e.g., Velculescu et al., 1995, Science 270:484-7; Carulli, et al., 1998, Journal of Cellular Biochemistry Supplements 30/31:286-96). SAGE analysis does not require a special device for detection, and is one of the preferable analytical methods for simultaneously detecting the expression of a large number of transcription products. First, poly $A^+$ RNA is extracted from cells. Next, the RNA is converted into cDNA using a biotinylated oligo (dT) primer, and treated with a four-base recognizing restriction enzyme (Anchoring Enzyme: AE) resulting in AE-treated fragments containing a biotin group at their 3' terminus. Next, the AE-treated fragments are incubated with streptavidin for binding. The bound cDNA is divided into two fractions, and each fraction is then linked to a different double-stranded oligonucleotide adapter (linker) A or B. These linkers are composed of: (1) a protruding single strand portion having a sequence complementary to the sequence of the protruding portion formed by the action of the anchoring enzyme, (2) a 5' nucleotide recognizing sequence of the IIS-type restriction enzyme (cleaves at a predetermined location no more than 20 bp away from the recognition site) serving as a tagging enzyme (TE), and (3) an additional sequence of sufficient length for constructing a PCR-specific primer. The linker-linked cDNA is cleaved using the tagging enzyme, and only the linker-linked cDNA sequence portion remains, which is present in the form of a short-strand sequence tag. Next, pools of short-strand sequence tags from the two different types of linkers are linked to each other, followed by PCR amplification using primers specific to linkers A and B. As a result, the amplification product is obtained as a mixture comprising myriad sequences of two adjacent sequence tags (ditags) bound to linkers A and B. The amplification product is treated with the anchoring enzyme, and the free ditag portions are linked into strands in a standard linkage reaction. The amplification product is then cloned. Determination of the clone's nucleotide sequence can be used to obtain a read-out of consecutive ditags of constant length. The presence of mRNA corresponding to each tag can then be identified from the nucleotide sequence of the clone and information on the sequence tags.

In certain embodiments, target nucleic acids are quantified using blotting techniques, which are well known to those of skill in the art. Southern blotting involves the use of DNA as a target, whereas Northern blotting involves the use of RNA as a target. Each provides different types of information, although cDNA blotting is analogous, in many aspects, to blotting or RNA species. Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter. Subsequently, the blotted target is incubated with a probe (usually labeled) under conditions that promote denaturation and rehybridization. Because the probe is designed to base pair with the target, the probe will bind a portion of the target sequence under renaturing conditions. Unbound probe is then removed, and detection is accomplished as described above. Following detection/quantification, one may compare the results seen in a given subject with a control reaction or a statistically significant reference group or population of control subjects as defined herein. In this way, it is possible to correlate the amount of joint inflammation biomarker nucleic acid detected with the progression or severity of the disease.

Also contemplated are microarray based technologies such as those described by Hacia et al. (1996, Nature Genetics 14:441-447) and Shoemaker et al. (1996, Nature Genetics 14:450-456). Briefly, these techniques involve quantitative methods for analyzing large numbers of genes rapidly and accurately. By tagging genes with oligonucleotides or using fixed nucleic acid probe arrays, one can employ microarray technology to segregate target molecules as high-density or low density arrays and screen these molecules on the basis of hybridization. See also Pease et al. (1994, Proc. Natl. Acad. Sci. U.S.A. 91: 5022-5026); Fodor et al. (1991, Science 251: 767-773). Briefly, nucleic acid probes to joint inflammation biomarker polynucleotides are made and attached to microarrays to be used in the detection methods disclosed herein. The nucleic acid probes attached to the microarray are designed to be substantially complementary to specific expressed joint inflammation biomarker nucleic acids, i.e., the target sequence (either the target sequence of the sample or to other probe sequences, for example in sandwich assays), such that hybridization of the target sequence and the probes of the present disclosure occur. This complementarity need not be perfect; there may be any number of base pair mismatches, which will interfere with hybridization between the target sequence and the nucleic acid probes. However, if the number of mismatches is so great that no hybridization can occur under even the least stringent of hybridization conditions, the sequence is not a complementary target sequence. In certain embodiments, more than one probe per sequence is used, with either overlapping probes or probes to different sections of the target being used. That is, two, three, four or more probes, with three being desirable, are used to build in a redundancy for a particular target. The probes can be overlapping (i.e. have some sequence in common), or separate.

In an illustrative microarray analysis, oligonucleotide probes on the microarray are exposed to or contacted with a nucleic acid sample suspected of containing one or more joint inflammation biomarker polynucleotides under conditions favoring specific hybridization. Sample extracts of DNA or RNA, either single or double-stranded, may be prepared from fluid suspensions of biological materials, or by grinding biological materials, or following a cell lysis step which includes, but is not limited to, lysis effected by treatment with SDS (or other detergents), osmotic shock, guanidinium isothiocyanate and lysozyme. Suitable DNA, which may be used in the method of the present disclosure, includes cDNA. Such DNA may be prepared by any one of a number of commonly used protocols as for example described in Ausubel, et al., 1994, supra, and Sambrook, et al., 1989, supra.

Suitable RNA, which may be used in the detection methods disclosed herein, includes messenger RNA, complementary RNA transcribed from DNA (CRNA) or genomic or subgenomic RNA. Such RNA may be prepared using standard protocols as for example described in the relevant sections of Ausubel, et al. 1994, supra and Sambrook, et al. 1989, supra).

cDNA may be fragmented, for example, by sonication or by treatment with restriction endonucleases. Suitably, cDNA is fragmented such that resultant DNA fragments are of a length greater than the length of the immobilized oligonucleotide probe(s) but small enough to allow rapid access thereto under suitable hybridization conditions. Alternatively, fragments of cDNA may be selected and amplified using a suitable nucleotide amplification technique, as described for example above, involving appropriate random or specific primers.

Usually the target joint inflammation biomarker polynucleotides are detectably labeled so that their hybridization to individual probes can be determined. The target polynucleotides are typically detectably labeled with a reporter molecule illustrative examples of which include chromogens, catalysts, enzymes, fluorochromes, chemiluminescent molecules, bioluminescent molecules, lanthanide ions (e.g., Eu34), a radioisotope and a direct visual label. In the case of a direct visual label, use may be made of a colloidal metallic or non-metallic particle, a dye particle, an enzyme or a substrate, an organic polymer, a latex particle, a liposome, or other vesicle containing a signal producing substance and the like. Illustrative labels of this type include large colloids, for example, metal colloids such as those from gold, selenium, silver, tin and titanium oxide. In some embodiments in which an enzyme is used as a direct visual label, biotinylated bases are incorporated into a target polynucleotide.

The hybrid-forming step can be performed under suitable conditions for hybridizing oligonucleotide probes to test nucleic acid including DNA or RNA. In this regard, reference may be made, for example, to NUCLEIC ACID HYBRIDIZATION, A PRACTICAL APPROACH (Homes and Higgins, eds.) (IRL press, Washington D.C., 1985). In general, whether hybridization takes place is influenced by the length of the oligonucleotide probe and the polynucleotide sequence under test, the pH, the temperature, the concentration of mono- and divalent cations, the proportion of G and C nucleotides in the hybrid-forming region, the viscosity of the medium and the possible presence of denaturants. Such variables also influence the time required for hybridization. The preferred conditions will therefore depend upon the particular application. Such empirical conditions, however, can be routinely determined without undue experimentation.

After the hybrid-forming step, the probes are washed to remove any unbound nucleic acid with a hybridization buffer. This washing step leaves only bound target polynucleotides. The probes are then examined to identify which probes have hybridized to a target polynucleotide.

The hybridization reactions are then detected to determine which of the probes has hybridized to a corresponding target sequence. Depending on the nature of the reporter molecule associated with a target polynucleotide, a signal may be instrumentally detected by irradiating a fluorescent label with light and detecting fluorescence in a fluorimeter; by providing for an enzyme system to produce a dye which could be detected using a spectrophotometer; or detection of a dye particle or a colored colloidal metallic or non-metallic particle using a reflectometer; in the case of using a radioactive label or chemiluminescent molecule employing a radiation counter or autoradiography. Accordingly, a detection means may be adapted to detect or scan light associated with the label which light may include fluorescent, luminescent, focused beam or laser light. In such a case, a charge couple device (CCD) or a photocell can be used to scan for emission of light from a probe: target polynucleotide hybrid from each location in the microarray and record the data directly in a digital computer. In some cases, electronic detection of the signal may not be necessary. For example, with enzymatically generated color spots associated with nucleic acid array format, visual examination of the array will allow interpretation of the pattern on the array. In the case of a nucleic acid array, the detection means is suitably interfaced with pattern recognition software to convert the pattern of signals from the array into a plain language genetic profile. In certain embodiments, oligonucleotide probes specific for different joint inflammation biomarker polynucleotides are in the form of a nucleic acid array and detection of a signal generated from a reporter molecule on the array is performed using a 'microarray reader'. A detection system that can be used by a microarray reader is described for example by Pirrung et al. (U.S. Pat. No. 5,143,854). The microarray reader will typically also incorporate some signal processing to determine whether the signal at a particular array position or feature is a true positive or maybe a spurious signal. Exemplary microarray readers are described for example by Fodor et al. (U.S. Pat. No. 5,925,525). Alternatively, when the array is made using a mixture of individually addressable kinds of labeled microbeads, the reaction may be detected using flow cytometry.

In certain embodiments, the joint inflammation biomarker is a target RNA (e.g., mRNA) or a DNA copy of the target RNA whose level or abundance is measured using at least one nucleic acid probe that hybridizes under at least high stringency conditions to the target RNA or to the DNA copy, wherein the nucleic acid probe comprises at least 15 (e.g., 15, 16, 17, 18, 19, 20, 21, 22, 23, 24, 25, 26, 27, 28, 29, 30, or more) contiguous nucleotides of joint inflammation biomarker polynucleotide. In some embodiments, the measured level or abundance of the target RNA or its DNA copy is normalized to the level or abundance of a reference RNA or a DNA copy of the reference RNA. Suitably, the nucleic acid probe is immobilized on a solid or semi-solid support. In illustrative examples of this type, the nucleic acid probe forms part of a spatial array of nucleic acid probes. In some embodiments, the level of nucleic acid probe that is bound to the target RNA or to the DNA copy is measured by hybridization (e.g., using a nucleic acid array). In other embodiments, the level of nucleic acid probe that is bound to the target RNA or to the DNA copy is measured by nucleic acid amplification (e.g., using a polymerase chain reaction (PCR)). In still other embodiments, the level of nucleic acid probe that is bound to the target RNA or to the DNA copy is measured by nuclease protection assay.

Sequencing technologies including DNA sequencing and RNA sequencing, such as Sanger sequencing, pyrosequencing, sequencing by ligation, massively parallel sequencing, also called "Next-generation sequencing" (NGS), whole transcriptome shotgun sequence (WTSS) (also referred to as "RNAseq"), nanopore sequencing, nanostring sequencing and other high-throughput sequencing approaches with or without sequence amplification of the target can also be used to detect or quantify the presence of joint inflammation biomarker polynucleotides in a sample. Sequence-based methods can provide further information regarding alternative splicing and sequence variation in previously identified genes. Sequencing technologies include a number of steps that are grouped broadly as template preparation, sequencing, detection and data analysis. Current methods for template preparation involve randomly breaking genomic DNA into smaller sizes from which each fragment is immobilized to a support. The immobilization of spatially separated fragment allows thousands to billions of sequencing reaction to be performed simultaneously. A sequencing step may use any of a variety of methods that are commonly known in the art. One specific example of a sequencing step uses the addition of nucleotides to the complementary strand to provide the DNA sequence. The detection steps range from measuring bioluminescent signal of a synthesized fragment to four-color imaging of single molecule. In some embodiments in which NGS is used to detect or quantify the presence of joint inflammation nucleic acid biomarker in a sample, the methods are suitably selected from semiconductor sequencing (Ion Torrent; Personal Genome Machine); Helicos True Single Molecule Sequencing (tSMS) (Harris et al. 2008, Science 320:106-109); 454 sequencing (Roche) (Margulies et al. 2005, Nature, 437, 376-380); SOLID technology (Applied Biosystems); SOLEXA sequencing (Illumina); single molecule, real-time (SMRT™) technology of Pacific Biosciences; nanopore sequencing (Soni and Meller, 2007. Clin Chem 53:1996-2001); DNA nanoball sequencing; sequencing using technology from Dover Systems (Polonator), and technologies that do not require amplification or otherwise transform native DNA prior to sequencing (e.g., Pacific Biosciences and Helicos), such as nanopore-based strategies (e.g., Oxford Nanopore, Genia Technologies, and Nabsys).

In non-limiting embodiments of the polynucleotide assays, compositions are prepared for use in the indicator-determining methods disclosed herein. These compositions may comprise a mixture of a DNA polymerase (e.g., a thermostable DNA polymerase), synovial fluid leukocyte cDNA from a subject with joint pain and/or at least one clinical sign of inflammation (e.g., acute inflammation) in, or proximal to, the joint, wherein the synovial fluid leukocyte cDNA comprises at least one cDNA selected from a joint inflammation biomarkers disclosed herein, and wherein the composition further comprises for each cDNA at least one oligonucleotide primer or probe that hybridizes to that cDNA. In some of the same or other embodiments, the compositions comprise for respective cDNA two oligonucleotide primers that hybridize to opposite complementary strands of the cDNA. In some of the same or other embodiments, the compositions comprise for a respective cDNA an oligonucleotide probe that hybridizes to the cDNA or a polynucleotide corresponding thereto (e.g., a polynucleotide product resulting nucleic acid amplification of the cDNA). The oligonucleotide probe may comprise a heterologous label (e.g., a fluorescent label). In embodiments in which the oligonucleotide probe comprises a heterologous label, the labeled oligonucleotide probe may comprise a fluorophore. In representative examples of this type, the labeled oligonucleotide probe further comprises a quencher. In certain embodiments, different labeled oligonucleotide probes are included in the composition for hybridizing to different CDNAs, wherein individual oligonucleotide probes comprise detectably distinct labels (e.g. different fluorophores), or at least a subset of oligonucleotide probes comprises the same label (e.g. same fluorophore). In some embodiments, the compositions comprise for each of at least 2, 4, 5, 6, 7, or 8 of the cDNAs at least one oligonucleotide primer and/or probe that hybridizes to the cDNA. In other embodiments, the compositions comprise for each of up to 2, 4, 5, 6, 7, or 8 of the cDNAs at least one oligonucleotide primer and/or probe that hybridizes to the cDNA. Individual cDNAs and their corresponding oligonucleotide primer(s) and/or probe(s) may be present in separate reaction vessels or in the same reaction vessel.

Biological samples (e.g., synovial fluid leukocyte samples) obtained from a site of joint inflammation or joint-related inflammation typically comprise biomarkers that are expressed at the same or similar levels between patients with infectious joint inflammation and those with non-infectious joint inflammation. These biomarkers can be used to define a common biomarker profile or signature that is characteristic of, and shared between, such subjects regardless of the infectious status of their joint inflammation. Representative biomarkers of this type include but are not limited to ADCY7, CSRNP2, DNAJC4, FBXO28, GNAI2, HNRNPU, NEK8, PBLD, PTMA, RABL2B, RHOT2, RNF25, SRRM2, TMBIM6, TMED4, TPM3, UCK1, ZNF787, as shown in FIG. 1. Accordingly, a cDNA sample prepared from synovial fluid leukocyte MRNA obtained from a site of joint inflammation will generally comprise a first joint inflammation cDNA, a second joint inflammation cDNA and a third joint inflammation cDNA wherein the first cDNA is present in the cDNA sample at a higher level than the second cDNA and wherein the second cDNA is present in the cDNA sample at a higher level than the third cDNA, wherein the first cDNA is selected from any one of SRRM2, HNRNPU, PTMA, TMBIM6, GNAI2 and TPM3, wherein the second cDNA is selected from any one of RHOT2, TMED4, UCK1, FBXO28, DNAJC4 and RNF25, and wherein the third cDNA is selected from any one of PBLD, NEK8, ADCY7, ZNF787, RABL2B and CSRNP2.

2.2 Polypeptide Assays

In other embodiments, joint inflammation biomarker protein levels are assayed using protein-based assays known in the art. For example, antibody-based techniques may be employed including, for example, immunoassays, such as the enzyme-linked immunosorbent assay (ELISA) and the radioimmunoassay (RIA). In non-limiting examples of this type, protein-capture arrays that permit simultaneous detection and/or quantification of a large number of proteins are employed. For example, low-density protein arrays on filter membranes, such as the universal protein array system (Ge, 2000 Nucleic Acids Res. 28 (2):e3) allow imaging of arrayed antigens using standard ELISA techniques and a scanning charge-coupled device (CCD) detector. Immuno-sensor arrays have also been developed that enable the simultaneous detection of clinical analytes. It is now possible using protein arrays, to profile protein expression in bodily fluids, such as in sera of healthy or diseased subjects, as well as in subjects pre- and post-drug treatment.

Exemplary protein capture arrays include arrays comprising spatially addressed antigen-binding molecules, commonly referred to as antibody arrays, which can facilitate extensive parallel analysis of numerous proteins defining a proteome or subproteome. Antibody arrays have been shown to have the required properties of specificity and acceptable background, and some are available commercially (e.g., BD Biosciences, Clonetech, Bio-Rad and Sigma). Various methods for the preparation of antibody arrays have been reported (see, e.g., Lopez et al., 2003 J. Chromatogram. B 787:19-27; Cahill, 2000 Trends in Biotechnology 7:47-51; U.S. Pat. App. Pub. 2002/0055186; U.S. Pat. App. Pub. 2003/0003599; PCT publication WO 03/062444; PCT publication WO 03/077851; PCT publication WO 02/59601; PCT publication WO 02/39120; PCT publication WO 01/79849; PCT publication WO 99/39210). The antigen-binding molecules of such arrays may recognize at least a subset of proteins expressed by a cell or population of cells, illustrative examples of which include growth factor receptors, hormone receptors, neurotransmitter receptors, catecholamine receptors, amino acid derivative receptors, cytokine receptors, extracellular matrix receptors, antibodies, lectins, cytokines, serpins, proteases, kinases, phosphatases, ras-like GTPases, hydrolases, steroid hormone receptors, transcription factors, heat-shock transcription factors, DNA-binding proteins, zinc-finger proteins, leucine-zipper proteins, homeodomain proteins, intracellular signal transduction modulators and effectors, apoptosis-related factors, DNA synthesis factors, DNA repair factors, DNA recombination factors and cell-surface antigens.

Individual spatially distinct protein-capture agents are typically attached to a support surface, which is generally planar or contoured. Common physical supports include glass slides, silicon, microwells, nitrocellulose or PVDF membranes, and magnetic and other microbeads.

Particles in suspension can also be used as the basis of arrays, providing they are coded for identification; systems include color coding for microbeads (e.g., available from Luminex, Bio-Rad and Nanomics Biosystems) and semiconductor nanocrystals (e.g., QDots™, available from Quantum Dots), and barcoding for beads (UltraPlex™, available from Smartbeads) and multimetal microrods (Nanobarcodes™ particles, available from Surromed). Beads can also be assembled into planar arrays on semiconductor chips (e.g., available from LEAPS technology and BioArray Solutions). Where particles are used, individual protein-capture agents are typically attached to an individual particle to provide the spatial definition or separation of the array. The particles may then be assayed separately, but in parallel, in a compartmentalized way, for example in the wells of a microtiter plate or in separate test tubes.

In operation, a protein sample, which is optionally fragmented to form peptide fragments (see, e.g., U.S. Pat. App. Pub. 2002/0055186), is delivered to a protein-capture array under conditions suitable for protein or peptide binding, and the array is washed to remove unbound or non-specifically bound components of the sample from the array. Next, the presence or amount of protein or peptide bound to each feature of the array is detected using a suitable detection system. The amount of protein bound to a feature of the array may be determined relative to the amount of a second protein bound to a second feature of the array. In certain embodiments, the amount of the second protein in the sample is already known or known to be invariant.

In specific embodiments, the joint inflammation biomarker is a target polypeptide whose level is measured using at least one antigen-binding molecule that binds specifically to the target polypeptide. In these embodiments, the measured level of the target polypeptide is normalized to the level of a reference polypeptide. Suitably, the antigen-binding molecule is immobilized on a solid or semi-solid support. In illustrative examples of this type, the antigen-binding molecule forms part of a spatial array of antigen-binding molecule. In some embodiments, the level of antigen-binding molecule that is bound to the target polypeptide is measured by immunoassay (e.g., using an ELISA).

2.3 Biomarker Panels

The present inventors have determined that certain joint inflammation biomarkers have strong discrimination performance when combined with one or more other joint inflammation biomarkers for determining an indicator that is useful for assessing a likelihood that a type of inflammation (i.e., infectious or non-infectious inflammation) is present or absent in a joint of a subject. In advantageous embodiments, specific combinations of joint inflammation biomarkers have been identified that can be used to determine an indicator. Accordingly, in representative examples of this type, an indicator is determined that correlates to a combination of joint inflammation biomarkers, which can be used in assessing a likelihood that infectious joint inflammation or non-infectious joint inflammation is present or absent in a subject.

In these examples, the indicator-determining methods suitably include determining biomarker values for a plurality of biomarkers, wherein each biomarker value is a value measured for at least one corresponding joint inflammation biomarker of the subject and is indicative of a concentration or level of the joint inflammation biomarker in a sample obtained from the subject. The biomarker values are typically used to determine a combined biomarker value (also referred to herein as a "composite score") on which at least in part an indicator for assessing a likelihood that a type of inflammation disclosed herein is present or absent in a joint of a subject is determined.

In some embodiments, biomarker values are determined for a first joint inflammation biomarker and a second joint inflammation biomarker, wherein the first biomarker is selected from a first set of biomarkers that are expressed at a higher level in infectious inflammation than in non-infectious inflammation, and wherein the second biomarker is selected from a second set of biomarkers that are expressed at a lower level in infectious inflammation than in non-infectious inflammation, and/or from a third set of biomarkers that improve the discrimination performance of the first biomarker, wherein the first set of biomarkers comprises, consists or consists essentially of AQP9, C5orf15, CANX, CDKN1A, CISH, CLIC4, CSF2RB, CSF3R, CXCL8, DTNBP1, DUSP1, DUSP5, ERP44, ETV6, FCGR3B, FFAR2, FPR1, FYB1, GADD45B, GBP1, GRINA, H3-3B, HCK, HLA-E, IRF2, LILRB3, LYN, MCL1, MLLT6, MXD1, NAMPT, NFKBIA, NINJ1, NUP58, PARP14, PDE4B, PI3, PIK3AP1, PIK3R5, PLAUR, PLEK, RILPL2, RNASEL, SEMA4D, SP2, STX11, SUSD6, TBK1, TNFAIP2, TNFAIP3, TNFRSF1B and WIPF2, wherein the second set of biomarkers comprises, consists or consists essentially of ACO2, AP3M1, API5, ATIC, CWC27, EIF2S1, EMP1, HNRNPAB, IARS2, KLF13, LARP4, LMNA, LRPPRC, MOCS3, MRPL20, MRPL37, NAGA, PIP4K2B, PKN1, PLEC, PLXDC2, PPIL2, PPP5C, PRPF19, RNF26, STARD7, TTYH3, TWF2, VPS51 and ZZEF1, and wherein the third set of biomarkers comprises, consists or consists essentially of CSNK1D, MYO1F and POLR2G.

In representative examples of this type, the first and second biomarkers are selected from TABLE A:

TABLE A

| First Biomarker | Second Biomarker |
| --- | --- |
| MXD1 | MYO1F |
| SP2 | KLF13 |
| DUSP5 | PLEC |
| CSF2RB | MYO1F |
| DUSP5 | PRPF19 |
| ERP44 | AP3M1 |
| NFKBIA | MOCS3 |
| CLIC4 | PLEC |
| DUSP5 | VPS51 |
| DUSP5 | STARD7 |
| ERP44 | CWC27 |
| NFKBIA | POLR2G |
| DUSP5 | HNRNPAB |
| DUSP5 | ACO2 |
| DUSP5 | PPP5C |
| DUSP5 | ATIC |
| DUSP5 | PIP4K2B |
| DUSP5 | TTYH3 |
| DUSP5 | MRPL37 |
| NFKBIA | RNF26 |

In other embodiments, biomarker values are determined for a first joint inflammation biomarker, a second joint inflammation biomarker, a third joint inflammation biomarker and optionally a fourth joint inflammation biomarker, wherein the first and second biomarkers are selected from a first set of biomarkers that are expressed at a higher level in infectious inflammation than in non-infectious inflammation, and wherein the third and optional fourth biomarkers are selected from a second set of biomarkers that are expressed at a lower level in infectious inflammation than in non-infectious inflammation, and/or a third set of biomarkers that improve the discrimination performance of the first and/or second biomarkers, wherein the first set of biomarkers comprises, consists or consists essentially of AQP9, C5orf15, CANX, CDKN1A, CISH, CLIC4, CSF2RB, CSF3R, CXCL8, DTNBP1, DUSP1, DUSP5, ERP44, ETV6, FCGR3B, FFAR2, FPR1, FYB1, GADD45B, GBP1, GRINA, H3-3B, HCK, HLA-E, IRF2, LILRB3, LYN, MCL1, MLLT6, MXD1, NAMPT, NFKBIA, NINJ1, NUP58, PARP14, PDE4B, PI3, PIK3AP1, PIK3R5, PLAUR, PLEK, RILPL2, RNASEL, SEMA4D, SNIP1, SP1, SP2, STX11, SUSD6, TBK1, TNFAIP2, TNFAIP3, TNFRSF1B and WIPF2, wherein the second set of biomarkers comprises, consists or consists essentially of ACO2, AP3M1, API5, ATIC, CWC27, EIF2S1, EMP1, IMMT, KLF13, LARP4, LMNA, LRPPRC, MOCS3, MRPL20, MRPL37, NAGA, PIP4K2B, PKN1, PLEC, PLXDC2, PPIL2, PPP5C, PRPF19, PSMC3, RNF26, SNRPF, STARD7, TTYH3, TWF2 and VPS51 and wherein the third set of biomarkers comprises, consists or consists essentially of ATG4B, CSNK1D, IPO8, KCTD2, MYO1F, POLG2, POLR2G and ZZEF1.

In non-limiting examples of this type, the first and second biomarkers, and one or both of the third and fourth biomarkers are selected from TABLE B:

TABLE B

| First Biomarker | Second Biomarker | Third Biomarker | Fourth Biomarker |
| --- | --- | --- | --- |
| CLIC4 | CSF2RB | POLR2G | — |
| CLIC4 | CSF2RB | MYO1F | PPP5C |
| CLIC4 | NUP58 | EIF2S1 | — |
| CLIC4 | DUSP5 | PLEC | PSMC3 |
| CLIC4 | NUP58 | API5 | — |
| CLIC4 | DUSP5 | PLEC | RNF26 |
| CLIC4 | CSF2RB | CSNK1D | PPP5C |
| CLIC4 | NUP58 | AP3M1 | — |
| CLIC4 | MXD1 | KCTD2 | |
| CLIC4 | MXD1 | MYO1F | PPP5C |
| CLIC4 | DUSP5 | PLEC | SNRPF |
| CLIC4 | CSF2RB | KCTD2 | |
| CLIC4 | CSF2RB | IPO8 | |
| CLIC4 | DUSP5 | EIF2S1 | PLEC |
| CLIC4 | DUSP5 | PLEC | PPP5C |
| CLIC4 | CSF2RB | POLR2G | PPP5C |
| CLIC4 | TNFRSF1B | CSNK1D | PPP5C |
| CLIC4 | CSF2RB | KCTD2 | PPP5C |
| CLIC4 | RILPL2 | MOCS3 | PPP5C |
| CLIC4 | NUP58 | POLR2G | TTYH3 |

In still other embodiments, biomarker values are determined for a first joint inflammation biomarker, a second joint inflammation biomarker, a third joint inflammation biomarker, optionally a fourth joint inflammation biomarker, a fifth joint inflammation biomarker, a sixth joint inflammation biomarker and optionally one or both of a seventh joint inflammation biomarker and an eighth joint inflammation biomarker, wherein the first biomarker, second biomarker, third biomarker and optional fourth biomarker are selected from a first set of biomarkers that are expressed at a higher level in infectious inflammation than in non-infectious inflammation, and wherein the fifth biomarker, sixth biomarker and optional seventh and eighth biomarkers are selected from a second set of biomarkers that are expressed at a lower level in infectious inflammation than in non-infectious inflammation, and/or from a third set of biomarkers that improve the discrimination performance of the first biomarker, second biomarker, third biomarker and optional fourth biomarker, wherein the first set of biomarkers comprises, consists or consists essentially of AQP9, C5orf15, CANX, CDKN1A, CISH, CLIC4, CSF2RB, CSF3R, CXCL8, DTNBP1, DUSP1, DUSP5, EMP1, ERP44, ETV6, FCGR3B, FFAR2, FPR1, FYB1, GADD45B, GRINA, H3-3B, HCK, HLA-E, IER3, IL1B, IL1RN, IRF2, LILRB3, LMNA, LYN, MCL1, MLLT6, MXD1, NAMPT, NFKBIA, NINJ1, NUP58, OSM, PDE4B, PI3, PIK3AP1, PLAUR, PLEK, PPIF, RILPL2, RNASEL, SEMA4D, SNIP1, SP1, SP2, STX11, SUSD6, TNFAIP2, TNFAIP3, TNFRSF1B, WIPF2 and ZFP36 wherein the second set of biomarkers comprises, consists or consists essentially of ACO2, AP3M1, API5, EIF2S1, IMMT, KCTD3, KLF13, MOCS3, MRPL20, PKN1, PLEC, PPP5C, PSMC3, RNF26, SNRPF, STARD7 and TTYH3, and wherein the third set of biomarkers comprises, consists or consists essentially of ATG4B, CSNK1D, IPO8, KLHL12, MYO1F, POLG2, POLR2G, SEC24B, SLC26A6, VPS4B and ZZEF1.

In illustrative examples of this type, the first biomarker, second biomarker, third biomarker, optional fourth biomarker, fifth biomarker, sixth biomarker and optional seventh and eighth biomarkers are selected from TABLE C:

joint inflammation and in subjects with non-infectious joint inflammation. Representative biomarker combinations of this type include 3, 4, 5, 6, 7, 8 or 9 biomarkers.

The detection methods disclosed herein may further comprise applying a function to biomarker values to yield at least one functionalized biomarker value and determining the indicator using the at least one functionalized biomarker value. The function may include at least one of: (a) multiplying biomarker values; (b) dividing biomarker values; (c) adding biomarker values; (d) subtracting biomarker values; (e) a weighted sum of biomarker values; (f) a log sum of biomarker values; (g) a geometric mean of biomarker values; and (h) a sigmoidal function of biomarker values.

In various embodiments employing panels of joint inflammation biomarkers, the detection methods may further comprise combining the biomarker values to provide a composite score and determining the indicator using the composite score. Biomarker values may be combined by a combining function including, but not limited to, adding, multiplying, subtracting, and/or dividing biomarker values. Biomarker values may be combined by applying the combining function to individual biomarker values of different biomarkers.

TABLE C

| First Biomarker | Second Biomarker | Third Biomarker | Fourth Biomarker | Fifth Biomarker | Sixth Biomarker | Seventh Biomarker | Eighth Biomarker |
|---|---|---|---|---|---|---|---|
| CLIC4 | CSF2RB | NUP58 | | IPO8 | POLR2G | | |
| CLIC4 | CSF2RB | NUP58 | | POLR2G | PPP5C | VPS4B | |
| CLIC4 | DUSP5 | SP2 | | PKN1 | PLEC | PPP5C | RNF26 |
| CLIC4 | NUP58 | SP2 | | PKN1 | PLEC | PPP5C | VPS4B |
| CLIC4 | CSF2RB | DUSP5 | | PLEC | POLR2G | PSMC3 | |
| CLIC4 | CSF2RB | DUSP5 | RNASEL | ATG4B | KLF13 | POLR2G | |
| CLIC4 | CSF2RB | NUP58 | SNIP1 | POLR2G | PPIL2 | VPS4B | |
| CLIC4 | CSF2RB | DUSP5 | | POLR2G | PPP5C | RNF26 | |
| CLIC4 | NUP58 | SP2 | | PKN1 | PLEC | PPP5C | SEC24B |
| CLIC4 | CSF2RB | DUSP5 | | MYO1F | PLEC | PPP5C | RNF26 |
| CLIC4 | PPIF | SP2 | | PKN1 | PLEC | PPP5C | SLC26A6 |
| CLIC4 | CSF2RB | NUP58 | | KLHL12 | POLR2G | PPP5C | |
| CLIC4 | DUSP5 | SP2 | | PKN1 | PLEC | PPP5C | PSMC3 |
| CLIC4 | CSF2RB | DUSP5 | | CSNK1D | PPP5C | PPP5C | RNF26 |
| CLIC4 | CSF2RB | DUSP5 | | AP3M1 | PPP5C | RNF26 | |
| CLIC4 | CSF2RB | DUSP5 | | PLXDC2 | PPP5C | RNF26 | |
| CLIC4 | DUSP5 | SP2 | | KCTD3 | PKN1 | PLEC | PPP5C |
| CLIC4 | NUP58 | SP2 | | PKN1 | PLEC | POLR2G | |
| CLIC4 | DUSP5 | NUP58 | | PLEC | PPP5C | RNF26 | SEC24B |
| CLIC4 | DUSP5 | SP2 | | KLF13 | PLEC | PPP5C | RNF26 |

In any of the examples described above:
CSF2RB may be substituted with ETV6, FFAR2, FYB1, HCK, HLA-E, IRF2, LILRB3, PDE4B, SEMA4D, STX11 or TNFAIP2;
DUSP5 may be substituted with CDKN1A, CISH or MLLT6;
NUP58 may be substituted with CXCL8;
MXD1 may be substituted with AQP9, CSF3R, DUSP1, FCGR3B, FPR1, H3-3B, LYN, MCL1 or NAMPT;
NFKBIA may be substituted with GADD45B, GRINA, NINJ1, PI3, PIK3AP1, PLAUR, PLEK or TNFAIP3;
PLEC may be substituted EMP1 or LMNA; and
PPIF may be substituted with IER3, IL1B, IL1RN, OSM or ZFP36.

Figure 2:
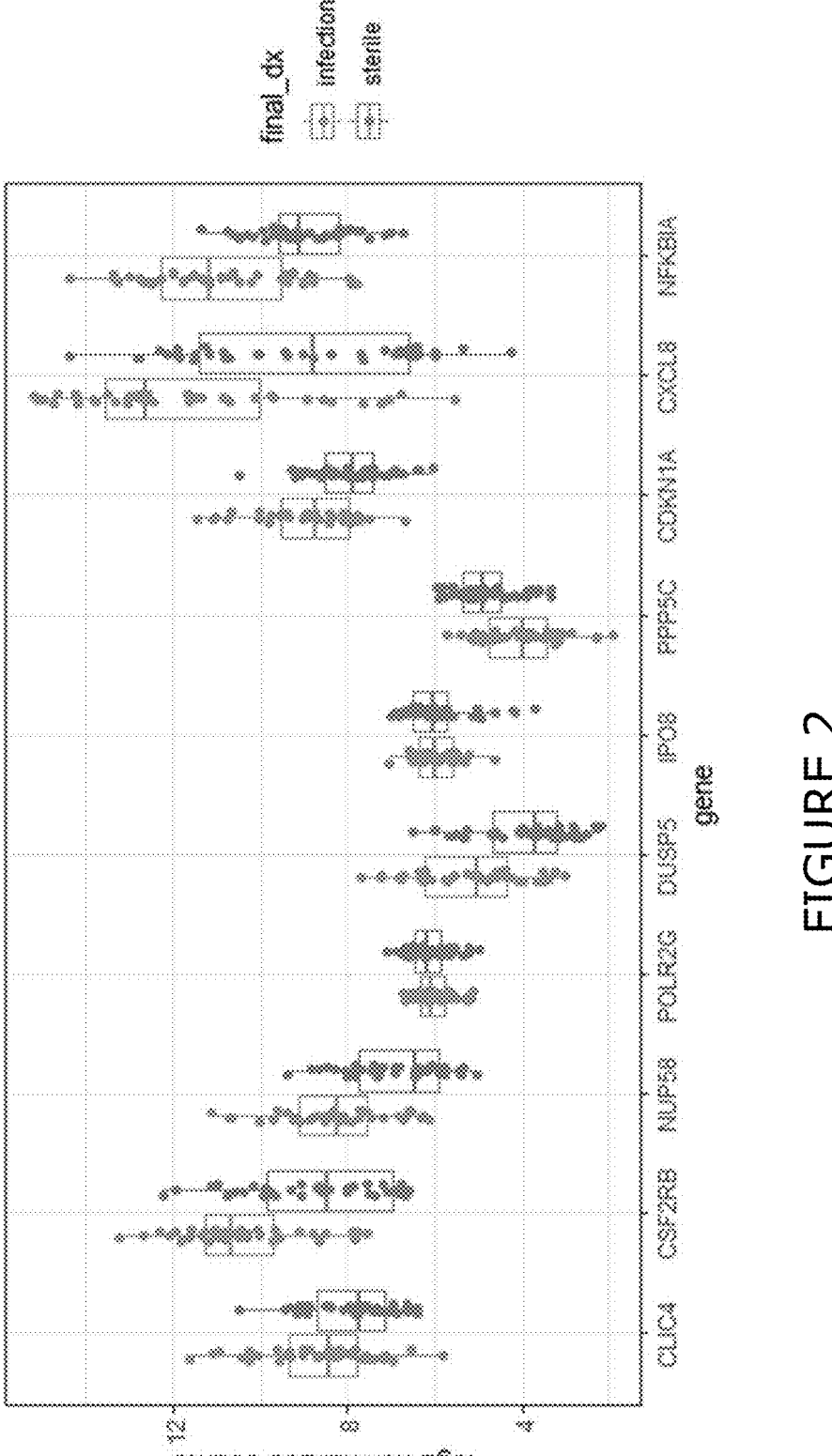
FIG. 2 is a graphical representation showing expression levels of CLIC4, CSF2RB, NUP58, POLR2G, DUSP5, IPO8, PPP5C, CDKN1A, CXCL8 and NFKBIA in subjects with infectious joint inflammation and in subjects with non-infectious joint inflammation.

In particular embodiments, a plurality of biomarkers selected from CDKN1A, CLIC4, CSF2RB, DUSP5, IPO8, NFKBIA, NUP58, POLR2G and PPP5C is used to determine the indicator. These biomarkers have strong discrimination performance in distinguishing between infectious and non-infectious joint inflammation. FIG. 2 shows the expression levels of these biomarkers in subjects with infectious Alternatively, biomarker values may be combined by measuring a composite level of two or more (e.g., 2, 3, 4, 5, 6, 7, 8, 9, 10, 11, 12, 13, 14, 15, 16 or more) biomarkers. For example, a first label (e.g., first fluorophore) may be used to measure the composite level of a first subset of biomarkers that are expressed at a higher level in infectious inflammation than in non-infectious inflammation and a second label (e.g., second fluorophore) may be used to measure the composite level of a second subset of biomarkers that are expressed at a lower level in non-infectious inflammation than in infectious inflammation. Measurement of the first label thus provides a combined biomarker value for the first biomarker subset and measurement of the second label thus provides a combined biomarker value for the second biomarker subset.

In particular embodiments, the function is a division and one member of a pair of biomarker values is divided by the other member of the pair to provide a ratio of levels of a pair of joint inflammation biomarkers. Thus, in these embodiments, if the biomarker values denote the levels of a pair of joint inflammation biomarkers, then the functionalized biomarker value will be based on a ratio of the biomarker values. However, in other embodiments in which the biomarker values represent amplification amounts, or cycle times (e.g., PCR cycle times), which are a logarithmic representation of the level of the joint inflammation biomarkers in a sample, then the biomarker values may be combined in some other manner, such as by subtracting the cycle times to determine a functionalized biomarker value indicative of a ratio of the levels of the joint inflammation biomarkers.

For example, in embodiments that utilize a first biomarker and a second biomarker according to TABLE A and logarithmic representations (e.g., a PCR cycle time) of measured amounts or concentrations of biomarkers are employed, the detection method may comprise subtracting the biomarker value for the second biomarker from the biomarker value for the first biomarker to provide a composite score, on which at least in part the indicator is determined.

Alternatively, in embodiments that utilize a first biomarker, a second biomarker, a third biomarker and optional fourth biomarker according to TABLE B and logarithmic representations (e.g., a PCR cycle time) of measured amounts or concentrations of biomarkers are employed, the detection methods may further comprise adding the biomarker values for the first biomarker and the second biomarker to provide a first summed biomarker value, adding the biomarker values for the third biomarker and fourth biomarker, if present, to provide a second summed biomarker value, and subtracting the second summed biomarker value from the first summed biomarker value to provide a composite score, on which at least in part the indicator is determined.

In embodiments that employ a first biomarker, second biomarker, third biomarker, optional fourth biomarker, fifth biomarker, sixth biomarker and optional seventh and eighth biomarkers according to TABLE C and logarithmic representations (e.g., a PCR cycle time) of measured amounts or concentrations of biomarkers are employed, the detection method may further comprise adding the biomarker values for the first biomarker, second biomarker, third biomarker and optional fourth biomarker, if present, to provide a first summed biomarker value, adding the biomarker values for the fifth biomarker, sixth biomarker and optional seventh and eighth biomarkers, if present, to provide a second summed biomarker value, subtracting the second summed biomarker value from the first summed biomarker value to provide a composite score, on which at least in part the indicator is determined. In some examples of this type, the addition of the biomarker values that yields the first summed biomarker value comprises twice adding the biomarker value for one or more of the first biomarker, second biomarker, third biomarker and optional fourth biomarker, which preferably has the strongest discrimination performance.

In representative examples, the composite score is determined using one of the following formulas:

$$[CLIC4 + CLIC4 + CSF2RB + NUP58] - [IPO8 + POLR2G]$$

$$[CLIC4 + CLIC4 + CSF2RB + NUP58] - [POLR2G + PPP5C + VPS4B]$$

$$[CLIC4 + CLIC4 + DUSP5 + SP2] - [PKN1 + PLEC + PPP5C + RNF26]$$

$$[CLIC4 + CLIC4 + NUP58 + SP2] - [PKN1 + PLEC + PPP5C + VPS4B]$$

$$[CLIC4 + CLIC4 + CSF2RB + DUSP5] - [PLEC + POLR2G + PSMC3]$$

44

-continued $$[CLIC4 + CSF2RB + DUSP5 + RNASEL] - [ATG4B + KLF13 + POLR2G]$$

$$[CLIC4 + CSF2RB + NUP58 + SNIP1] - [POLR2G + PPIL2 + VPS4B]$$

$$[CLIC4 + CLIC4 + CSF2RB + DUSP5] - [POLR2G + PPP5C + RNF26]$$

$$[CLIC4 + CLIC4 + NUP58 + SP2] - [PKN1 + PLEC + PPP5C + SEC24B]$$

$$[CLIC4 + CLIC4 + CSF2RB + DUSP5] - $$
$$[MYO1F + PLEC + PPP5C + RNF26]$$

$$[CLIC4 + CLIC4 + PPIF + SP2] - [PKN1 + PLEC + PPP5C + SLC26A6]$$

$$[CLIC4 + CLIC4 + CSF2RB + NUP58] - [KLHL12 + POLR2G + PPP5C]$$

$$[CLIC4 + CLIC4 + DUSP5 + SP2] - [PKN1 + PLEC + PPP5C + PSMC3]$$

$$[CLIC4 + CLIC4 + CSF2RB + DUSP5] - $$
$$[CSNK1D + PPP5C + PPP5C + RNF26]$$

$$[CLIC4 + CLIC4 + CSF2RB + DUSP5] - [AP3M1 + PPP5C + RNF26]$$

$$[CLIC4 + CLIC4 + CSF2RB + DUSP5] - [PLXDC2 + PPP5C + RNF26]$$

$$[CLIC4 + CLIC4 + DUSP5 + SP2] - [KCTD3 + PKN1 + PLEC + PPP5C]$$

$$[CLIC4 + CLIC4 + NUP58 + SP2] - [PKN1 + PLEC + POLR2G]$$

$$[CLIC4 + CLIC4 + DUSP5 + $$
$$NUP58] - [PLEC + PPP5C + RNF26 + SEC24B]$$

$$[CLIC4 + CLIC4 + DUSP5 + SP2] - [KLF13 + PLEC + PPP5C + RNF26].$$

If desired, the detection methods may further comprise analyzing the biomarker value(s) or composite score with reference to one or more corresponding controls, to determine the indicator. In some embodiments, an individual control comprises a reference biomarker value range or threshold value, or composite score range or threshold value. For example, the indicator generally indicates a likelihood of a presence of infectious inflammation if the biomarker value(s) or composite score is indicative of the level of the biomarker(s) in the sample that correlates with an increased likelihood of a presence of infectious inflammation relative to a control (e.g., a predetermined reference biomarker value range or cut-off value). Alternatively, the indicator generally indicates a likelihood of the presence of non-infectious inflammation if the biomarker value(s) or composite score is indicative of the level of the biomarker(s) in the sample that correlates with an increased likelihood of the presence of non-infectious inflammation relative to a control (e.g., a predetermined reference biomarker value range or cut-off value).

In some embodiments, a composite score is aggregated with one or more clinical parameters to provide an adjusted composite score on which the indicator is determined.

In some embodiments, biomarker values are determined for CDKN1A, CLIC4, CSF2RB, DUSP5, IPO8, NFKBIA, NUP58, POLR2G and PPP5C, optionally in combination with a reference or control biomarker and an indicator indicative of a likelihood that the subject has infectious joint inflammation, or not, is determined using the following algorithm:

$$1 > \{NFKBIA\}/\{CSF2RB\}$$
$$AND\ 1 > \{NKFBIA\}/\{NUP58\}$$
$$AND\ 2 > \{NFKBIA\}/\{POLR2G\}$$

-continued $$AND\ 2 > \{NFKBIA\}/\{DUSP5\}$$

$$AND\ 3 > \{NFKBIA\}/\{IPO8\}$$

$$AND\ \{NFKBIA\}/\{PPP5C\} > 0.7$$

$$AND\ \{NFKBIA\}/\{CDKN1A\} > 3.5$$

$$AND\ \{CSF2RB\}/\{CLIC4\} > 0.9$$

$$AND\ 1 > \{CSF2RB\}/\{NUP58\}$$

$$AND\ \{CSF2RB\}/\{POLR2G\} > 0.5$$

$$AND\ \{CSF2RB\}/\{DUSP5\} > 1$$

$$AND\ \{CSF2RB\}/\{IPO8\} > 0.9$$

$$AND\ \{CSF2RB\}/\{PPP5C\} > 1.5$$

$$AND\ 2.5 > \{NUP58\}/\{CSF2RB\}$$

$$AND\ \{NUP58\}/\{CLIC4\} > 0.9$$

$$AND\ \{NUP58\}/\{POLR2G\} > 1$$

$$AND\ \{NUP58\}/\{DUSP5\} > 1.2$$

$$AND\ \{NUP58\}/\{IPO8\} > 2$$

$$AND\ \{NUP58\}/\{PPP5C\} > 3$$

$$AND\ \{NUP58\}/\{CDKN1A\} > 5$$

$$AND\ \{NUP58\}/\{NFKBIA\} > 1.3$$

$$AND\ \{NUP58\}/\{FBXO28.RNA\ ref\ Low\ 1\} > 4.$$

In other embodiments, biomarker values are determined for CDKN1A, CLIC4, CSF2RB, DUSP5, IPO8, NFKBIA, NUP58, POLR2G and PPP5C, optionally in combination with a reference or control biomarker and an indicator indicative of a likelihood that the subject has infectious joint inflammation, or not, is determined using the following algorithm:

$$0.75 > \{CLIC4\}/\{CSF2RB\}$$

$$AND\ \{CLIC4\}/\{POLR2G\} > 0.5$$

$$AND\ \{CLIC4\}/\{DUSP5\} > 0.5$$

$$AND\ \{CLIC4\}/\{PPP5C\} > 0.5.$$

The above algorithms may be used for a sample taken from a native joint, or from an artificial or prosthetic joint.

2.4 Analysis of Biomarker Data

Biomarker data may be analyzed by a variety of methods to identify biomarkers and determine the statistical significance of differences in observed levels of biomarkers between test and reference expression profiles in order to evaluate whether a patient has infectious joint inflammation or inflammation arising from a non-infectious source, such as traumatic injury, surgery (e.g., joint repair or joint replacement), autoimmune disease (e.g., rheumatoid arthritis, psoriatic arthritis and lupus-related arthritis), osteoarthritis, gouty arthritis, or related to painful local tissues affected by bursitis, tenosynovitis, epicondylitis, synovitis and/or other disorders. For any particular joint inflammation biomarker, a distribution of joint inflammation biomarker levels for subjects with infectious joint inflammation or non-infectious joint inflammation will likely overlap. Under such conditions, a test does not absolutely distinguish a first condition (e.g., infectious joint inflammation) and a second condition (e.g., non-infectious joint inflammation) with 100% accuracy, and the area of overlap indicates where the test cannot distinguish the first condition and the second condition. A threshold is selected, above which (or below which, depending on how a joint inflammation biomarker changes with a specified condition or prognosis) the test is considered to be "positive" and below which the test is considered to be "negative." The area under the ROC curve (AUC) provides the C-statistic, which is a measure of the probability that the perceived measurement will allow correct identification of a condition (see, e.g., Hanley et al., Radiology 143:29-36 (1982)).

Alternatively, or in addition, thresholds may be established by obtaining an earlier biomarker result from the same patient, to which later results may be compared. In these embodiments, the individual in effect acts as their own "control group." In biomarkers that increase with condition severity or prognostic risk, an increase over time in the same patient can indicate a worsening of the condition or a failure of a treatment regimen, while a decrease over time can indicate remission of the condition or success of a treatment regimen.

In some embodiments, a positive likelihood ratio, negative likelihood ratio, odds ratio, and/or AUC or receiver operating characteristic (ROC) values are used as a measure of a method's ability to predict risk or to diagnose a disease or condition (e.g., infectious joint inflammation or non-infectious joint inflammation). As used herein, the term "likelihood ratio" is the probability that a given test result would be observed in a subject with a condition of interest divided by the probability that that same result would be observed in a patient without the condition of interest. Thus, a positive likelihood ratio is the probability of a positive result observed in subjects with the specified condition (e.g., infectious joint inflammation or non-infectious joint inflammation) divided by the probability of a positive results in subjects without the specified condition. A negative likelihood ratio is the probability of a negative result in subjects without the specified condition divided by the probability of a negative result in subjects with specified condition. The term "odds ratio," as used herein, refers to the ratio of the odds of an event occurring in one group (e.g., infectious joint inflammation) to the odds of it occurring in another group (e.g., non-infectious joint inflammation), or to a data-based estimate of that ratio. The term "area under the curve" or "AUC" refers to the area under the curve of a receiver operating characteristic (ROC) curve, both of which are well known in the art. AUC measures are useful for comparing the accuracy of a classifier across the complete data range. Classifiers with a greater AUC have a greater capacity to classify unknowns correctly between two groups of interest (e.g., infectious joint inflammation and non-infectious joint inflammation). ROC curves are useful for plotting the performance of a particular feature (e.g., any of the joint inflammation biomarkers disclosed herein and/or any item of additional biomedical information) in distinguishing or discriminating between two populations (e.g., infectious joint inflammation and non-infectious joint inflammation). Typically, the feature data across the entire population (e.g., subjects with infectious joint inflammation and subjects with non-infectious joint inflammation) are sorted in ascending order based on the value of a single feature. Then, for each value for that feature, the true positive and false positive rates for the data are calculated. The sensitivity is determined by counting the number of cases above the value for that feature and then dividing by the total number of cases. The specificity is determined by counting the number of controls below the value for that feature and then dividing by the total number of controls. Although this definition refers to scenarios in which a feature is elevated in one patient group compared to another patient group, this definition also applies to scenarios in which a feature is lower in one patient group compared to the other patient group (in such a scenario, samples below the value for that feature would be counted). ROC curves can be generated for a single feature as well as for other single outputs, for example, a combination of two or more features (e.g., a combination of two or more biomarker values) can be mathematically combined (e.g., added, subtracted, multiplied, etc.) to produce a single value, and this single value can be plotted in a ROC curve. Additionally, any combination of multiple features (e.g., a combination of multiple biomarker values), in which the combination derives a single output value, can be plotted in a ROC curve. These combinations of features may comprise a test. The ROC curve is the plot of the sensitivity of a test against the specificity of the test, where sensitivity is traditionally presented on the vertical axis and specificity is traditionally presented on the horizontal axis. Thus, "AUC ROC values" are equal to the probability that a classifier will rank a randomly chosen positive instance higher than a randomly chosen negative one. An AUC ROC value may be thought of as equivalent to the Mann-Whitney U test, which tests for the median difference between scores obtained in the two groups considered if the groups are of continuous data, or to the Wilcoxon test of ranks.

In some embodiments, at least one (e.g., 1, 2, 3, 4, 5, 6, 7, 8, 9, 10, or more) joint inflammation biomarker or a panel of joint inflammation biomarkers is selected to discriminate between subjects with a first condition (e.g., infectious joint inflammation) and subjects with a second condition (e.g., non-infectious joint inflammation) with at least about 50%, 55% 60%, 65%, 70%, 75%, 80%, 85%, 90%, 95% accuracy or having a C-statistic of at least about 0.50, 0.55, 0.60, 0.65, 0.70, 0.75, 0.80, 0.85, 0.90, 0.95.

In the case of a positive likelihood ratio, a value of 1 indicates that a positive result is equally likely among subjects in both the "first condition" and "second condition" groups; a value greater than 1 indicates that a positive result is more likely in the first condition group; and a value less than 1 indicates that a positive result is more likely in the second condition group. In this context, "first condition" group is meant to refer to a group having one characteristic (e.g., the presence of infectious inflammation) and "second condition" group lacking the same characteristic. In the case of a negative likelihood ratio, a value of 1 indicates that a negative result is equally likely among subjects in both the "first condition" and "second condition" groups; a value greater than 1 indicates that a negative result is more likely in the "first condition" group; and a value less than 1 indicates that a negative result is more likely in the "second condition" group. In the case of an odds ratio, a value of 1 indicates that a positive result is equally likely among subjects in both the "first condition" and "second condition" groups; a value greater than 1 indicates that a positive result is more likely in the "first condition" group; and a value less than 1 indicates that a positive result is more likely in the "second condition" group. In the case of an AUC ROC value, this is computed by numerical integration of the ROC curve. The range of this value can be 0.5 to 1.0. A value of 0.5 indicates that a classifier (e.g., a joint inflammation biomarker profile) is no better than a 50% chance to classify unknowns correctly between two groups of interest (e.g., infectious joint inflammation and non-infectious joint inflammation), while 1.0 indicates the relatively best diagnostic accuracy. In certain embodiments, individual joint inflammation biomarkers and/or joint inflammation biomarker panels are selected to exhibit a positive or negative likelihood ratio of at least about 1.5 or more or about 0.67 or less, at least about 2 or more or about 0.5 or less, at least about 5 or more or about 0.2 or less, at least about 10 or more or about 0.1 or less, or at least about 20 or more or about 0.05 or less.

In certain embodiments, individual joint inflammation biomarkers and/or joint inflammation biomarker panels are selected to exhibit an odds ratio of at least about 2 or more or about 0.5 or less, at least about 3 or more or about 0.33 or less, at least about 4 or more or about 0.25 or less, at least about 5 or more or about 0.2 or less, or at least about 10 or more or about 0.1 or less.

In certain embodiments, individual joint inflammation biomarkers and/or joint inflammation biomarker panels are selected to exhibit an AUC ROC value of greater than 0.5, preferably at least 0.6, more preferably 0.7, still more preferably at least 0.8, even more preferably at least 0.9, and most preferably at least 0.95.

In some cases, multiple thresholds may be determined in so-called "tertile," "quartile," or "quintile" analyses. In these methods, the "diseased" and "control groups" (or "high risk" and "low risk") groups are considered together as a single population, and are divided into 3, 4, or 5 (or more) "bins" having equal numbers of individuals. The boundary between two of these "bins" may be considered "thresholds." A risk (of a particular diagnosis or prognosis for example) can be assigned based on which "bin" a test subject falls into.

In other embodiments, particular thresholds for the joint inflammation biomarker(s) measured are not relied upon to determine if the biomarker level(s) obtained from a subject are correlated to a particular diagnosis or prognosis. For example, a temporal change in the biomarker(s) can be used to rule in or out one or more particular diagnoses and/or prognoses. Alternatively, joint inflammation biomarker(s) may be correlated to a condition, disease, prognosis, etc., by the presence or absence of one or more joint inflammation biomarkers in a particular assay format. In the case of joint inflammation biomarker panels, the detection methods disclosed herein may utilize an evaluation of the entire population or subset of joint inflammation biomarkers disclosed herein to provide a single result value (e.g., a "panel response" value expressed either as a numeric score or as a percentage risk). In such embodiments, an increase, decrease, or other change (e.g., slope over time) in a certain subset of joint inflammation biomarkers may be sufficient to indicate a particular condition or future outcome in one patient, while an increase, decrease, or other change in a different subset of joint inflammation biomarkers may be sufficient to indicate the same or a different condition or outcome in another patient.

In certain embodiments, a panel of joint inflammation biomarkers is selected to assist in distinguishing a pair of groups (i.e., assist in assessing whether a subject has an increased likelihood of being in one group or the other group of the pair) selected from "non-infectious joint inflammation" and "infectious joint inflammation" or "low risk" and "high risk" with at least about 70%, 80%, 85%, 90% or 95% sensitivity, suitably in combination with at least about 70% 80%, 85%, 90% or 95% specificity. In some embodiments, both the sensitivity and specificity are at least about 75%, 80%, 85%, 90% or 95%.

The phrases "assessing the likelihood" and "determining the likelihood," as used herein, refer to methods by which the skilled artisan can predict the presence or absence of a condition (e.g., infectious joint inflammation or non-infectious joint inflammation) in a patient. The skilled artisan will understand that this phrase includes within its scope an increased probability that a condition is present or absent in a patient; that is, that a condition is more likely to be present or absent in a subject. For example, the probability that an individual identified as having a specified condition actually has the condition may be expressed as a "positive predictive value" or "PPV." Positive predictive value can be calculated as the number of true positives divided by the sum of the true positives and false positives. PPV is determined by the characteristics of the predictive methods disclosed herein as well as the prevalence of the condition in the population analyzed. The statistical algorithms can be selected such that the positive predictive value in a population having a condition prevalence is in the range of 70% to 99% and can be, for example, at least 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In other examples, the probability that an individual identified as not having a specified condition actually does not have that condition may be expressed as a "negative predictive value" or "NPV." Negative predictive value can be calculated as the number of true negatives divided by the sum of the true negatives and false negatives. Negative predictive value is determined by the characteristics of the diagnostic or prognostic method, system, or code as well as the prevalence of the disease in the population analyzed. The statistical methods and models can be selected such that the negative predictive value in a population having a condition prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some embodiments, a subject is determined as having a significant likelihood of having or not having a specified condition (e.g., infectious joint inflammation or non-infectious joint inflammation). By "significant likelihood" is meant that the subject has a reasonable probability (0.6, 0.7, 0.8, 0.9 or more) of having, or not having, a specified condition.

The joint inflammation biomarker analysis disclosed herein permits the generation of high-density data sets that can be evaluated using informatics approaches. High data density informatics analytical methods are known and software is available to those in the art, e.g., cluster analysis (Pirouette, Informetrix), class prediction (SIMCA-P, Umetrics), principal components analysis of a computationally modeled dataset (SIMCA-P, Umetrics), 2D cluster analysis (GeneLinker Platinum, Improved Outcomes Software), and metabolic pathway analysis (biotech.icmb.utexas.edu). The choice of software packages offers specific tools for questions of interest (Kennedy et al., Solving Data Mining Problems Through Pattern Recognition. Indianapolis: Prentice Hall PTR, 1997; Golub et al., (2999) Science 286:531-7; Eriksson et al., Multi and Megavariate Analysis Principles and Applications: Umetrics, Umea, 2001). In general, any suitable mathematic analyses can be used to evaluate at least one (e.g., 1, 2, 3, 4, 5, 6, 7, 8, 9, 10, etc.) joint inflammation biomarker in a joint inflammation biomarker population disclosed herein with respect to a condition selected from infectious joint inflammation and non-infectious joint inflammation. For example, methods such as multivariate analysis of variance, multivariate regression, and/or multiple regression can be used to determine relationships between dependent variables (e.g., clinical measures) and independent variables (e.g., levels of joint inflammation biomarkers). Clustering, including both hierarchical and non-hierarchical methods, as well as non-metric Dimensional Scaling can be used to determine associations or relationships among variables and among changes in those variables.

In addition, principal component analysis is a common way of reducing the dimension of studies, and can be used to interpret the variance-covariance structure of a data set. Principal components may be used in such applications as multiple regression and cluster analysis. Factor analysis is used to describe the covariance by constructing "hidden" variables from the observed variables. Factor analysis may be considered an extension of principal component analysis, where principal component analysis is used as parameter estimation along with the maximum likelihood method. Furthermore, simple hypothesis such as equality of two vectors of means can be tested using Hotelling's T squared statistic.

In some embodiments, the data sets corresponding to joint inflammation biomarker panels are used to create a diagnostic or predictive rule or model based on the application of a statistical and machine learning algorithm. Such an algorithm uses relationships between a joint inflammation biomarker panel and a condition selected from infectious joint inflammation and non-infectious joint inflammation observed in control subjects or typically cohorts of control subjects (sometimes referred to as training data), which provides combined control or reference joint inflammation biomarker panels for comparison with joint inflammation biomarker panels of a subject. The data are used to infer relationships that are then used to predict the status of a subject, including the presence or absence of one of the conditions referred to above.

Practitioners skilled in the art of data analysis recognize that many different forms of inferring relationships in the training data may be used without materially changing the detection methods disclosed herein. The data presented in the Tables and Examples herein has been used to generate illustrative minimal combinations of joint inflammation biomarkers (models) that differentiate between infectious joint inflammation and non-infectious joint inflammation using feature selection based on AUC maximization in combination with analytical model classification, including for example classification using one or more of: an additive model; a linear model; a support vector machine; a neural network model; a random forest model; a regression model; a genetic algorithm; an annealing algorithm; a weighted sum; a nearest neighbor model; and a probabilistic model. The biomarker tables disclosed herein provide illustrative lists of joint inflammation biomarkers ranked according to their p value. Illustrative models comprising at least 2, at least 3, at least 4, at least 5, at least 6, at least 7, at least 8 joint inflammation biomarkers were able to develop a classifier or generative algorithm for discriminating between two control groups as defined above with significantly improved positive predictive values compared to conventional methodologies. This algorithm can be advantageously applied to determine presence or probability of infectious joint inflammation or non-infectious joint inflammation in a patient, and thus diagnose the patient as having or as likely to have joint inflammation or non-infectious joint inflammation.

In some embodiments, evaluation of joint inflammation biomarkers includes determining the levels of individual joint inflammation biomarkers, which correlate with the presence or absence of a condition, as defined above. In certain embodiments, the techniques used for detection of joint inflammation biomarkers may include internal or external standards to permit quantitative or semi-quantitative determination of those biomarkers, to thereby enable a valid comparison of the level of the joint inflammation biomarkers in a biological sample with the corresponding joint inflammation biomarkers in a reference sample or samples. Such standards can be determined by the skilled practitioner using standard protocols. In specific examples, absolute values for the level or functional activity of individual expression products are determined.

In semi-quantitative methods, a threshold or cut-off value is suitably determined, and is optionally a predetermined value. In particular embodiments, the threshold value is predetermined in the sense that it is fixed, for example, based on previous experience with the assay and/or a population of affected and/or unaffected subjects. Alternatively, the predetermined value can also indicate that the method of arriving at the threshold is predetermined or fixed even if the particular value varies among assays or may even be determined for every assay run.

In some embodiments, the level of a joint inflammation biomarker is normalized against a housekeeping biomarker. The term "housekeeping biomarker" refers to a biomarker or group of biomarkers (e.g., polynucleotides and/or polypeptides), which are typically found at a constant level in the cell type(s) being analyzed and across the conditions being assessed. In some embodiments, the housekeeping biomarker is a "housekeeping gene." A "housekeeping gene" refers herein to a gene or group of genes which encode proteins whose activities are essential for the maintenance of cell function and which are typically found at a constant level in the cell type(s) being analyzed and across the conditions being assessed.

There is no intended limitation on the methodology used to normalize the values of the measured biomarkers provided that the same methodology is used for testing a human subject sample as was used to generate a risk categorization table or threshold value. Many methods for data normalization exist and are familiar to those skilled in the art. These include methods such as background subtraction, scaling, MoM analysis, linear transformation, least squares fitting, etc. The goal of normalization is to equate the varying measurement scales for the separate biomarkers such that the resulting values may be combined according to a weighting scale as determined and designed by the user or by the machine learning system and are not influenced by the absolute or relative values of the biomarker found within nature.

In certain embodiments, the biomarkers are measured and those resulting values normalized and then summed to obtain a composite score. In certain aspects, normalizing the measured biomarker values comprises determining the multiple of median (MoM) score. In other aspects, the present method further comprises weighting the normalized values before summing to obtain a composite score. If desired, a machine learning system may be utilized to determine weighting of the normalized values as well as how to aggregate the values (e.g., determine which biomarkers are most predictive, and assign a greater weight to these markers). In some embodiments, composite scores include one or more clinical parameters of the patient. Representative clinical parameters include joint pain, joint stiffness, tenderness, swelling, warmth, patient global health assessment, cell counts (e.g., white blood cell counts for example in serum and/or in synovial fluid), erythrocyte sedimentation rate (ESR) and C-reactive protein (CRP) levels.

In certain embodiments, the detection methods utilize a risk categorization table to generate a risk score for a patient based on a composite score by comparing the composite score with a reference set derived from a cohort of patients with infectious joint inflammation and/or from a cohort of patients with non-infectious joint inflammation. The detection methods may further comprise quantifying the increased risk for the presence of infectious joint inflammation or for the presence of non-infectious joint inflammation for the subject as a risk score, wherein the composite score (combined obtained biomarker value and optionally obtained clinical parameter values) is matched to a risk category of a grouping of stratified subject populations wherein each risk category comprises a multiplier (or percentage) indicating an increased likelihood of having infectious joint inflammation or non-infectious joint inflammation correlated to a range of composite scores. This quantification is based on the pre-determined grouping of a stratified cohort of subjects. In some embodiments, the grouping of a stratified population of subjects, or stratification of a disease cohort, is in the form of a risk categorization table. The selection of the disease cohort, the cohort of subjects that share infectious joint inflammation or non-infectious joint inflammation risk factors, are well understood by those skilled in the art of joint inflammation research. However, the skilled person would also recognize that the resulting stratification, may be more multidimensional and take into account further environmental, occupational, genetic, or biological factors (e.g., epidemiological factors).

After quantifying the increased risk for presence of infectious joint inflammation or presence of non-infectious joint inflammation in the form of a risk score, this score may be provided in a form amenable to understanding by a physician. In certain embodiments, the risk score is provided in a report. In certain aspects, the report may comprise one or more of the following: patient information, a risk categorization table, a risk score relative to a cohort population, one or more biomarker test scores, a biomarker composite score, a master composite score, identification of the risk category for the patient, an explanation of the risk categorization table, and the resulting test score, a list of biomarkers tested, a description of the disease cohort, environmental and/or occupational factors, cohort size, biomarker velocity, genetic mutations, family history, margin of error, and so on.

3. Kits

All the essential reagents required for detecting and quantifying the joint inflammation biomarkers disclosed herein may be assembled together in a kit. In some embodiments, the kit comprises a reagent that permits quantification of at least one joint inflammation biomarker or each joint inflammation biomarker of a biomarker panel disclosed herein. In the context of the present disclosure, "kit" is understood to mean a product containing the different reagents necessary for carrying out the methods of the disclosure packed so as to allow their transport and storage. Additionally, the kits of the present disclosure can contain instructions for the simultaneous, sequential or separate use of the different components contained in the kit. The instructions can be in the form of printed material or in the form of an electronic support capable of storing instructions such that they can be read by a subject, such as electronic storage media (magnetic disks, tapes and the like), optical media (CD-ROM, DVD) and the like. Alternatively or in addition, the media can contain internet addresses that provide the instructions. The kits may contain software for interpreting assay data to determine the likelihood of the presence or absence of infectious joint inflammation or non-infectious joint inflammation, and/or for ruling out infectious joint inflammation. In some embodiments, the kits may provide a means to access a machine learning system provided, for example, as a software as a service (Saas) deployment.

Reagents that allow quantification of a joint inflammation biomarker include compounds or materials, or sets of compounds or materials, which allow quantification of the joint inflammation biomarker. In specific embodiments, the compounds, materials or sets of compounds or materials permit determining the expression level of a gene (e.g., joint inflammation biomarker gene) include without limitation the extraction of RNA material, the determination of the level of a corresponding RNA, etc., primers for the synthesis of a corresponding cDNA, primers for amplification of DNA, and/or probes capable of specifically hybridizing with the RNAs (or the corresponding cDNAs) encoded by the genes, TaqMan™ probes, etc.

Kit reagents can be in liquid form or can be lyophilized. Suitable containers for the reagents include, for example, bottles, vials, syringes, and test tubes. Containers can be formed from a variety of materials, including glass or plastic. The kit can also comprise a package insert containing written instructions for methods of diagnosing infectious joint inflammation and non-infectious joint inflammation.

The kits may also optionally include appropriate reagents for detection of labels, positive and negative controls, washing solutions, blotting membranes, microtiter plates, dilution buffers and the like. For example, a nucleic acid-based detection kit may include (i) a joint inflammation biomarker polynucleotide (which may be used as a positive control), (ii) a primer or probe that specifically hybridizes to a joint inflammation biomarker polynucleotide. Also included may be enzymes suitable for amplifying nucleic acids including various polymerases (reverse transcriptase, Taq polymerase, Sequenase™, DNA ligase etc. depending on the nucleic acid amplification technique employed), deoxynucleotides and buffers to provide the necessary reaction mixture for amplification. Such kits also generally will comprise, in suitable means, distinct containers for each individual reagent and enzyme as well as for each primer or probe. Alternatively, a protein-based detection kit may include (i) a joint inflammation biomarker polypeptide (which may be used as a positive control), (ii) an antibody that binds specifically to a joint inflammation biomarker polypeptide. The kit can also feature various devices (e.g., one or more) and reagents (e.g., one or more) for performing one of the assays described herein; and/or printed instructions for using the kit to quantify the expression of a joint inflammation biomarker gene and/or carry out an indicator-determining method, as broadly described above and elsewhere herein.

The reagents described herein, which may be optionally associated with detectable labels, can be presented in the format of a microfluidics card, a reaction vessel, a microarray or a kit adapted for use with the assays described in the examples or below, e.g., RT-PCR or Q PCR techniques described herein.

The reagents also have utility in compositions for detecting and quantifying the biomarkers of the present disclosure. For example, a reverse transcriptase may be used to reverse transcribe RNA transcripts, including mRNA, in a nucleic acid sample, to produce reverse transcribed transcripts, including reverse transcribed mRNA (also referred to as "cDNA"). In specific embodiments, the reverse transcribed mRNA is whole cell reverse transcribed mRNA (also referred to herein as "whole cell cDNA"). The nucleic acid sample is suitably derived from a sample disclosed herein.

The reagents are suitably used to quantify the reverse transcribed transcripts (i.e., cDNA). For example, oligonucleotide primers that hybridize to the cDNA can be used to amplify at least a portion of the cDNA via a suitable nucleic acid amplification technique, e.g., RT-PCR or qPCR techniques described herein. Alternatively, oligonucleotide probes may be used to hybridize to the cDNA for the quantification, using a nucleic acid hybridization analysis technique (e.g., microarray analysis), as described for example above. Thus, in some embodiments, a respective oligonucleotide primer or probe is hybridized to a complementary nucleic acid sequence of a cDNA in the compositions of the present disclosure. The compositions typically comprise labeled reagents for detecting and/or quantifying one or more cDNAs. Representative reagents of this type include labeled oligonucleotide primers or probes (e.g., TaqMan™ probe) that hybridize to RNA transcripts or reverse transcribed RNA, labeled RNA, labeled cDNA as well as labeled oligonucleotide linkers or tags (e.g., a labeled RNA or DNA linker or tag) for labeling (e.g., end labeling such as 3' end labeling) RNA or reverse transcribed RNA. The primers, probes, RNA or CDNA (whether labeled or non-labeled) may be immobilized or free in solution. Representative reagents of this type include labeled oligonucleotide primers or probes that hybridize to cDNA as well as labeled cDNA. The label can be any reporter molecule as known in the art, illustrative examples of which are described above and elsewhere herein.

The kits disclosed herein al encompasses non-reverse transcribed RNA embodiments in which cDNA is not made and the RNA transcripts are directly the subject of the analysis. Thus, in other embodiments, reagents are suitably used to quantify RNA transcripts directly. For example, oligonucleotide probes can be used to hybridize to transcripts for quantification of joint inflammation biomarkers of the present disclosure, using a nucleic acid hybridization analysis technique (e.g., microarray analysis), as described for example above. Thus, in some embodiments, a respective oligonucleotide probe is hybridized to a complementary nucleic acid sequence of joint inflammation biomarker transcript in the disclosed compositions. In illustrative examples of this type, the compositions may comprise labeled reagents that hybridize to transcripts for detecting and/or quantifying the transcripts. Representative reagents of this type include labeled oligonucleotide probes that hybridize to transcripts as well as labeled transcripts. The primers or probes may be immobilized or free in solution.

The present kits have a number of applications. For example, the kits can be used to determine if a subject has infectious joint inflammation or joint inflammation arising from a non-infectious source, such as traumatic injury, surgery, autoimmune disease, etc. In another example, the kits can be used to determine if a patient should be treated for infectious joint inflammation, for example, with broad spectrum antibiotics, or treated for non-infectious joint inflammation using for example a corticosteroid or non-steroidal anti-inflammatories. In another example, kits can be used to monitor the effectiveness of treatment of a patient infectious joint inflammation or non-infectious joint inflammation. In a further example, the kits can be used to identify compounds that modulate expression of one or more of the joint inflammation biomarkers in in vitro or in vivo animal models to determine the effects of treatment.

4. Treatment Embodiments

Also disclosed herein are methods for treating or managing the development or progression of infectious joint inflammation or non-infectious joint inflammation in subject with joint pain and/or at least one clinical sign of joint inflammation. A subject positively identified as having infectious joint inflammation may be exposed to an anti-microbial agent such as but not limited to an anti-bacterial agent, an anti-viral agent, an anti-fungal/anti-yeast agent and an anti-protozoal agent, illustrative examples of which include:

Anti-bacterial agents: Amikacin, Gentamicin, Kanamycin, Neomycin, Netilmicin, Tobramycin, Paromomycin, Streptomycin, Spectinomycin, Geldanamycin, Herbimycin, Rifaximin, Loracarbef, Ertapenem, Doripenem, Imipenem/Cilastatin, Meropenem, Cefadroxil, Cefazolin, Cefalotin or Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, Ceftobiprole, Teicoplanin, Vancomycin, Telavancin, Dalbavancin, Oritavancin, Clindamycin, Lincomycin, Daptomycin, Azithromycin, Clarithromycin, Dirithromycin, Erythromycin, Roxithromycin, Troleandomycin, Telithromycin, Spiramycin, Aztreonam, Furazolidone, Nitrofurantoin, Linezolid, Posizolid, Radezolid, Torezolid, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, Amoxicillin/clavulanate, Ampicillin/sulbactam, Piperacillin/tazobactam, Ticarcillin/clavulanate, Bacitracin, Colistin, Polymyxin B, Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim-Sulfamethoxazole, Sulfonamidochrysoidine, Demeclocycline, Doxycycline, Minocycline, Oxytetracycline, Tetracycline, Clofazimine, Dapsone, Capreomycin, Cycloserine, Ethambutol, Ethionamide, Isoniazid, Pyrazinamide, Rifampicin, Rifabutin, Rifapentine, Streptomycin, Arsphenamine, Chloramphenicol, Fosfomycin, Fusidic acid, Metronidazole, Mupirocin, Platensimycin, Quinupristin/Dalfopristin, Thiamphenicol, Tigecycline, Tinidazole, and Trimethoprim;

Anti-viral agents: asunaprevir, acyclovir, acyclovir, adefovir, amantadine, amprenavir, ampligen, arbidol, atazanavir, atripla, bacavir, boceprevir, cidofovir, combivir, complera, daclatasvir, darunavir, delavirdine, didanosine, docosanol, dolutegravir, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, neuraminidase blocking agents, oseltamivir, peginterferon alfa-2a, penciclovir, peramivir, pleconaril, podofilox, podophyllin, podophyllotoxin, raltegravir, monoclonal antibody respigams, ribavirin, inhaled rhibovirons, rimantadine, ritonavir, pyrimidine, saquinavir, stavudine, stribild, tenofovir, tenofovir disoproxil, tenofovir alafenamide fumarate (TAF), tipranavir, trifluridine, trizivir, tromantadine, truvada, valaciclovir, valganciclovir, vicriviroc, vidarabine, viperin, viramidine, zalcitabine, zanamivir, zidovudine, or salts and combinations thereof;

Anti-fungal agent/anti yeast agents: imidazoles and triazoles, polyene macrolide antibiotics, griseofulvin, amphotericin B, and flucytosine. Antiparasites include heavy metals, antimalarial quinolines, folate antagonists, nitroimidazoles, benzimidazoles, avermectins, praxiquantel, ornithine decarboxylase inhbitors, phenols (e.g., bithionol, niclosamide); synthetic alkaloid (e.g., dehydroemetine); piperazines (e.g., diethylcarbamazine); acetanilide (e.g., diloxanide furonate); halogenated quinolines (e.g., iodoquinol (diiodohydroxyquin)); nitrofurans (e.g., nifurtimox); diamidines (e.g., pentamidine); tetrahydropyrimidine (e.g., pyrantel pamoate); or sulfated naphthylamine (e.g., suramin) .and Anti-protozoal agents: Eflornithine, Furazolidone, Melarsoprol, Metronidazole, Ornidazole, Paromomycin sulfate, Pentamidine, Pyrimethamine, Tinidazole.

Other anti-infective agents may be without limitation Difloxacin Hydrochloride; Lauryl Isoquinolinium Bromide; Moxalactam Disodium; Ornidazole; Pentisomicin; Sarafloxacin Hydrochloride; Protease inhibitors of HIV and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); Ciprofloxacin (Cipro); Aminacrine Hydrochloride; Benzethonium Chloride: Bithionolate Sodium; Bromchlorenone; Carbamide Peroxide; Cetalkonium Chloride; Cetylpyridinium Chloride: Chlorhexidine Hydrochloride; Clioquinol; Domiphen Bromide; Fenticlor; Fludazonium Chloride; Fuchsin, Basic; Furazolidone; Gentian Violet; Halquinols; Hexachlorophene: Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofurazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal; or Troclosene Potassium.

By contrast, a subject positively identified as having non-infectious joint inflammation may be exposed to vasoactive compounds, steroids, non-steroidal anti-inflammatories, anti-tumor necrosis factor agents, recombinant protein C and combinations thereof. In representative embodiments in which non-infectious joint inflammation is diagnosed or infectious joint inflammation is ruled out, the subject is not exposed to anti-microbial agents such as antibiotics.

Typically, the therapeutic agents will be administered in pharmaceutical (or veterinary) compositions together with a pharmaceutically acceptable carrier and in an effective amount to achieve their intended purpose. The dose of active compounds administered to a subject should be sufficient to achieve a beneficial response in the subject over time such as a reduction in, or relief from, the symptoms of the type of joint inflammation. The quantity of the pharmaceutically active compounds(s) to be administered may depend on the subject to be treated inclusive of the age, sex, weight and general health condition thereof. In this regard, precise amounts of the active compound(s) for administration will depend on the judgment of the practitioner. In determining the effective amount of the active compound(s) to be administered in the treatment or prevention of infectious joint inflammation or non-infectious joint inflammation, the medical practitioner or veterinarian may evaluate severity of any symptom or clinical sign associated with the presence of infectious or non-infectious joint inflammation or degree of infectious or non-infectious joint inflammation including, joint pain, joint stiffness, tenderness, swelling, warmth, patient global health assessment, cell counts (e.g., white blood cell counts for example in serum and/or in synovial fluid), erythrocyte sedimentation rate (ESR), C-reactive protein (CRP) levels, blood pressure anomaly, tachycardia, tachypnea fever, chills, vomiting, diarrhea, skin rash, headaches, confusion, muscle aches, seizures. In any event, those of skill in the art may readily determine suitable dosages of the therapeutic agents and suitable treatment regimens without undue experimentation.

The therapeutic agents may be administered in concert with adjunctive (palliative) therapies to increase oxygen supply to major organs, increase blood flow to major organs and/or to reduce the inflammatory response. Illustrative examples of such adjunctive therapies include non-steroidal-anti-inflammatory drugs (NSAIDs), intravenous saline and oxygen.

5. Device Embodiments

Also contemplated herein are embodiments in which a disclosed representative indicator-determining method is implemented using one or more processing devices. In representative embodiments of this type, the method that is implemented by the processing device(s) determines an indicator used in assessing a likelihood of a subject having a presence or absence infectious joint inflammation or non-infectious joint inflammation, wherein the method comprises: (1) determining a biomarker value for at least one joint inflammation biomarker (e.g., 1, 2, 3, 4, 5, 6, 7, 8, 9, 10, 11, 12 or more biomarkers) disclosed herein in a sample obtained from a site of inflammation associated with the joint; (2) determining the indicator using the biomarker value(s); (3) retrieving previously determined indicator references from a database, the indicator references being determined based on indicators determined from a reference population consisting of individuals diagnosed with infectious joint inflammation or non-infectious joint inflammation; (4) comparing the indicator to the indicator references to thereby determine a probability indicative of the subject having or not having infectious joint inflammation or non-infectious joint inflammation; and (5) generating a representation of the probability, the representation being displayed to a user to allow the user to assess the likelihood of a subject having infectious joint inflammation or non-infectious joint inflammation.

In specific embodiments, an apparatus is provided for determining the likelihood of a subject having infectious joint inflammation or non-infectious joint inflammation. The apparatus typically includes at least one electronic processing device that:

> determines a biomarker value for at least one joint inflammation biomarker (e.g., 1, 2, 3, 4, 5, 6, 7, 8, 9, 10, 11, 12 or more biomarkers) disclosed herein in a sample obtained from a site of inflammation associated with the joint; and
>
> determines the indicator using the derived biomarker value(s).

The apparatus may further include any one or more of:
(A) a sampling device that obtains a sample taken from a subject, the sample including at least one joint inflammation biomarker (e.g., 1, 2, 3, 4, 5, 6, 7, 8, 9, 10, 11, 12 or more biomarkers) disclosed herein;
(B) a measuring device that quantifies for each of the joint inflammation biomarkers a corresponding a biomarker value;
(C) at least one processing device that:
(i) receives the biomarker value(s) from the measuring device;
(ii) determines an indicator that is indicative of the presence or absence of infectious joint inflammation or non-infectious joint inflammation using the biomarker values optionally in combination with one or more clinical parameters of the subject;
(iii) compares the indicator to at least one indicator reference;
(iv) determines a likelihood of the subject having or not having infectious joint inflammation or non-infectious joint inflammation using the results of the comparison; and
(v) generates a representation of the indicator and the likelihood for display to a user.

In some embodiments, the apparatus comprises a processor configured to execute computer readable media instructions (e.g., a computer program or software application, e.g., a machine learning system, to receive the biomarker values from the evaluation of biomarkers in a sample and, in combination with other risk factors (e.g., medical history of the patient, publically available sources of information pertaining to a risk of developing infectious joint inflammation or non-infectious joint inflammation, etc.) may determine a master composite score and compare it to a grouping of stratified cohort population comprising multiple risk categories (e.g., a risk categorization table) and provide a risk score. Methods and techniques for determining a master composite score and a risk score are known in the art.

The apparatus can take any of a variety of forms, for example, a handheld device, a tablet, or any other type of computer or electronic device. The apparatus may also comprise a processor configured to execute instructions (e.g., a computer software product, an application for a handheld device, a handheld device configured to perform the method, a world-wide-web (WWW) page or other cloud or network accessible location, or any computing device. In other embodiments, the apparatus may include a handheld device, a tablet, or any other type of computer or electronic device for accessing a machine learning system provided as a software as a service (SaaS) deployment. Accordingly, the correlation may be displayed as a graphical representation, which, in some embodiments, is stored in a database or memory, such as a random access memory, read-only memory, disk, virtual memory, etc. Other suitable representations, or exemplifications known in the art may also be used.

The apparatus may further comprise a storage means for storing the correlation, an input means, and a display means for displaying the status of the subject in terms of the particular medical condition (e.g., infectious joint inflammation or non-infectious joint inflammation). The storage means can be, for example, random access memory, read-only memory, a cache, a buffer, a disk, virtual memory, or a database. The input means can be, for example, a keypad, a keyboard, stored data, a touch screen, a voice-activated system, a downloadable program, downloadable data, a digital interface, a hand-held device, or an infrared signal device. The display means can be, for example, a computer monitor, a cathode ray tube (CRT), a digital screen, a light-emitting diode (LED), a liquid crystal display (LCD), an X-ray, a compressed digitized image, a video image, or a hand-held device. The apparatus can further comprise or communicate with a database, wherein the database stores the correlation of factors and is accessible to the user.

In certain embodiments, the apparatus is a computing device, for example, in the form of a computer or hand-held device that includes a processing unit, memory, and storage. The computing device can include, or have access to a computing environment that comprises a variety of computer-readable media, such as volatile memory and non-volatile memory, removable storage and/or non-removable storage. Computer storage includes, for example, RAM, ROM, EPROM & EEPROM, flash memory or other memory technologies, CD ROM, Digital Versatile Disks (DVD) or other optical disk storage, magnetic cassettes, magnetic tape, magnetic disk storage or other magnetic storage devices, or other medium known in the art to be capable of storing computer-readable instructions. The computing device can also include or have access to a computing environment that comprises input, output, and/or a communication connection. The input can be one or several devices, such as a keyboard, mouse, touch screen, or stylus. The output can also be one or several devices, such as a video display, a printer, an audio output device, a touch stimulation output device, or a screen reading output device. If desired, the computing device can be configured to operate in a networked environment using a communication connection to connect to one or more remote computers. The communication connection can be, for example, a Local Area Network (LAN), a Wide Area Network (WAN) or other networks and can operate over the cloud, a wired network, wireless radio frequency network, and/or an infrared network.

EMBODIMENTS OF THE PRESENT DISCLOSURE

1. A method for determining an indicator used in assessing a likelihood that a type of inflammation is present or absent in a joint of a subject, wherein the type of inflammation is selected from infectious inflammation and non-infectious inflammation, the method comprising, consisting or consisting essentially of:

(1) determining a biomarker value for at least one biomarker (e.g., 1, 2, 3, 4, 5, 6, 7, 8, 9, 10, 11, 12, 13, 14, 15, 16 or more biomarkers) in a sample obtained from a site of inflammation associated with the joint, wherein a respective biomarker value is indicative of a level of a corresponding biomarker in the sample, wherein the at least one biomarker is selected from a first panel of biomarkers comprising, consisting or consisting essentially of ACO2, AP3M1, ATG4B, C5orf15, CANX, CDKN1A, CSNK1D, CWC27, CXCL8, DTNBP1, DUSP1, EIF2S1, EMP1, ERP44, FCGR3B, FFAR2, FPR1, FYB1, GBP1, H3-3B, HNRNPAB, IARS2, IPO8, IRF2, KCTD2, KCTD3, KLF13, KLHL12, LARP4, LMNA, MCL1, MLLT6, MOCS3, MRPL20, MRPL37, MXD1, MYO1F, NAGA, NAMPT, NINJ1, NUP58, PARP14, PIK3AP1, PIK3R5, PIP4K2B, PKN1, PLEC, PLXDC2, POLG2, POLR2G, PPIL2, PPP5C, PRPF19, PSMC3, RILPL2, RNASEL, RNF26, SEC24B, SLC26A6, SNIP1, SNRPF, SP1, SP2, STX11, SUSD6, TBK1, TNFRSF1B, TTYH3, TWF2, VPS4B, VPS51, WIPF2 and ZZEF1; and (2) determining the indicator using the biomarker value(s), wherein the indicator distinguishes between a likelihood that infectious inflammation is present or absent in the joint of the subject and a likelihood that non-infectious inflammation is present or absent in the joint of the subject.

2. The method of embodiment 1, wherein biomarker values are obtained for a plurality of biomarkers, wherein the plurality of biomarkers is selected from the first panel of biomarkers and optionally from a second panel of biomarkers comprising API5, AQP9, ATIC, CISH, CLIC4, CSF2RB, CSF3R, DUSP5, ETV6, GADD45B, GRINA, HCK, HLA-E, IER3, IL1B, IL1RN, IMMT, LILRB3, LRPPRC, LYN, NFKBIA, OSM, PDE4B, PI3, PLAUR, PLEK, PPIF, SEMA4D, STARD7, TNFAIP2, TNFAIP3 and ZFP36.

3. The method of embodiment 1 or embodiment 2, wherein biomarker values are determined for at least two biomarkers.

4. The method of embodiment 1 or embodiment 2, wherein biomarker values are determined for at least three biomarkers.

5. The method of embodiment 1 or embodiment 2, wherein biomarker values are determined for at least four biomarkers.

6. The method of embodiment 1 or embodiment 2, wherein biomarker values are determined for at least five biomarkers.

7. The method of embodiment 1 or embodiment 2, wherein biomarker values are determined for at least six biomarkers.

8. The method of embodiment 1 or embodiment 2, wherein biomarker values are determined for at least seven biomarkers.

9. The method of embodiment 1 or embodiment 2, wherein biomarker values are determined for at least eight biomarkers.

10. The method of any one of embodiments 1 to 9, wherein a biomarker value is obtained for ACO2, and the indicator is determined using that biomarker value.

11. The method of any one of embodiments 1 to 10, wherein a biomarker value is obtained for AP3M1.

12. The method of any one of embodiments 2 to 11, wherein a biomarker value is obtained for API5.

13. The method of any one of embodiments 1 to 12, wherein a biomarker value is obtained for ATG4B.

14. The method of any one of embodiments 1 to 13, wherein a biomarker value is obtained for C5orf15.

15. The method of any one of embodiments 1 to 14, wherein a biomarker value is obtained for CANX.

16. The method of any one of embodiments 2 to 15, wherein a biomarker value is obtained for CLIC4.

17. The method of any one of embodiments 2 to 16, wherein a biomarker value is obtained for CSF2RB, ETV6, FFAR2, FYB1, HCK, HLA-E, IRF2, LILRB3, PDE4B, SEMA4D, STX11 or TNFAIP2.

18. The method of any one of embodiments 1 to 17, wherein a biomarker value is obtained for CSNK1D.

19. The method of any one of embodiments 1 to 18, wherein a biomarker value is obtained for CWC27.

20. The method of any one of embodiments 1 to 19, wherein a biomarker value is obtained for DTNBP1.

21. The method of any one of embodiments 2 to 20, wherein a biomarker value is obtained for DUSP5, CDKN1A, CISH or MLLT6.

22. The method of any one of embodiments 1 to 21, wherein a biomarker value is obtained for EIF2S1.

23. The method of any one of embodiments 1 to 22, wherein a biomarker value is obtained for ERP44.

24. The method of any one of embodiments 1 to 23, wherein a biomarker value is obtained for GBP1.

25. The method of any one of embodiments 1 to 24, wherein a biomarker value is obtained for IARS2.

26. The method of any one of embodiments 1 to 24, wherein a biomarker value is obtained for IPO8.

27. The method of any one of embodiments 2 to 26, wherein a biomarker value is obtained for IMMT.

28. The method of any one of embodiments 1 to 27, wherein a biomarker value is obtained for KLF13.

29. The method of any one of embodiments 1 to 28, wherein a biomarker value is obtained for LARP4.

30. The method of any one of embodiments 2 to 29, wherein a biomarker value is obtained for LRPPRC.

31. The method of any one of embodiments 1 to 30, wherein a biomarker value is obtained for MOCS3.

32. The method of any one of embodiments 1 to 31, wherein a biomarker value is obtained for MRPL20.

33. The method of any one of embodiments 1 to 32, wherein a biomarker value is obtained for MXD1, AQP9, CSF3R, DUSP1, FCGR3B, FPR1, H3-3B, LYN, MCL1 or NAMPT.

34. The method of any one of embodiments 1 to 33, wherein a biomarker value is obtained for MYO1F.

35. The method of any one of embodiments 1 to 34, wherein a biomarker value is obtained for NAGA.

36. The method of any one of embodiments 2 to 35, wherein a biomarker value is obtained for NFKBIA, GADD45B, GRINA, NINJ1, PI3, PIK3AP1, PLAUR, PLEK or TNFAIP3.

37. The method of any one of embodiments 1 to 36, wherein a biomarker value is obtained for NUP58 or CXCL8.

38. The method of any one of embodiments 1 to 37, wherein a biomarker value is obtained for PARP14.

39. The method of any one of embodiments 1 to 38, wherein a biomarker value is obtained for PIK3R5.

40. The method of any one of embodiments 1 to 39, wherein a biomarker value is obtained for PIP4K2B.

41. The method of any one of embodiments 1 to 40, wherein a biomarker value is obtained for PKN1.

42. The method of any one of embodiments 1 to 41, wherein a biomarker value is obtained for PLEC, EMP1 or LMNA.

43. The method of any one of embodiments 1 to 42, wherein a biomarker value is obtained for PLXDC2.

44. The method of any one of embodiments 1 to 43, wherein a biomarker value is obtained for POLG2.

45. The method of any one of embodiments 1 to 44, wherein a biomarker value is obtained for POLR2G.

46. The method of any one of embodiments 2 to 45, wherein a biomarker value is obtained for PPIF, IER3, IL1B, IL1RN, OSM or ZFP36.

47. The method of any one of embodiments 1 to 46, wherein a biomarker value is obtained for PPIL2.

48. The method of any one of embodiments 1 to 47, wherein a biomarker value is obtained for PPP5C.

49. The method of any one of embodiments 1 to 48, wherein a biomarker value is obtained for PSMC3.

50. The method of any one of embodiments 1 to 49, wherein a biomarker value is obtained for RILPL2.

51. The method of any one of embodiments 1 to 50, wherein a biomarker value is obtained for RNASEL.

52. The method of any one of embodiments 1 to 51, wherein a biomarker value is obtained for RNF26.

53. The method of any one of embodiments 1 to 52, wherein a biomarker value is obtained for SEC24B.

54. The method of any one of embodiments 1 to 53, wherein a biomarker value is obtained for SLC26A6.

55. The method of any one of embodiments 1 to 54, wherein a biomarker value is obtained for SNIP1.

56. The method of any one of embodiments 1 to 55, wherein a biomarker value is obtained for SP1.

57. The method of any one of embodiments 1 to 56, wherein a biomarker value is obtained for SP2.

58. The method of any one of embodiments 2 to 57, wherein a biomarker value is obtained for STARD7.

59. The method of any one of embodiments 1 to 58, wherein a biomarker value is obtained for SUSD6.

60. T The method of any one of embodiments 1 to 59, wherein a biomarker value is obtained for BK1.

61. The method of any one of embodiments 1 to 60, wherein a biomarker value is obtained for TNFRSF1B.

62. The method of any one of embodiments 1 to 61, wherein a biomarker value is obtained for TTYH3.

63. The method of any one of embodiments 1 to 62, wherein a biomarker value is obtained for TWF2.

64. The method of any one of embodiments 1 to 63, wherein a biomarker value is obtained for VPS4B.

65. The method of any one of embodiments 1 to 64, wherein a biomarker value is obtained for WIPF2.

66. The method of any one of embodiments 1 to 65, wherein a biomarker value is obtained for ZZEF1

67. The method of any one of embodiments 1 to 66, wherein biomarker values are determined for a first biomarker and a second biomarker, wherein the first biomarker is selected from a first set of biomarkers that are expressed at a higher level in infectious inflammation than in non-infectious inflammation, and wherein the second biomarker is selected from a second set of biomarkers that are expressed at a lower level in infectious inflammation than in non-infectious inflammation, and/or from a third set of biomarkers that improve the discrimination performance of the first biomarker, wherein the first set of biomarkers comprises, consists or consists essentially of AQP9, C5orf15, CANX, CDKN1A, CISH, CLIC4, CSF2RB, CSF3R, CXCL8, DTNBP1, DUSP1, DUSP5, ERP44, ETV6, FCGR3B, FFAR2, FPR1, FYB1, GADD45B, GBP1, GRINA, H3-3B, HCK, HLA-E, IRF2, LILRB3, LYN, MCL1, MLLT6, MXD1, NAMPT, NFKBIA, NINJ1, NUP58, PARP14, PDE4B, PI3, PIK3AP1, PIK3R5, PLAUR, PLEK, RILPL2, RNASEL, SEMA4D, SP2, STX11, SUSD6, TBK1, TNFAIP2, TNFAIP3, TNFRSF1B and WIPF2, wherein the second set of biomarkers comprises, consists or consists essentially of ACO2, AP3M1, API5, ATIC, CWC27, EIF2S1, EMP1, HNRNPAB, IARS2, KLF13, LARP4, LMNA, LRPPRC, MOCS3, MRPL20, MRPL37, NAGA, PIP4K2B, PKN1, PLEC, PLXDC2, PPIL2, PPP5C, PRPF19, RNF26, STARD7, TTYH3, TWF2, VPS51 and ZZEF1, and wherein the third set of biomarkers comprises, consists or consists essentially of CSNK1D, MYO1F and POLR2G.

68. The method of embodiment 67, wherein the first and second biomarkers are selected from TABLE A:

TABLE A

| First Biomarker | Second Biomarker |
| --- | --- |
| MXD1 | MYO1F |
| SP2 | KLF13 |
| DUSP5 | PLEC |

TABLE A-continued

| First Biomarker | Second Biomarker |
|---|---|
| CSF2RB | MYO1F |
| DUSP5 | PRPF19 |
| ERP44 | AP3M1 |
| NFKBIA | MOCS3 |
| CLIC4 | PLEC |
| DUSP5 | VPS51 |
| DUSP5 | STARD7 |
| ERP44 | CWC27 |
| NFKBIA | POLR2G |
| DUSP5 | HNRNPAB |
| DUSP5 | ACO2 |
| DUSP5 | PPP5C |
| DUSP5 | ATIC |
| DUSP5 | PIP4K2B |
| DUSP5 | TTYH3 |
| DUSP5 | MRPL37 |
| NFKBIA | RNF26 |

69. The method of any one of embodiments 1 to 66, biomarker values are determined for a first biomarker, a second biomarker, a third biomarker and optionally a fourth biomarker, wherein the first and second biomarkers are selected from a first set of biomarkers that are expressed at a higher level in infectious inflammation than in non-infectious inflammation, and wherein the third and optional fourth biomarkers are selected from a second set of biomarkers that are expressed at a lower level in infectious inflammation than in non-infectious inflammation, and/or a third set of biomarkers that improve the discrimination performance of the first and/or second biomarkers, wherein the first set of biomarkers comprises, consists or consists essentially of AQP9, C5orf15, CANX, CDKN1A, CISH, CLIC4, CSF2RB, CSF3R, CXCL8, DTNBP1, DUSP1, DUSP5, ERP44, ETV6, FCGR3B, FFAR2, FPR1, FYB1, GADD45B, GBP1, GRINA, H3-3B, HCK, HLA-E, IRF2, LILRB3, LYN, MCL1, MLLT6, MXD1, NAMPT, NFKBIA, NINJ1, NUP58, PARP14, PDE4B, PI3, PIK3AP1, PIK3R5, PLAUR, PLEK, RILPL2, RNASEL, SEMA4D, SNIP1, SP1, SP2, STX11, SUSD6, TBK1, TNFAIP2, TNFAIP3, TNFRSF1B and WIPF2, wherein the second set of biomarkers comprises, consists or consists essentially of ACO2, AP3M1, API5, ATIC, CWC27, EIF2S1, EMP1, IMMT, KLF13, LARP4, LMNA, LRPPRC, MOCS3, MRPL20, MRPL37, NAGA, PIP4K2B, PKN1, PLEC, PLXDC2, PPIL2, PPP5C, PRPF19, PSMC3, RNF26, SNRPF, STARD7, TTYH3, TWF2 and VPS51, and wherein the third set of biomarkers comprises, consists or consists essentially of ATG4B, CSNK1D, IPO8, KCTD2, MYO1F, POLG2, POLR2G and ZZEF1.

70. The method of embodiment 69, wherein the first and second biomarkers, and one or both of the third and fourth biomarkers are selected from TABLE B:

TABLE B

| First Biomarker | Second Biomarker | Third Biomarker | Fourth Biomarker |
|---|---|---|---|
| CLIC4 | CSF2RB | POLR2G | — |
| CLIC4 | CSF2RB | MYO1F | PPP5C |
| CLIC4 | NUP58 | EIF2S1 | — |
| CLIC4 | DUSP5 | PLEC | PSMC3 |
| CLIC4 | NUP58 | API5 | — |
| CLIC4 | DUSP5 | PLEC | RNF26 |
| CLIC4 | CSF2RB | CSNK1D | PPP5C |

TABLE B-continued

| First Biomarker | Second Biomarker | Third Biomarker | Fourth Biomarker |
|---|---|---|---|
| CLIC4 | NUP58 | AP3M1 | — |
| CLIC4 | MXD1 | KCTD2 | |
| CLIC4 | MXD1 | MYO1F | PPP5C |
| CLIC4 | DUSP5 | PLEC | SNRPF |
| CLIC4 | CSF2RB | KCTD2 | |
| CLIC4 | CSF2RB | IPO8 | |
| CLIC4 | DUSP5 | EIF2S1 | PLEC |
| CLIC4 | DUSP5 | PLEC | PPP5C |
| CLIC4 | CSF2RB | POLR2G | PPP5C |
| CLIC4 | TNFRSF1B | CSNK1D | PPP5C |
| CLIC4 | CSF2RB | KCTD2 | PPP5C |
| CLIC4 | RILPL2 | MOCS3 | PPP5C |
| CLIC4 | NUP58 | POLR2G | TTYH3 |

71. The method of any one of embodiments 1 to 66, wherein biomarker values are determined for a first biomarker, a second biomarker, a third biomarker, optionally a fourth biomarker, a fifth biomarker, a sixth biomarker and optionally one or both of a seventh biomarker and an eighth biomarker, wherein the first biomarker, second biomarker, third biomarker and optional fourth biomarker are selected from a first set of biomarkers that are expressed at a higher level in infectious inflammation than in non-infectious inflammation, and wherein the fifth biomarker, sixth biomarker and optional seventh and eighth biomarkers are selected from a second set of biomarkers that are expressed at a lower level in infectious inflammation than in non-infectious inflammation, and/or from a third set of biomarkers that improve the discrimination performance of the first biomarker, second biomarker, third biomarker and optional fourth biomarker, wherein the first set of biomarkers comprises, consists or consists essentially of AQP9, C5orf15, CANX, CDKN1A, CISH, CLIC4, CSF2RB, CSF3R, CXCL8, DTNBP1, DUSP1, DUSP5, EMP1, ERP44, ETV6, FCGR3B, FFAR2, FPR1, FYB1, GADD45B, GRINA, H3-3B, HCK, HLA-E, IER3, IL1B, IL1RN, IRF2, LILRB3, LMNA, LYN, MCL1, MLLT6, MXD1, NAMPT, NFKBIA, NINJ1, NUP58, OSM, PDE4B, PI3, PIK3AP1, PLAUR, PLEK, PPIF, RILPL2, RNASEL, SEMA4D, SNIP1, SP1, SP2, STX11, SUSD6, TNFAIP2, TNFAIP3, TNFRSF1B, WIPF2 and ZFP36 wherein the second set of biomarkers comprises, consists or consists essentially of ACO2, AP3M1, API5, EIF2S1, IMMT, KCTD3, KLF13, MOCS3, MRPL20, PKN1, PLEC, PPP5C, PSMC3, RNF26, SNRPF, STARD7 and TTYH3, and wherein the third set of biomarkers comprises, consists or consists essentially of ATG4B, CSNK1D, IPO8, KLHL12, MYO1F, POLG2, POLR2G, SEC24B, SLC26A6, VPS4B and ZZEF1.

72. The method of embodiment 71, wherein the first biomarker, second biomarker, third biomarker, optional fourth biomarker, fifth biomarker, sixth biomarker and optional seventh and eighth biomarkers are selected from TABLE C:

TABLE C

| First Biomarker | Second Biomarker | Third Biomarker | Fourth Biomarker | Fifth Biomarker | Sixth Biomarker | Seventh Biomarker | Eighth Biomarker |
|---|---|---|---|---|---|---|---|
| CLIC4 | CSF2RB | NUP58 | | IPO8 | POLR2G | | |
| CLIC4 | CSF2RB | NUP58 | | POLR2G | PPP5C | VPS4B | |
| CLIC4 | DUSP5 | SP2 | | PKN1 | PLEC | PPP5C | RNF26 |
| CLIC4 | NUP58 | SP2 | | PKN1 | PLEC | PPP5C | VPS4B |
| CLIC4 | CSF2RB | DUSP5 | | PLEC | POLR2G | PSMC3 | |
| CLIC4 | CSF2RB | DUSP5 | RNASEL | ATG4B | KLF13 | POLR2G | |
| CLIC4 | CSF2RB | NUP58 | SNIP1 | POLR2G | PPIL2 | VPS4B | |
| CLIC4 | CSF2RB | DUSP5 | | POLR2G | PPP5C | RNF26 | |
| CLIC4 | NUP58 | SP2 | | PKN1 | PLEC | PPP5C | SEC24B |
| CLIC4 | CSF2RB | DUSP5 | | MYO1F | PLEC | PPP5C | RNF26 |
| CLIC4 | PPIF | SP2 | | PKN1 | PLEC | PPP5C | SLC26A6 |
| CLIC4 | CSF2RB | NUP58 | | KLHL12 | POLR2G | PPP5C | |
| CLIC4 | DUSP5 | SP2 | | PKN1 | PLEC | PPP5C | PSMC3 |
| CLIC4 | CSF2RB | DUSP5 | | CSNK1D | PPP5C | PPP5C | RNF26 |
| CLIC4 | CSF2RB | DUSP5 | | AP3M1 | PPP5C | RNF26 | |
| CLIC4 | CSF2RB | DUSP5 | | PLXDC2 | PPP5C | RNF26 | |
| CLIC4 | DUSP5 | SP2 | | KCTD3 | PKN1 | PLEC | PPP5C |
| CLIC4 | NUP58 | SP2 | | PKN1 | PLEC | POLR2G | |
| CLIC4 | DUSP5 | NUP58 | | PLEC | PPP5C | RNF26 | SEC24B |
| CLIC4 | DUSP5 | SP2 | | KLF13 | PLEC | PPP5C | RNF26 |

73. The method of any one of embodiments 68, 70 and 72, wherein CSF2RB is substituted with ETV6, FFAR2, FYB1, HCK, HLA-E, IRF2, LILRB3, PDE4B, SEMA4D, STX11 or TNFAIP2.

74. The method of any one of embodiments 68, 70 and 72, wherein DUSP5 is substituted with CDKN1A, CISH or MLLT6.

75. The method of any one of embodiments 68, 70 and 72, wherein NUP58 is substituted with CXCL8.

76. The method of any one of embodiments 68, 70 and 72, wherein MXD1 is substituted with AQP9, CSF3R, DUSP1, FCGR3B, FPR1, H3-3B, LYN, MCL1 or NAMPT.

77. The method of any one of embodiments 68, 70 and 72, wherein NFKBIA is substituted with GADD45B, GRINA, NINJ1, PI3, PIK3AP1, PLAUR, PLEK or TNFAIP3.

78. The method of any one of embodiments 68, 70 and 72, wherein PLEC is substituted EMP1 or LMNA.

79. The method of embodiment 72, wherein PPIF is substituted with IER3, IL1B, IL1RN, OSM or ZFP36.

80. The method of any one of embodiments 1 to 79, further comprising applying a function to biomarker values to yield at least one functionalized biomarker value and determining the indicator using the at least one functionalized biomarker value.

81. The method of embodiment 80, wherein the function includes at least one of: (a) multiplying biomarker values; (b) dividing biomarker values; (c) adding biomarker values; (d) subtracting biomarker values; (e) a weighted sum of biomarker values; (f) a log sum of biomarker values; (g) a geometric mean of biomarker values; and (h) a sigmoidal function of biomarker values.

82. The method of any one of embodiments 1 to 81, further comprising combining the biomarker values to provide a composite score and determining the indicator using the composite score.

83. The method of embodiment 82, wherein the biomarker values are combined by adding, multiplying, subtracting, and/or dividing biomarker values.

84. The method of any one of embodiments 1 to 83, wherein individual biomarker values are representative of a measured amount or concentration of a corresponding biomarker in the sample.

85. The method of any one of embodiments 1 to 83, wherein individual biomarker values are a logarithmic representation of a measured amount or concentration of a corresponding biomarker in the sample.

86. The method of embodiment 85, wherein biomarker values are determined for a first biomarker and a second biomarker according to TABLE A of any one of embodiments 68, and 73 to 76, and the method further comprises subtracting the biomarker value for the second biomarker from the biomarker value for the first biomarker to provide a composite score, and determining the indicator using the composite score.

87. The method of embodiment 85, wherein biomarker values are determined for a first biomarker, second biomarker, third biomarker and optional fourth biomarker according to TABLE B of any one of embodiments 70, and 73 to 76, and the method further comprises adding the biomarker values for the first biomarker and the second biomarker to provide a first summed biomarker value, adding the biomarker values for the third biomarker and fourth biomarker, if present, to provide a second summed biomarker value, subtracting the second summed biomarker value from the first summed biomarker value to provide a composite score, and determining the indicator using the composite score.

88. The method of embodiment 85, wherein biomarker values are determined for the first biomarker, second biomarker, third biomarker, optional fourth biomarker, fifth biomarker, sixth biomarker and optional seventh and eighth biomarkers according to TABLE C of any one of embodiments 72 to 76, and the method further comprises adding the biomarker values for the first biomarker, second biomarker, third biomarker and optional fourth biomarker, if present, to provide a first summed biomarker value, adding the biomarker values for the fifth biomarker, sixth biomarker and optional seventh and eighth biomarkers, if present, to provide a second summed biomarker value, subtracting the second summed biomarker value from the first summed biomarker value to provide a composite score, and determining the indicator using the composite score.

89. The method of embodiment 88, wherein the addition of the biomarker values that yields the first summed biomarker value comprises twice adding the biomarker value for one or more of the first biomarker, second biomarker, third biomarker and optional fourth biomarker.

90. The method of embodiment 88, wherein the addition of the biomarker values that yields the first summed biomarker value comprises twice adding the biomarker value for one of the first biomarker, second biomarker, third biomarker and optional fourth biomarker, which has the strongest discrimination performance.

91. The method of any one of embodiments 88 to 90, wherein the composite score is determined using one of the following formulas:

$$[CLIC4 + CLIC4 + CSF2RB + NUP58] - [IPO8 + POLR2G]$$

$$[CLIC4 + CLIC4 + CSF2RB + NUP58] - [POLR2G + PPP5C + VPS4B]$$

$$[CLIC4 + CLIC4 + DUSP5 + SP2] - [PKN1 + PLEC + PPP5C + RNF26]$$

$$[CLIC4 + CLIC4 + NUP58 + SP2] - [PKN1 + PLEC + PPP5C + VPS4B]$$

$$[CLIC4 + CLIC4 + CSF2RB + DUSP5] - [PLEC + POLR2G + PSMC3]$$

$$[CLIC4 + CSF2RB + DUSP5 + RNASEL] - [ATG4B + KLF13 + POLR2G]$$

$$[CLIC4 + CSF2RB + NUP58 + SNIP1] - [POLR2G + PPIL2 + VPS4B]$$

$$[CLIC4 + CLIC4 + CSF2RB + DUSP5] - [POLR2G + PPP5C + RNF26]$$

$$[CLIC4 + CLIC4 + NUP58 + SP2] - [PKN1 + PLEC + PPP5C + SEC24B]$$

$$[CLIC4 + CLIC4 + CSF2RB + DUSP5] -$$
$$[MYO1F + PLEC + PPP5C + RNF26]$$

$$[CLIC4 + CLIC4 + PPIF + SP2] - [PKN1 + PLEC + PPP5C + SLC26A6]$$

$$[CLIC4 + CLIC4 + CSF2RB + NUP58] - [KLHL12 + POLR2G + PPP5C]$$

$$[CLIC4 + CLIC4 + DUSP5 + SP2] - [PKN1 + PLEC + PPP5C + PSMC3]$$

$$[CLIC4 + CLIC4 + CSF2RB + DUSP5] -$$
$$[CSNK1D + PPP5C + PPP5C + RNF26]$$

$$[CLIC4 + CLIC4 + CSF2RB + DUSP5] - [AP3M1 + PPP5C + RNF26]$$

$$[CLIC4 + CLIC4 + CSF2RB + DUSP5] - [PLXDC2 + PPP5C + RNF26]$$

$$[CLIC4 + CLIC4 + DUSP5 + SP2] - [KCTD3 + PKN1 + PLEC + PPP5C]$$

$$[CLIC4 + CLIC4 + NUP58 + SP2] - [PKN1 + PLEC + POLR2G]$$

$$[CLIC4 + CLIC4 + DUSP5 + NUP58] -$$
$$[PLEC + PPP5C + RNF26 + SEC24B]$$

$$[CLIC4 + CLIC4 + DUSP5 + SP2] - [KLF13 + PLEC + PPP5C + RNF26].$$

92. The method of any one of embodiments 1 to 90, comprising determining biomarker values for CDKN1A, CLIC4, CSF2RB, DUSP5, IPO8, NFKBIA, NUP58, POLR2G and PPP5C, optionally in combination with a reference or control biomarker, and determining an indicator indicative of a likelihood that the subject has infectious joint inflammation, or not, using the following algorithm:

$$1 > \{NFKBIA\}/\{CSF2RB\}$$

$$\text{AND } 1 > \{NKFBIA\}/\{NUP58\}$$

-continued $$\text{AND } 2 > \{NFKBIA\}/\{POLR2G\}$$

$$\text{AND } 2 > \{NFKBIA\}/\{DUSP5\}$$

$$\text{AND } 3 > \{NFKBIA\}/\{IPO8\}$$

$$\text{AND } \{NFKBIA\}/\{PPP5C\} > 0.7$$

$$\text{AND } \{NFKBIA\}/\{CDKN1A\} > 3.5$$

$$\text{AND } \{CSF2RB\}/\{CLIC4\} > 0.9$$

$$\text{AND } 1 > \{CSF2RB\}/\{NUP58\}$$

$$\text{AND } \{CSF2RB\}/\{POLR2G\} > 0.5$$

$$\text{AND } \{CSF2RB\}/\{DUSP5\} > 1$$

$$\text{AND } \{CSF2RB\}/\{IPO8\} > 0.9$$

$$\text{AND } \{CSF2RB\}/\{PPP5C\} > 1.5$$

$$\text{AND } 2.5 > \{NUP58\}/\{CSF2RB\}$$

$$\text{AND } \{NUP58\}/\{CLIC4\} > 0.9$$

$$\text{AND } \{NUP58\}/\{POLR2G\} > 1$$

$$\text{AND } \{NUP58\}/\{DUSP5\} > 1.2$$

$$\text{AND } \{NUP58\}/\{IPO8\} > 2$$

$$\text{AND } \{NUP58\}/\{PPP5C\} > 3$$

$$\text{AND } \{NUP58\}/\{CDKN1A\} > 5$$

$$\text{AND } \{NUP58\}/\{NFKBIA\} > 1.3$$

$$\text{AND } \{NUP58\}/\{FBXO28.RNA \text{ ref Low } 1\} > 4.$$

93. The method of any one of embodiments 1 to 90, comprising determining biomarker values for CDKN1A, CLIC4, CSF2RB, DUSP5, IPO8, NFKBIA, NUP58, POLR2G and PPP5C, optionally in combination with a reference or control biomarker, and determining an indicator indicative of a likelihood that the subject has infectious joint inflammation, or not, using the following algorithm:

$$0.75 > \{CLIC4\}/\{CSF2RB\}$$

$$\text{AND } \{CLIC4\}/\{POLR2G\} > 0.5$$

$$\text{AND } \{CLIC4\}/\{DUSP5\} > 0.5$$

$$\text{AND } \{CLIC4\}/\{PPP5C\} > 0.5.$$

94. The method of embodiment 93 or embodiment 94, wherein the algorithm is used for a sample taken from a native joint, or from an artificial or prosthetic joint.

95. The method of any one of embodiments 1 to 94, comprising analyzing the biomarker value(s) or composite score with reference to corresponding reference biomarker value ranges or threshold values, or composite score ranges or threshold values, to determine the indicator.

96. The method of any one of embodiments 1 to 95, wherein the indicator indicates a likelihood of a presence of infectious inflammation if the biomarker value(s) or composite score is indicative of the level of the biomarker(s) in the sample that correlates with an increased likelihood of a presence of infectious inflammation relative to a predetermined reference biomarker value range or cut-off value, and wherein the indicator indicates a likelihood of the presence of non-infectious inflammation if the biomarker value(s) or composite score is indicative of the level of the biomarker(s) in the sample that correlates with an increased likelihood of the presence of non-infectious inflammation relative to a predetermined reference biomarker value range or cut-off value.

97. The method of any one of embodiments 1 to 96, wherein the indicator indicates a likelihood of the absence of infectious inflammation if the biomarker value(s) or composite score is indicative of the level of the biomarker(s) in the sample that correlates with ruling out a presence of infectious inflammation relative to a predetermined reference biomarker value range or cut-off value.

98. The method of any one of embodiments 1 to 97, wherein the joint is selected from a synovial joint, a fibrous joint and a cartilaginous joint.

99. The method of embodiment 98, wherein the synovial joint is a knee joint, wrist joint, shoulder joint, hip joint, elbow joint or ankle joint.

100. The method of embodiment 99, wherein the synovial joint is a knee joint.

101. The method of any one of embodiments 98 to 100, wherein the synovial joint is a native joint.

102. The method of any one of embodiments 98 to 101, wherein the synovial joint is an artificial or prosthetic joint.

103. The method of any one of embodiments 1 to 102, wherein the sample comprises synovial fluid, lymph fluid, joint exudate, joint transudate, or combination thereof.

104. The method of any one of embodiments 1 to 103, wherein the sample comprises leukocytes.

105. The method of any one of embodiments 1 to 104, wherein the subject has at least one clinical sign of inflammation in, or proximal to, the joint.

106. The method of embodiment 105, wherein the inflammation is acute inflammation.

107. The method of embodiment 105 or embodiment 106, wherein the inflammation comprises one or more of redness, increased heat, swelling, pain and loss of function in, or proximal to, the joint.

108. The method of any one of embodiments 1 to 107, wherein the subject has joint pain.

109. An apparatus for determining an indicator used in assessing a likelihood that a type of inflammation is present or absent in a joint of a subject, wherein the type of inflammation is selected from infectious inflammation and non-infectious inflammation, the apparatus comprising at least one electronic processing device that:

determines a biomarker value for at least one biomarker (e.g., 1, 2, 3, 4, 5, 6, 7, 8, 9, 10, 11, 12, 13, 14, 15, 16 or more biomarkers) in a sample obtained from a site of inflammation associated with the joint, wherein a respective biomarker value is indicative of a level of a corresponding biomarker in the sample, wherein the at least one biomarker is selected from a first panel of biomarkers comprising, consisting or consisting essentially of ACO2, AP3M1, ATG4B, C5orf15, CANX, CDKN1A, CSNK1D, CWC27, CXCL8, DTNBP1, DUSP1, EIF2S1, EMP1, ERP44, FCGR3B, FFAR2, FPR1, FYB1, GBP1, H3-3B, HNRNPAB, IARS2, IPO8, IRF2, KCTD2, KCTD3, KLF13, KLHL12, LARP4, LMNA, MCL1, MLLT6, MOCS3, MRPL20, MRPL37, MXD1, MYO1F, NAGA, NAMPT, NINJ1, NUP58, PARP14, PIK3AP1, PIK3R5, PIP4K2B, PKN1, PLEC, PLXDC2, POLG2, POLR2G, PPIL2, PPP5C, PRPF19, PSMC3, RILPL2, RNASEL, RNF26, SEC24B, SLC26A6, SNIP1, SNRPF, SP1, SP2, STX11, SUSD6, TBK1, TNFRSF1B, TTYH3, TWF2, VPS4B, VPS51, WIPF2 and ZZEF1; and determines the indicator using the derived biomarker value(s), wherein the indicator distinguish between a likelihood that infectious inflammation is present or absent in a joint of a subject and a likelihood that non-infectious inflammation is present or absent in the joint of the subject.

110. The apparatus of embodiment 109, wherein the at least one electronic processing device:

determines biomarker values for a plurality of biomarkers, wherein the plurality of biomarkers is selected from the first panel of biomarkers and optionally from a second panel of biomarkers comprising API5, AQP9, ATIC, CISH, CLIC4, CSF2RB, CSF3R, DUSP5, ETV6, GADD45B, GRINA, HCK, HLA-E, IER3, IL1B, IL1RN, IMMT, LILRB3, LRPPRC, LYN, NFKBIA, OSM, PDE4B, PI3, PLAUR, PLEK, PPIF, SEMA4D, STARD7, TNFAIP2, TNFAIP3 and ZFP36.

111. A composition comprising a mixture of a DNA polymerase, synovial fluid leukocyte cDNA from a subject with joint pain and/or at least one clinical sign of inflammation (e.g., acute inflammation) in, or proximal to, the joint, wherein the synovial fluid leukocyte cDNA comprises at least one cDNA (e.g., 1, 2, 3, 4, 5, 6, 7, 8, 9, 10, 11, 12, 13, 14, 15, 16 or more cDNA) selected from a first panel of cDNA biomarkers comprising, consisting or consisting essentially of ACO2, AP3M1, ATG4B, C5orf15, CANX, CDKN1A, CSNK1D, CWC27, CXCL8, DTNBP1, DUSP1, EIF2S1, EMP1, ERP44, FCGR3B, FFAR2, FPR1, FYB1, GBP1, H3-3B, HNRNPAB, IARS2, IPO8, IRF2, KCTD2, KCTD3, KLF13, KLHL12, LARP4, LMNA, MCL1, MLLT6, MOCS3, MRPL20, MRPL37, MXD1, MYO1F, NAGA, NAMPT, NINJ1, NUP58, PARP14, PIK3AP1, PIK3R5, PIP4K2B, PKN1, PLEC, PLXDC2, POLG2, POLR2G, PPIL2, PPP5C, PRPF19, PSMC3, RILPL2, RNASEL, RNF26, SEC24B, SLC26A6, SNIP1, SNRPF, SP1, SP2, STX11, SUSD6, TBK1, TNFRSF1B, TTYH3, TWF2, VPS4B, VPS51, WIPF2 and ZZEF1, and wherein the composition further comprises for the at least one cDNA of the first panel of cDNA biomarkers at least one oligonucleotide primer or probe that hybridizes to the cDNA.

112. The composition of embodiment 111, wherein the synovial fluid leukocyte cDNA comprises at least one cDNA selected (e.g., 1, 2, 3, 4, 5, 6, 7, 8, 9, 10, 11, 12, 13, 14, 15, 16 or more cDNA) from a second panel of cDNA biomarkers comprising API5, AQP9, ATIC, CISH, CLIC4, CSF2RB, CSF3R, DUSP5, ETV6, GADD45B, GRINA, HCK, HLA-E, IER3, IL1B, IL1RN, IMMT, LILRB3, LRPPRC, LYN, NFKBIA, OSM, PDE4B, PI3, PLAUR, PLEK, PPIF, SEMA4D, STARD7, TNFAIP2, TNFAIP3 and ZFP36, and wherein the composition further comprises for the at least one cDNA of the second panel of cDNA biomarkers at least one oligonucleotide primer or probe that hybridizes to the cDNA.

113. The composition of embodiment 111 or embodiment 112, wherein the composition comprises for respective cDNA two oligonucleotide primers that hybridize to opposite complementary strands of the cDNA.

114. The composition of any one of embodiments 111 to 113, wherein the composition comprises for a respective cDNA two pairs of oligonucleotide primers, wherein the oligonucleotide primers of a respective pair hybridize to opposite complementary strands of the cDNA, and wherein the oligonucleotide primers of one pair are nested ("nested oligonucleotide primers") relative the oligonucleotide primers of the other pair.

115. The composition of any one of embodiments 111 to 114, wherein the composition comprises for respective cDNA an oligonucleotide probe that hybridizes to the cDNA or a polynucleotide corresponding thereto (e.g., a polynucleotide product resulting nucleic acid amplification of the cDNA).

116. The composition of embodiment 115, wherein the oligonucleotide probe comprises a heterologous reporter molecule.

117. The composition of embodiment 116, wherein the reporter molecule comprises a fluorescent label.

118. The composition of any one of embodiments 111 to 117, wherein the oligonucleotide probe is a real-time polymerase chain reaction probe.

119. The composition of any one of embodiments 111 to 118, wherein the composition comprises for each of at least 2, 3, 4, 5, 6, 7, 8, 9, 10, 11, 12, 13, 14, 15 or 16 of the cDNAs at least one oligonucleotide primer and/or probe that hybridizes to the cDNA.

120. The composition of any one of embodiments 111 to 118, wherein the composition comprises for each of up to 2, 3, 4, 5, 6, 7, 8, 9, 10, 11, 12, 13, 14, 15 or 16 of the cDNAs at least one oligonucleotide primer and/or probe that hybridizes to the cDNA.

121. The composition of embodiment 119 or embodiment 120, wherein individual cDNAs and their corresponding oligonucleotide primer(s) and/or probe(s) are present in separate reaction vessels.

122. The composition of embodiment 121, wherein two or more (e.g., 2, 3, 4, 5, 6, 7, 8, 9, 10, 11, 12, 13, 14, 15 or 16) cDNAs and their corresponding oligonucleotide primer(s) and/or probe(s) are present in the same reaction vessel.

123. The composition of any one of embodiments 111 to 122, wherein the DNA polymerase is a thermostable DNA polymerase.

124. A device for nucleic acid amplification of synovial fluid leukocyte cDNA, the device comprising a plurality of reaction vessels, individual reaction vessels comprising the composition of any one of embodiments 111 to 123.

125. The device of embodiment 124, consisting of 2 to 100, 2 to 50, 2 to 40, 2 to 30, 2 to 20, 2 to 15, 2 to 12, 2 to 10 or 2 to 8 reaction vessels (and all integer reaction vessels in between).

126. The device of embodiment 124 or embodiment 125, consisting of 2, 3, 4, 5, 6, 7, 8, 9, 10, 11, 12, 13, 14, 15 or 16 reaction vessels.

127. The device of any one of embodiments 124 to 126, wherein one or more reaction vessels are used for single-plex amplification of cDNA.

128. The device of embodiment any one of embodiments 124 to 127, wherein one or more reaction vessels are used for multiplex amplification of cDNA.

129. The device of embodiment 128, wherein the multiplex amplification is 2-plex, 3-plex, 4-plex, 5-plex or 6-plex.

130. A method for inhibiting the development or progression of infectious inflammation or non-infectious inflammation in a subject with joint pain and/or at least one clinical sign of inflammation (e.g., acute inflammation) in, or proximal to, a joint, the method comprising:

(1) exposing the subject to a treatment regimen for infectious inflammation at least in part on the basis that the subject is determined by the indicator-determining method of any one of embodiments 1 to 109 as having a likelihood of a presence of infectious inflammation; or (2) exposing the subject to a treatment regimen for non-infectious inflammation at least in part on the basis that the subject is determined by the indicator-determining method of any one of embodiments 1 to 108 as having a likelihood of a presence of non-infectious inflammation.

131. The method of embodiment 130, further comprising: taking a sample from the subject and determining an indicator indicative of a likelihood of a presence of infectious inflammation or indicative of a likelihood of a presence of non-infectious inflammation using the indicator-determining method.

132. The method of embodiment 130 or embodiment 131, further comprising: sending a sample obtained from the subject to a laboratory at which the indicator is determined according to the indicator-determining method.

133. The method of embodiment 132, further comprising: receiving the indicator from the laboratory.

134. A kit for determining an indicator used in assessing a likelihood that a type of inflammation is present or absent in a joint of a subject, wherein the type of inflammation is selected from infectious inflammation and non-infectious inflammation, the kit comprising:

(1) for each of at least one nucleic acid biomarker (e.g., 1, 2, 3, 4, 5, 6, 7, 8, 9, 10, 11, 12, 13, 14, 15, 16 or more biomarkers) at least one oligonucleotide primer and/or at least one oligonucleotide probe that hybridizes to the nucleic acid biomarker, wherein the at least one biomarker is selected from a first panel of biomarkers comprising, consisting or consisting essentially of ACO2, AP3M1, ATG4B, C5orf15, CANX, CDKN1A, CSNK1D, CWC27, CXCL8, DTNBP1, DUSP1, EIF2S1, EMP1, ERP44, FCGR3B, FFAR2, FPR1, FYB1, GBP1, H3-3B, HNRNPAB, IARS2, IPO8, IRF2, KCTD2, KCTD3, KLF13, KLHL12, LARP4, LMNA, MCL1, MLLT6, MOCS3, MRPL20, MRPL37, MXD1, MYO1F, NAGA, NAMPT, NINJ1, NUP58, PARP14, PIK3AP1, PIK3R5, PIP4K2B, PKN1, PLEC, PLXDC2, POLG2, POLR2G, PPIL2, PPP5C, PRPF19, PSMC3, RILPL2, RNASEL, RNF26, SEC24B, SLC26A6, SNIP1, SNRPF, SP1, SP2, STX11, SUSD6, TBK1, TNFRSF1B, TTYH3, TWF2, VPS4B, VPS51, WIPF2 and ZZEF1.

135. The kit of embodiment 134, wherein the kit comprises at least one oligonucleotide primer and/or at least one oligonucleotide probe for each of a plurality of biomarkers, wherein the plurality of biomarkers is selected from the first panel of biomarkers and optionally from a second panel of biomarkers comprising API5, AQP9, ATIC, CISH, CLIC4, CSF2RB, CSF3R, DUSP5, ETV6, GADD45B, GRINA, HCK, HLA-E, IER3, IL1B, IL1RN, IMMT, LILRB3, LRPPRC, LYN, NFKBIA, OSM, PDE4B, PI3, PLAUR, PLEK, PPIF, SEMA4D, STARD7, TNFAIP2, TNFAIP3 and ZFP36.

136. The kit of embodiment 134 or embodiment 135, wherein the kit comprises for each of at least 2, 3, 4, 5, 6, 7, 8, 9, 10, 11, 12, 13, 14, 15 or 16 of the nucleic acid biomarkers at least one oligonucleotide primer and/or probe that hybridizes to the nucleic acid biomarker.

137. The kit of embodiment 134 or embodiment 135, wherein the kit comprises for each of up to 2, 3, 4, 5, 6, 7, 8, 9, 10, 11, 12, 13, 14, 15 or 16 of the nucleic acid biomarkers at least one oligonucleotide primer and/or probe that hybridizes to the nucleic acid biomarker.

138. The kit of any one of embodiments 134 to 137, further comprising: a DNA polymerase.

139. The kit of embodiment 138, wherein the DNA polymerase is a thermostable DNA polymerase.

140. The kit of any one of embodiments 134 to 139, further comprising: for each nucleic acid biomarker a pair of forward and reverse oligonucleotide primers that permit nucleic acid amplification of at least a portion of the nucleic acid biomarker to produce an amplicon.

141. The kit of any one of embodiments 134 to 140, further comprising: for each nucleic acid biomarker two pairs of forward and reverse oligonucleotide primers, wherein the oligonucleotide primers of one pair are nested ("nested oligonucleotide primers") relative to the oligonucleotide primers of the other pair, wherein a respective pair of oligonucleotide primers permits nucleic acid amplification of at least a portion of the nucleic acid biomarker to produce an amplicon.

142. The kit of any one of embodiments 134 to 141, further comprising: for each nucleic acid biomarker an oligonucleotide probe that comprises a heterologous label and hybridizes to the nucleic acid biomarker or an amplicon of the nucleic acid biomarker.

143. The kit of any one of embodiments 134 to 142, wherein the components of the kit when used to determine the indicator are combined to form a mixture.

144. The kit of any one of embodiments 134 to 143, wherein the nucleic acid biomarker is CDNA.

145. The kit of any one of embodiments 134 to 144, further comprising: one or more reagents for preparing mRNA from a cell or cell population from a sample obtained from a site of inflammation associated with the joint of the subject.

146. The kit of any one of embodiments 134 to 145, further comprising: one or more reagents for preparing cDNA from the mRNA.

147. The kit of any one of embodiments 134 to 146, further comprising: one or more reagents for amplifying cDNA.

148. The kit of any one of embodiments 134 to 147, further comprising one or more of deoxynucleotides, buffer(s), positive and negative controls, and reaction vessel(s).

149. The kit of any one of embodiments 134 to 148, further comprising instructions for performing the indicator-determining method of any one of embodiments 1 to 108.

In order that the disclosure may be readily understood and put into practical effect, particular preferred embodiments will now be described by way of the following non-limiting examples.

EXAMPLES

Example 1

Identification of Joint Inflammation Biomarkers

Synovial fluid from individual patient joints was drawn into a PAXgene™ tube and frozen. RNA was extracted from the tubes, and RNA-seq libraries were prepared using an AmpliSeq kit (Illumina, San Diego, USA) which amplifies coding regions from about 20,000 genes. The libraries were sequenced using an Illumina HiSeq instrument (Illumina, San Diego, USA) so that 8-10 million reads per sample were generated. The FASTQ files were trimmed and then aligned to the human genome using STAR and the counts were summarized at the gene level, then normalized using EdgeR and log 2 transformed.

Figure 3:
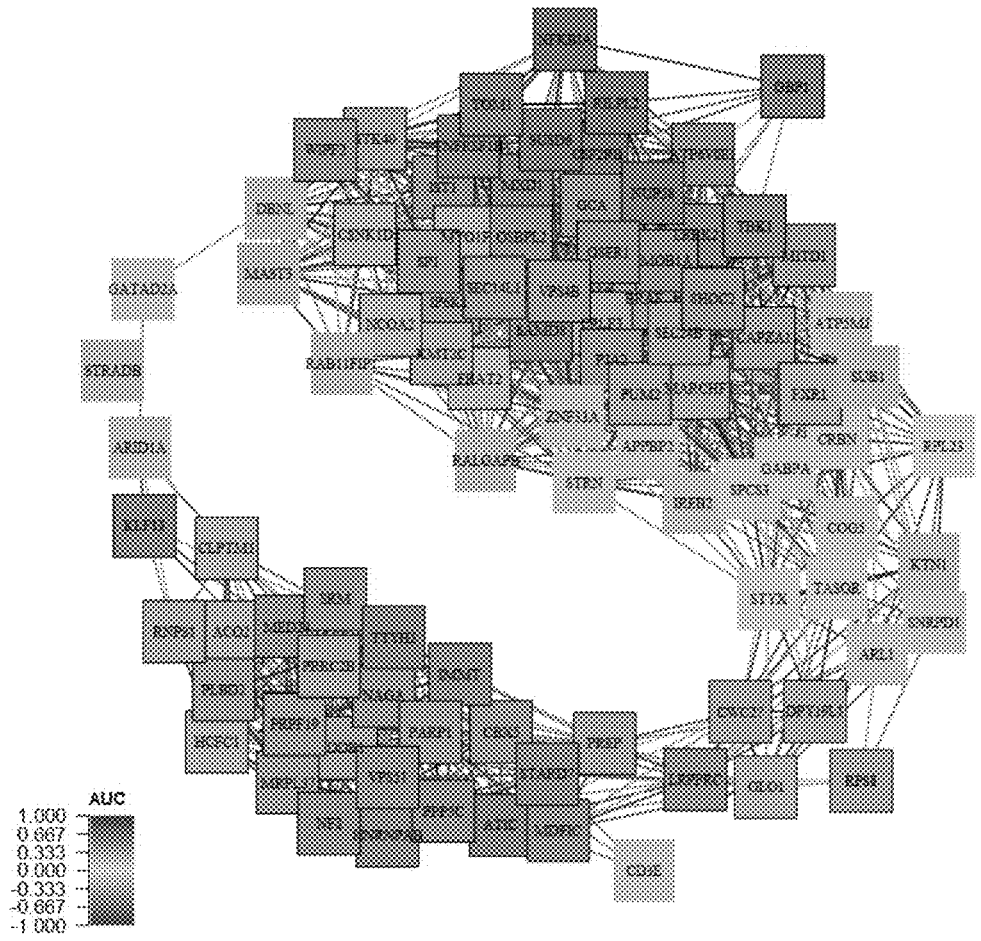
FIG. 3 is a diagrammatic representation showing a network diagram where each square represents one of the gene clusters, and is labeled by the representative gene. Clusters with fewer than 25 members are not included, for clarity. The nodes (squares) are connected by a line if they have a Pearson correlation of at least 0.6. The color of each node is based on the AUC of the ROC curve and ranges from blue to red. Values near 0.5 (grey) do not have any predictive value on their own, values near 1.0 (red) are where the overall gene expression is higher in the cases (infected), and values near 0.0 (blue) are where the gene expression is lower in the infected samples (and higher in sterile). Boxes with a black border have an absolute AUC greater than expected by chance.
Figure 4:
FIG. 4 is a graphical representation showing the number of gene members belonging to each of 269 gene clusters.
Figure 4:
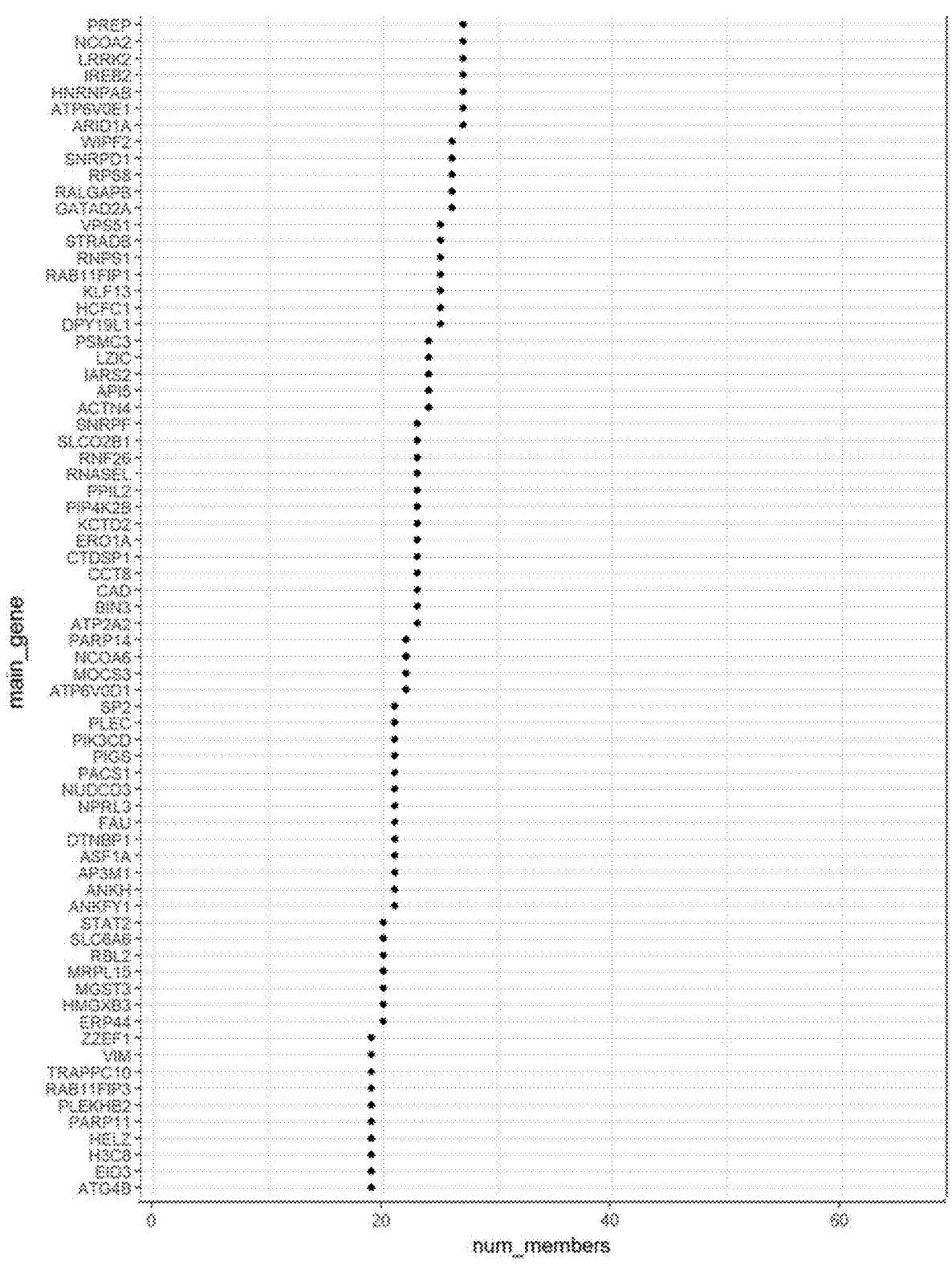
Figure 4:
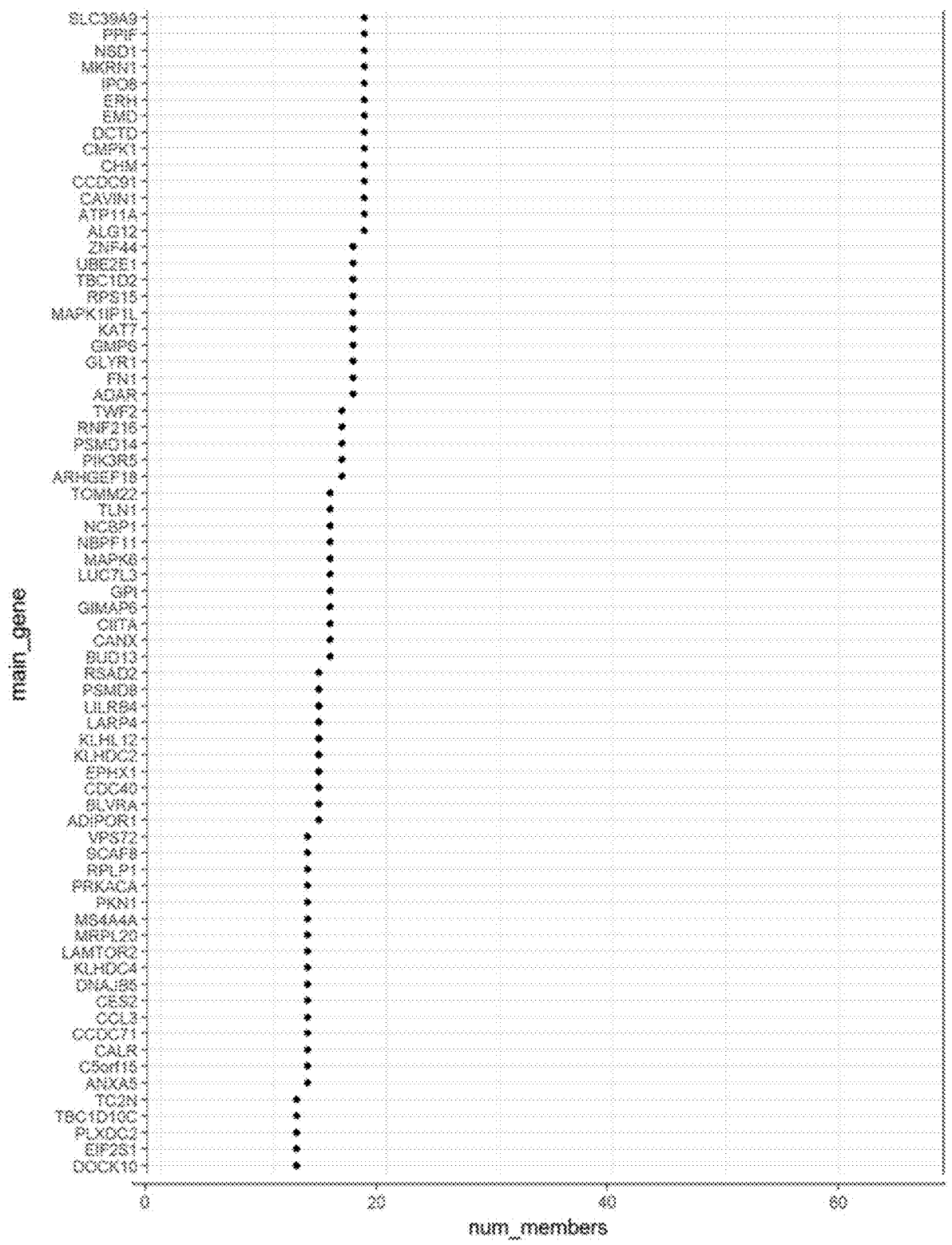
Figure 4:
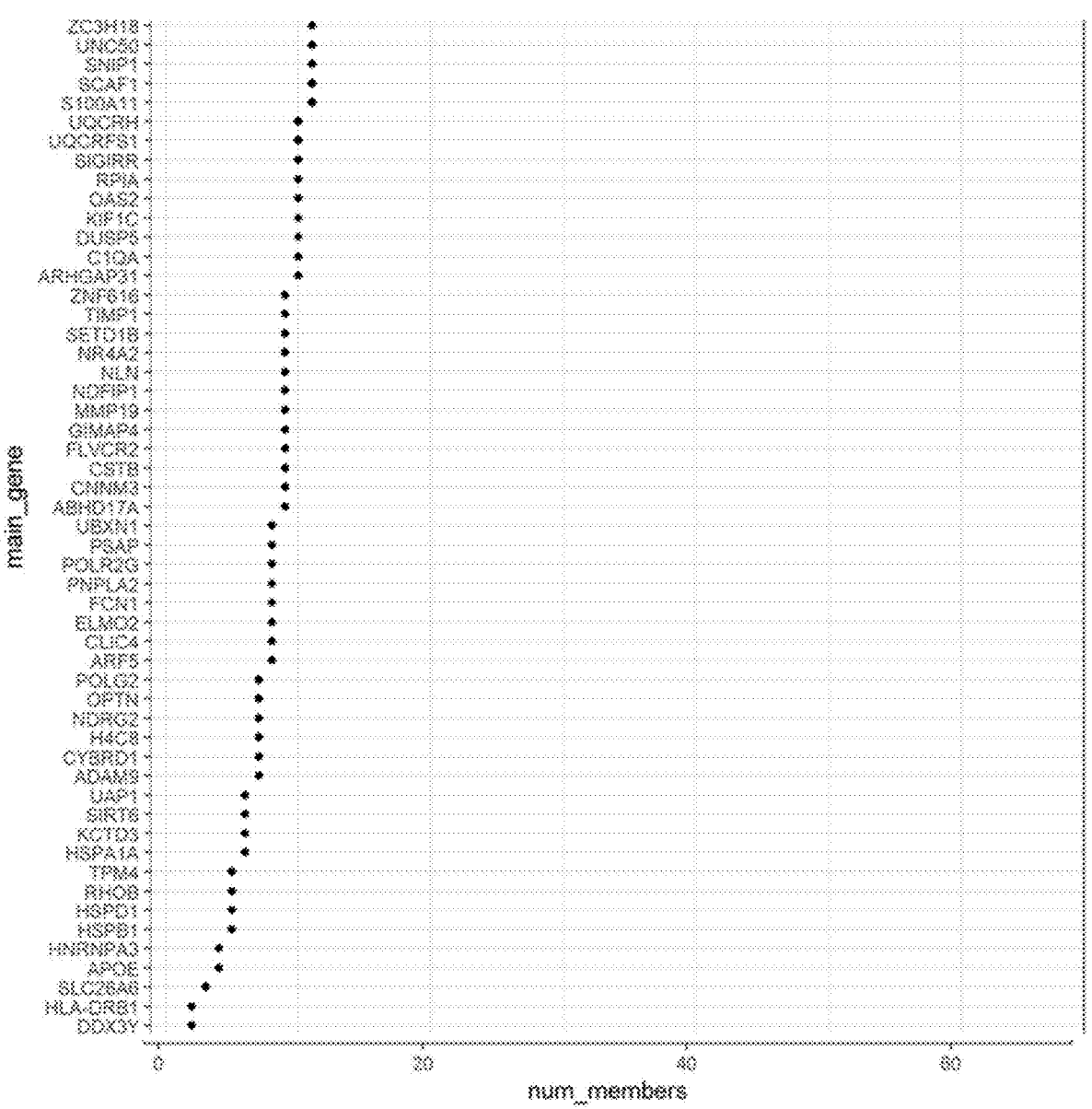

The first analysis step was to focus the biomarker search on a subset of roughly 20,000 genes which were quantitated at the RNA expression level in the samples using RNAseq. The inventors kept the N=6000 genes with the highest mean value, and ignored the remaining expression values. Genes were clustered based on the Pearson correlation similarity of their expression values using the R package called "APcluster" R package for affinity propagation clustering (www<dot>bioinf<dot>jku<dot>at/software/apcluster). This builds a network graph of the 6000 genes based on their similarity to each other and then uses a process called affinity propagation in order to define N=269 discrete clusters of genes (FIG. 3). The gene members of each cluster are more similar to each other than to other clusters, and each gene is only in a single cluster. The clusters have between 2 and 67 genes as members (FIG. 4). A single gene is picked as the representative member of each cluster. Thus, in the following steps, N=269 genes were used as the representative of the 6000 highest expressed genes in the samples.

The 83 samples were then placed into two groups, based on the final retrospective physician diagnosis (RPD) of infected or sterile. In this cohort of patients, there were 40 with infected joints and 43 with sterile inflammation yielding an infection prevalence of 48%. In some clinical settings where this test could be used, the prevalence of infection may be lower than 48% and as low as 10%. Assuming the sensitivity and specificity of this test remains similar as the prevalence is reduced as a result of being used in a different clinical setting, then is it a natural consequence that the NPV would increase accordingly. For example, an NPV at a 50 percentile threshold means that the score threshold would select half of the patients from a balanced cohort as a negative test result. In the scenario with that threshold and prevalence, then the signatures (defined below) have an NPV range of 0.75 to 0.90. If, instead, this same test were used in a cohort with 10% infection prevalence, then the NPV would consequently increase to be in the range of 0.93 to 1.0.

Figure 5:
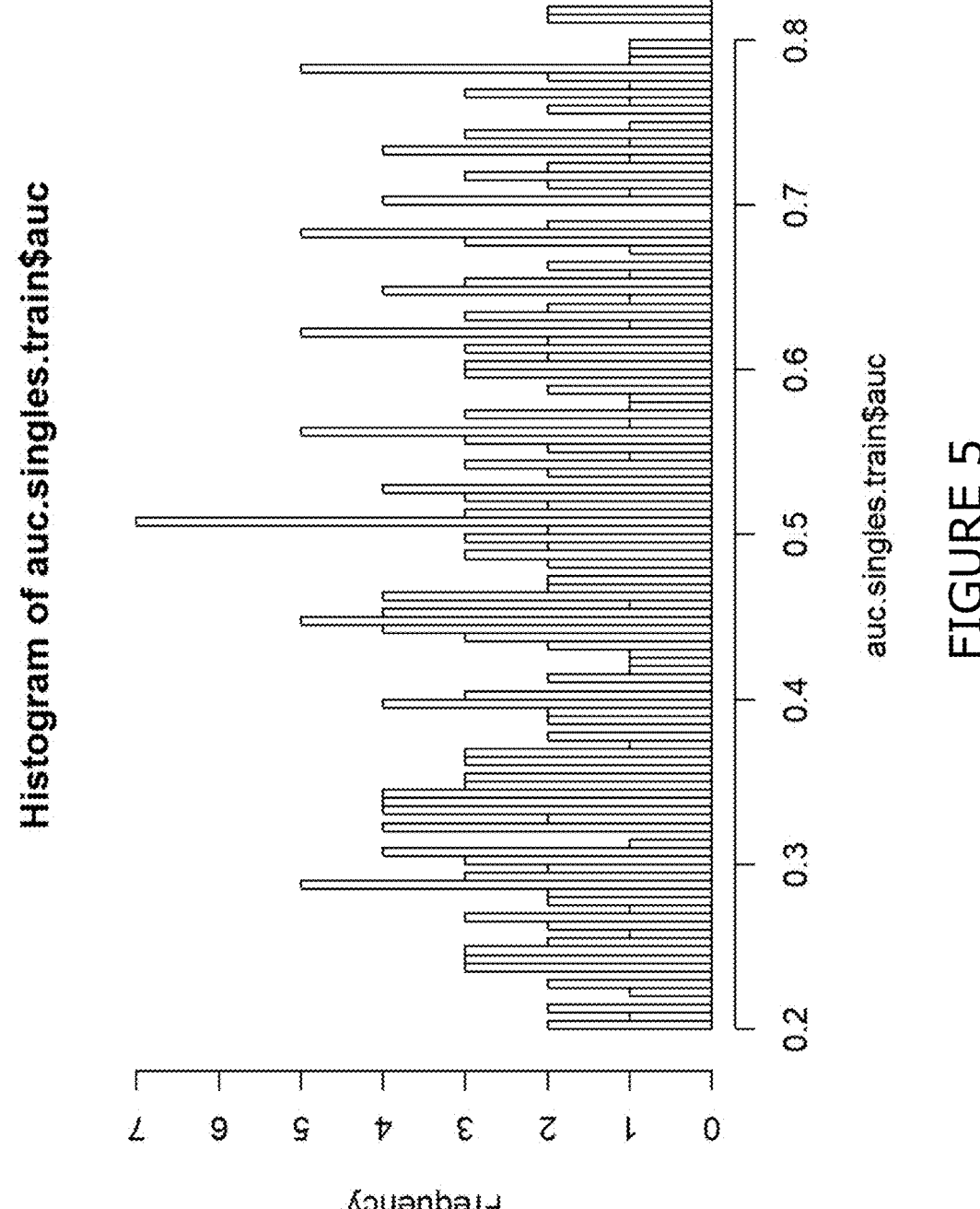
FIG. 5 is a graphical representation showing a histogram of the AUC values for the 269 genes which are the representative members of the 269 clusters.
Figure 6:
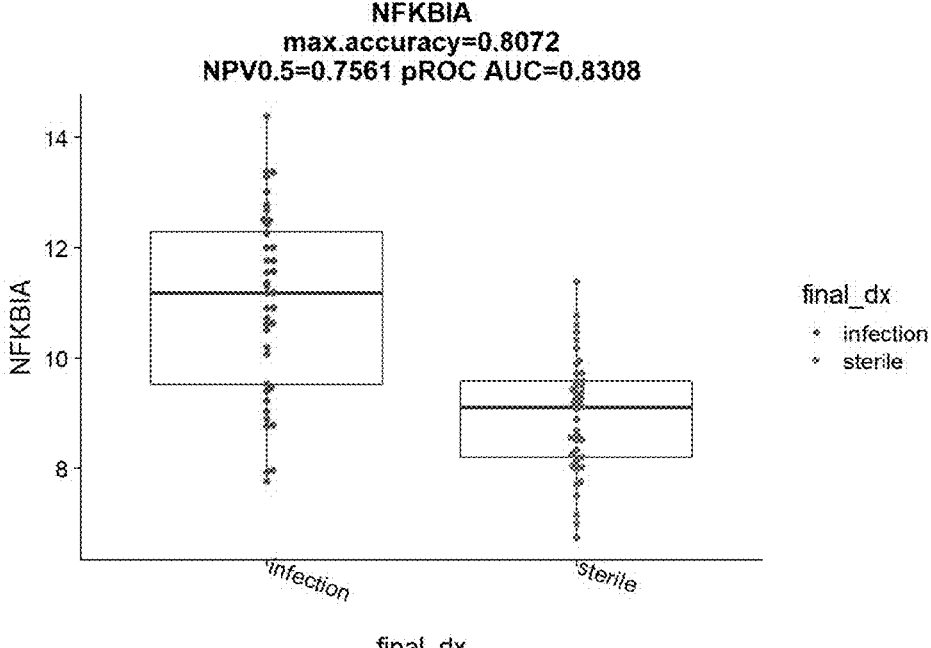
FIG. 6 is a graphical representation showing a box plot and dot plot of the expression values of the gene member with the highest AUC among the 269 clusters, where the samples are split into the two main final retrospective physician diagnosis (RPD) groups of infected and sterile.

The Area Under the Curve (AUC) of the Receiver Operator Characteristic (ROC) curve was calculated using the expression value as the predictor for each of the 269 genes and the final RPD as the outcome or true category (FIG. 5). Of these genes, the gene with the highest AUC (NFKBIA) is shown FIG. 6, which stratifies joint inflammation into infectious joint inflammation ("infected") and non-infectious joint inflammation ("sterile"). TABLE 1 lists the top performing genes based on AUC and p value.

TABLE 1

| Gene | AUC | p Value | Gene | AUC | p Value |
|---|---|---|---|---|---|
| GRINA | 0.83779 | 5.26E-05 | HCK | 0.72849 | 0.00042105 |
| STX11 | 0.83488 | 5.26E-05 | SP1 | 0.71395 | 0.00089474 |
| NINJ1 | 0.83256 | 5.26E-05 | VPS4B | 0.70116 | 0.0016316 |
| NFKBIA | 0.83081 | 5.26E-05 | CISH | 0.69477 | 0.0026842 |
| PIK3AP1 | 0.82907 | 5.26E-05 | ETV6 | 0.69186 | 0.0026842 |
| GADD45B | 0.82791 | 5.26E-05 | SEC24B | 0.68372 | 0.0042105 |
| IL1B | 0.82791 | 5.26E-05 | CANX | 0.68081 | 0.0042105 |
| TNFAIP3 | 0.82733 | 5.26E-05 | CLIC4 | 0.67965 | 0.0042105 |
| PLEK | 0.82326 | 5.26E-05 | SNIP1 | 0.65814 | 0.011053 |
| IER3 | 0.81919 | 5.26E-05 | MYO1F | 0.64709 | 0.018105 |
| RILPL2 | 0.8186 | 5.26E-05 | CSNK1D | 0.63837 | 0.027842 |
| IRF2 | 0.81628 | 5.26E-05 | POLG2 | 0.50872 | 1 |
| NUP58 | 0.81628 | 5.26E-05 | SLC26A6 | 0.49186 | 0.82742 |
| CSF2RB | 0.81337 | 5.26E-05 | KCTD2 | 0.48837 | 0.82742 |
| SUSD6 | 0.81279 | 5.26E-05 | ZZEF1 | 0.48663 | 0.82742 |
| PI3 | 0.80756 | 5.26E-05 | IPO8 | 0.45233 | 0.34195 |
| AQP9 | 0.8064 | 5.26E-05 | POLR2G | 0.4314 | 0.20616 |
| FFAR2 | 0.80465 | 5.26E-05 | ATG4B | 0.42791 | 0.20616 |
| ZFP36 | 0.80407 | 5.26E-05 | PKN1 | 0.36279 | 0.018158 |
| TNFAIP2 | 0.80233 | 5.26E-05 | MOCS3 | 0.34942 | 0.012737 |
| MXD1 | 0.79738 | 5.26E-05 | TWF2 | 0.34244 | 0.0083158 |
| PDE4B | 0.79709 | 5.26E-05 | ACO2 | 0.34128 | 0.0083158 |
| PLAUR | 0.79651 | 5.26E-05 | API5 | 0.32151 | 0.0032632 |
| FCGR3B | 0.79419 | 5.26E-05 | CWC27 | 0.32093 | 0.0032632 |
| NAMPT | 0.79419 | 5.26E-05 | PLXDC2 | 0.3064 | 0.0020526 |
| GBP1 | 0.79012 | 5.26E-05 | PSMC3 | 0.30203 | 0.0013684 |
| TNFRSF1B | 0.78547 | 5.26E-05 | RNF26 | 0.29419 | 0.00084211 |
| DTNBP1 | 0.78488 | 5.26E-05 | LARP4 | 0.29012 | 0.00084211 |
| DUSP5 | 0.78314 | 5.26E-05 | MRPL37 | 0.28837 | 0.00084211 |
| CXCL8 | 0.78198 | 5.26E-05 | SNRPF | 0.28721 | 0.00084211 |
| RNASEL | 0.78023 | 5.26E-05 | EIF2S1 | 0.28547 | 0.00084211 |
| FPR1 | 0.77907 | 5.26E-05 | PRPF19 | 0.28198 | 0.00047368 |
| OSM | 0.77907 | 5.26E-05 | LMNA | 0.26628 | 0.00026316 |
| SEMA4D | 0.77849 | 5.26E-05 | MRPL20 | 0.26628 | 0.00026316 |
| LYN | 0.77791 | 5.26E-05 | NAGA | 0.26628 | 0.00026316 |
| PPIF | 0.77616 | 5.26E-05 | PPIL2 | 0.26512 | 0.00026316 |
| DUSP1 | 0.77384 | 5.26E-05 | EMP1 | 0.26047 | 0.00021053 |
| PARP14 | 0.76977 | 5.26E-05 | LRPPRC | 0.25349 | 0.00015789 |
| TBK1 | 0.76977 | 5.26E-05 | VPS51 | 0.25058 | 0.00015789 |
| FYB1 | 0.76919 | 5.26E-05 | IARS2 | 0.24651 | 0.00015789 |
| C5orf15 | 0.76802 | 5.26E-05 | PPP5C | 0.24419 | 5.26E-05 |
| PIK3R5 | 0.76279 | 5.26E-05 | PIP4K2B | 0.23837 | 5.26E-05 |
| ERP44 | 0.75988 | 5.26E-05 | HNRNPAB | 0.23779 | 5.26E-05 |
| H3-3B | 0.75581 | 5.26E-05 | IMMT | 0.23576 | 5.26E-05 |
| CSF3R | 0.75465 | 5.26E-05 | PLEC | 0.22616 | 5.26E-05 |
| MCL1 | 0.75058 | 5.26E-05 | STARD7 | 0.22616 | 5.26E-05 |
| MLLT6 | 0.75058 | 5.26E-05 | KLF13 | 0.21337 | 5.26E-05 |
| HLA-E | 0.75 | 5.26E-05 | TTYH3 | 0.21017 | 5.26E-05 |
| CDKN1A | 0.74884 | 5.26E-05 | AP3M1 | 0.20698 | 5.26E-05 |
| LILRB3 | 0.74884 | 5.26E-05 | ATIC | 0.20291 | 5.26E-05 |
| IL1RN | 0.73837 | 0.00031579 | KCTD3 | 0.22442 | 5.26E-05 |
| SP2 | 0.73663 | 0.00031579 | KLHL12 | 0.625 | 0.043 |
| WIPF2 | 0.73488 | 0.00042105 | | | |

Figure 7:
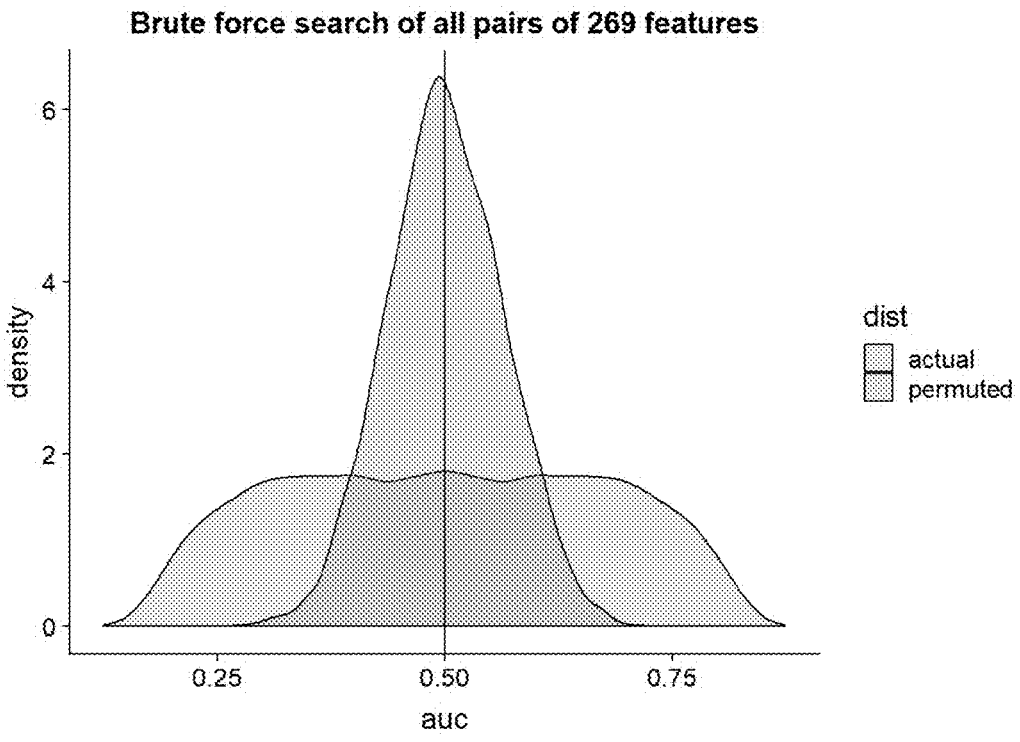
FIG. 7 is a graphical representation showing a smoothed histogram of the AUC values for the 72,092 pairs of genes (pink), compared to the distribution of AUC values (blue) determined from randomly permuted RPD labels of the samples.

All pairs of genes were combined by taking the difference between the 2 genes in each sample, and the AUC of the difference compared to the final RPD was calculated. This was a brute force search of 72,092 pairs of genes. Since the difference was taken of log 2 gene expression values, then this is mathematically equivalent to taking the ratio of the normalized (non log 2 transformed) expression values. Many of the pairs of genes have higher AUCs than would be expected by random chance—as estimated by permuting the labels of the samples and calculating AUCs on many randomly permuted samples and genes (FIG. 7).

The best pairs and genes which are most frequently used in the best 300 pairs are shown in TABLE 2, in which the first gene of a gene pair is expressed at a higher level in infectious joint inflammation than in non-infectious joint inflammation (denoted by a "+" signal), and the second gene of the gene pair is expressed at a lower level in infectious inflammation than in non-infectious inflammation, or improves the discrimination performance of the first gene (denoted by a "−" signal). Second genes that improve the discrimination performance of the first gene are indicated by an asterisk. The column "AUC" shows the AUC for individual first gene/second gene pairs. The columns "NPV 33", "NPV 50" and "NPV 66" show the NPV for individual first gene/second gene combinations at the 33, 50 and 66 percentile thresholds, respectively, for individual first gene/second gene combinations, in this cohort which has an infection prevalence of 48%.

TABLE 2

| First Gene | Second Gene | AUC | NPV 33 | NPV 50 | NPV 66 |
|---|---|---|---|---|---|
| +MXD1 | −MYO1F* | 0.874 | 0.815 | 0.780 | 0.759 |
| +SP2 | −KLF13 | 0.863 | 0.815 | 0.805 | 0.759 |
| +DUSP5 | −PLEC | 0.863 | 0.852 | 0.805 | 0.704 |
| +CSF2RB | −MYO1F* | 0.860 | 0.889 | 0.829 | 0.685 |

TABLE 2-continued

| First Gene | Second Gene | AUC | NPV 33 | NPV 50 | NPV 66 |
|---|---|---|---|---|---|
| +DUSP5 | −PRPF19 | 0.859 | 0.852 | 0.805 | 0.722 |
| +ERP44 | −AP3M1 | 0.859 | 0.889 | 0.756 | 0.722 |
| +NFKBIA | −MOCS3 | 0.858 | 0.852 | 0.780 | 0.722 |
| +CLIC4 | −PLEC | 0.858 | 0.852 | 0.780 | 0.704 |
| +DUSP5 | −VPS51 | 0.855 | 0.889 | 0.780 | 0.722 |
| +DUSP5 | −STARD7 | 0.855 | 0.889 | 0.829 | 0.722 |
| +ERP44 | −CWC27 | 0.855 | 0.852 | 0.829 | 0.741 |
| +NfKBIA | −POLR2G* | 0.853 | 0.852 | 0.780 | 0.741 |
| +DUSP5 | −HNRNPAB | 0.853 | 0.852 | 0.805 | 0.722 |
| +DUSP5 | −ACO2 | 0.853 | 0.852 | 0.780 | 0.685 |
| +DUSP5 | −PPP5C | 0.853 | 0.889 | 0.805 | 0.704 |
| +DUSP5 | −ATIC | 0.853 | 0.852 | 0.805 | 0.722 |
| +DUSP5 | −PIP4K2B | 0.853 | 0.889 | 0.780 | 0.704 |
| +DUSP5 | −TTYH3 | 0.853 | 0.852 | 0.829 | 0.722 |
| +DUSP5 | −MRPL37 | 0.852 | 0.852 | 0.829 | 0.722 |
| +NFKBIA | −RNF26 | 0.851 | 0.815 | 0.756 | 0.722 |

Using TABLE 2, the first mentioned gene ("numerator") of a gene pair is divided by the second mentioned gene ("denominator") of the gene pair to provide a ratio of gene expression levels, which provides a composite score for discriminating infectious joint inflammation from non-infectious joint inflammation. When logarithmic representations (e.g., a PCR cycle time) of measured amounts or concentrations of genes are employed, composite scores for the gene signatures are calculated by subtracting gene expression value for an individual "−" gene from the gene expression value of a corresponding "+" gene.

Figure 8:
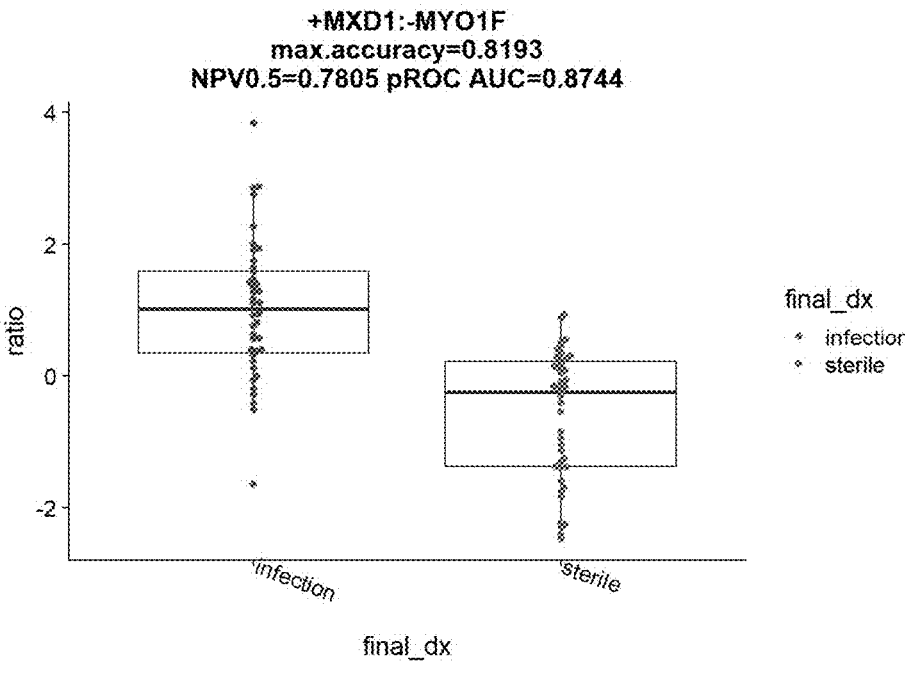
FIG. 8 is a graphical representation showing a boxplot and dot plot of the expression values of the gene pair with the highest AUC among all pairs of the 269 clusters, where the samples are split into the two main final RPD groups of infected and sterile.

The ratio with the maximum AUC is MXD1-MYO1F (see, FIG. 8). These ratios are the building blocks for signatures with larger numbers of genes.

TABLE 3 shows the frequency table for the 20 most frequent "numerator" genes out of the N=300 best gene pairs. The column "Max AUC" shows the maximum of that metric across all signatures which contain that gene. The column "NPV 50" shows the NPV at the 50 percentile threshold for just this gene (not for the best performing signature). Similarly, the column "ROC AUC" shows the AUC for just this gene (not for the best performing signature).

TABLE 3

| Numerator Gene | Frequency | Rank | Max AUC | NPV 50 | ROC AUC |
|---|---|---|---|---|---|
| NFKBIA | 68 | 1 | 0.8581 | 0.7561 | 0.831 |
| DUSP5 | 41 | 2 | 0.8628 | 0.7073 | 0.783 |
| CSF2RB | 37 | 3 | 0.8605 | 0.7317 | 0.813 |
| MXD1 | 20 | 4 | 0.8744 | 0.7561 | 0.797 |
| GBP1 | 16 | 5 | 0.8442 | 0.7073 | 0.790 |
| NUP58 | 13 | 6 | 0.8512 | 0.7561 | 0.816 |
| C5orf15 | 11 | 7 | 0.8474 | 0.7317 | 0.768 |
| RILPL2 | 11 | 8 | 0.8465 | 0.7561 | 0.819 |
| SUSD6 | 11 | 9 | 0.8477 | 0.7073 | 0.813 |
| RNASEL | 9 | 10 | 0.8494 | 0.7317 | 0.780 |
| TNFRSF1B | 9 | 11 | 0.8419 | 0.7561 | 0.785 |
| ERP44 | 8 | 12 | 0.8587 | 0.7073 | 0.760 |
| DTNBP1 | 5 | 13 | 0.8401 | 0.7561 | 0.785 |
| WIPF2 | 5 | 14 | 0.8419 | 0.7073 | 0.735 |
| CLIC4 | 4 | 15 | 0.8581 | 0.6585 | 0.680 |
| SP2 | 4 | 16 | 0.8634 | 0.6829 | 0.737 |
| TBK1 | 4 | 17 | 0.8390 | 0.6829 | 0.770 |
| CANX | 3 | 18 | 0.8494 | 0.6098 | 0.681 |
| PARP14 | 3 | 19 | 0.8372 | 0.7317 | 0.770 |
| PIK3R5 | 3 | 20 | 0.8465 | 0.7073 | 0.763 |

TABLE 4 shows the frequency table for the 20 most frequent "denominator" genes out of the N=300 best gene pairs. Genes that improve the discrimination performance of numerator genes are indicated by an asterisk. The column "Max AUC" shows the maximum of that metric across all signatures which contain that gene. The column "NPV 50" shows the NPV at the 50 percentile threshold for just this gene (not for the best performing signature). Similarly, the column "ROC AUC" shows the AUC for just this gene (not for the best performing signature).

TABLE 4

| Denominator Gene | Frequency | Rank | Max AUC | NPV 50 | ROC AUC |
|---|---|---|---|---|---|
| KLF13 | 20 | 1 | 0.8634 | 0.7317 | 0.213 |
| PLEC | 14 | 2 | 0.8628 | 0.7073 | 0.226 |
| AP3M1 | 9 | 3 | 0.8587 | 0.7317 | 0.207 |
| IARS2 | 8 | 4 | 0.8494 | 0.7073 | 0.247 |
| TTYH3 | 8 | 5 | 0.8529 | 0.7561 | 0.210 |
| TWF2 | 8 | 6 | 0.8401 | 0.6829 | 0.342 |
| EIF2S1 | 7 | 7 | 0.8453 | 0.6585 | 0.285 |
| POLR2G | 7 | 8 | 0.8535 | 0.5610 | 0.431 |
| LRPPRC | 6 | 9 | 0.8372 | 0.6829 | 0.253 |
| PLXDC2 | 6 | 10 | 0.8395 | 0.6585 | 0.306 |
| PPIL2 | 6 | 11 | 0.8465 | 0.6829 | 0.265 |
| ZZEF1 | 6 | 12 | 0.8477 | 0.5366 | 0.487 |
| API5 | 5 | 13 | 0.8512 | 0.6341 | 0.322 |
| CWC27 | 5 | 14 | 0.8547 | 0.6341 | 0.321 |
| PKN1 | 5 | 15 | 0.8465 | 0.5854 | 0.363 |
| CSNK1D* | 4 | 16 | 0.8494 | 0.6585 | 0.638 |
| LARP4 | 4 | 17 | 0.8384 | 0.7073 | 0.290 |
| MRPL20 | 4 | 18 | 0.8413 | 0.6585 | 0.266 |
| NAGA | 4 | 19 | 0.8424 | 0.6829 | 0.266 |
| PIP4K2B | 4 | 20 | 0.8529 | 0.7073 | 0.238 |

Figure 9:
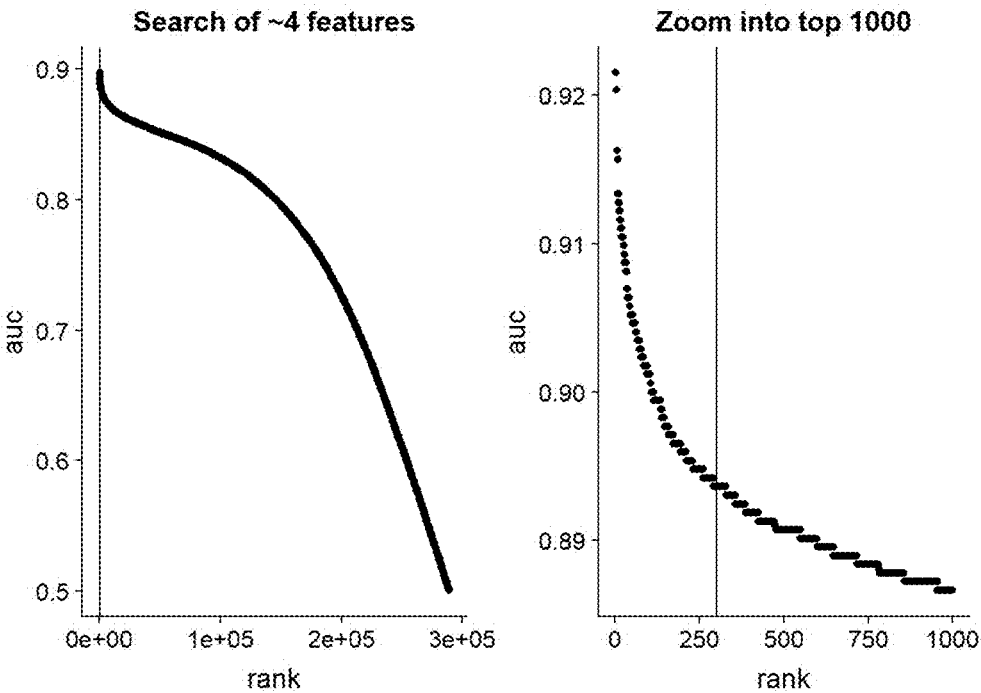
FIG. 9 is a graphical representation showing the AUC of the 300,000 3- to 4-gene signatures that were searched (left panel), and the AUC of the best 1,000 3- to 4-gene signatures from the same data set (right panel).

Signature scores with more than 2 genes were also built, so the best performing ratios are combined with each other to make a score with up to 4 genes. 300,000 4-feature signatures were searched and sorted according to AUC. This search identified 300 3-4 gene signatures whose AUCs was significantly superior to the remaining signatures (see, FIG. 9).

TABLE 5 shows the top 20 signatures with 3-4 genes sorted by AUC, in which the first and second genes ("numerator genes") are expressed at a higher level in infectious joint inflammation than in non-infectious joint inflammation (denoted by a "+" signal), and the third gene and fourth gene (if present) ("denominator genes") are expressed at a lower level in infectious inflammation than in non-infectious inflammation, or improve the discrimination performance of the first and/or second genes (denoted by a "−" signal). Genes that improve the discrimination performance of numerator genes are indicated by an asterisk. When logarithmic representations (e.g., a PCR cycle time) of measured amounts or concentrations of genes are employed, composite scores for the gene signatures are calculated by adding gene expression values for each "+" gene (i.e., "numerator gene") and subtracting gene expression values for each "−" gene (i.e., "denominator gene"). The column "AUC" shows the AUC for individual signatures. The columns "NPV 33", "NPV 50" and "NPV 66" show the NPV for individual signatures at the 33, 50 and 66 percentile thresholds, respectively, in this cohort which has an infection prevalence of 48%.

TABLE 5

| First Gene | Second Gene | Third Gene | Fourth Gene | AUC | NPV 33 | NPV50 | NPV 66 |
|---|---|---|---|---|---|---|---|
| +CLIC4 | +CSF2RB | −POLR2G* | — | 0.922 | 0.963 | 0.805 | 0.722 |
| +CLIC4 | +CSF2RB | −MYOF1* | −PPP5C | 0.920 | 0.963 | 0.878 | 0.722 |
| +CLIC4 | +NUP58 | −EIF2S1 | — | 0.916 | 0.926 | 0.878 | 0.741 |
| +CLIC4 | +DUSP5 | −PLEC | −PSMC3 | 0.916 | 0.963 | 0.829 | 0.741 |
| +CLIC4 | +NUP58 | −API5 | — | 0.913 | 0.889 | 0.829 | 0.759 |
| +CLIC4 | +DUSP5 | −PLEC | −RNF26 | 0.913 | 0.889 | 0.854 | 0.741 |
| +CLIC4 | +CSF2RB | −CSNK1D* | −PPP5C | 0.912 | 0.889 | 0.829 | 0.741 |
| +CLIC4 | +NUP58 | −AP3M1 | — | 0.912 | 0.963 | 0.854 | 0.722 |
| +CLIC4 | +MXD1 | −KCTD2* | | 0.911 | 0.889 | 0.854 | 0.759 |
| +CLIC4 | +MXD1 | −MYO1F* | −PPP5C | 0.910 | 0.926 | 0.854 | 0.759 |
| +CLIC4 | +DUSP5 | −PLEC | −SNRPF | 0.910 | 0.926 | 0.829 | 0.759 |
| +CLIC4 | +CSF2RB | −KCTD2* | | 0.910 | 0.963 | 0.854 | 0.741 |
| +CLIC4 | +CSF2RB | −IPO8* | | 0.910 | 0.926 | 0.829 | 0.741 |
| +CLIC4 | +DUSP5 | −EIF2S1 | −PLEC | 0.909 | 0.926 | 0.829 | 0.741 |
| +CLIC4 | +DUSP5 | −PLEC | −PPP5C | 0.909 | 0.926 | 0.854 | 0.741 |
| +CLIC4 | +CSF2RB | −POLR2G* | −PPP5C | 0.908 | 0.926 | 0.805 | 0.759 |
| +CLIC4 | +TNFRSF1B | −CSNK1D* | −PPP5C | 0.907 | 0.889 | 0.854 | 0.759 |
| +CLIC4 | +CSF2RB | −KCTD2* | −PPP5C | 0.906 | 0.926 | 0.805 | 0.741 |
| +CLIC4 | +RILPL2 | −MOCS3 | −PPP5C | 0.906 | 0.963 | 0.805 | 0.741 |
| +CLIC4 | +NUP58 | −POLR2G* | −TTYH3 | 0.906 | 0.926 | 0.854 | 0.741 |

Figure 10:
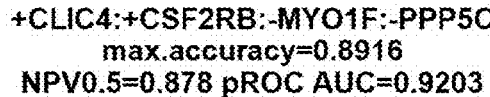
FIG. 10 is a graphical representation showing a boxplot and dot plot of the expression values of the 4-gene signature with the highest AUC among an optimized subset of 3- and 4-gene signatures from the 269 clusters, where the samples are split into the two main final RPD groups of infected and sterile.
Figure 10:
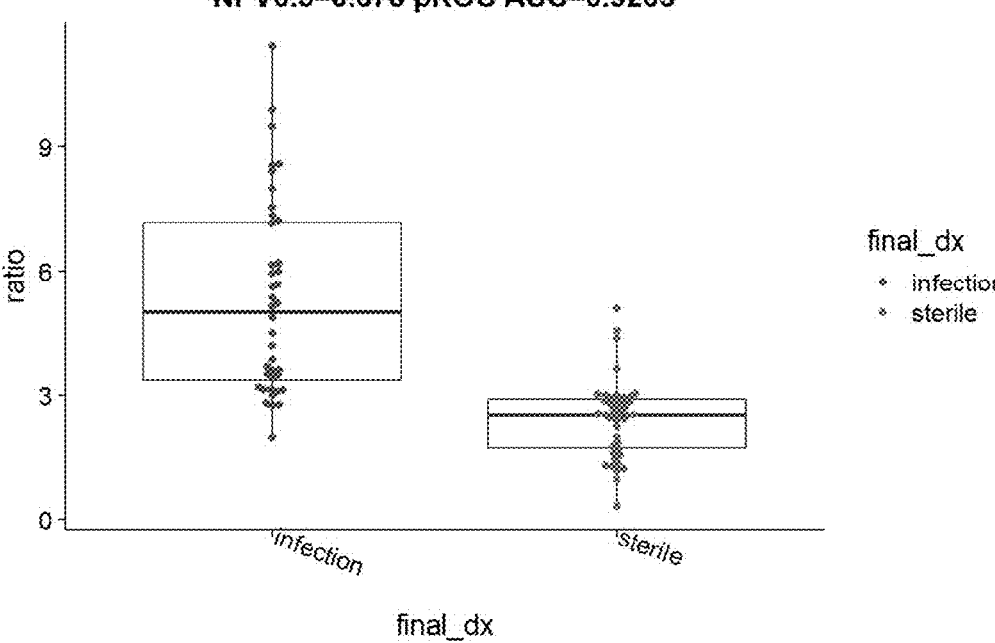

The-4-gene signature with the highest AUC among the 3-4 gene signatures searched is presented in FIG. 10.

TABLE 6 shows the frequency table for the 19 most frequent "numerator" genes in signatures with up to 4 genes. The column "Max AUC" shows the maximum of that metric across all signatures which contain that gene. The column "NPV 50" shows the NPV at the 50 percentile threshold for just this gene (not for the best performing signature). Similarly, the column "ROC AUC" shows the AUC for just this gene (not for the best performing signature).

TABLE 6

| Numerator Gene | Frequency | Rank | Max AUC | NPV 50 | ROC AUC |
|---|---|---|---|---|---|
| DUSP5 | 174 | 1 | 0.9157 | 0.7073 | 0.783 |
| CLIC4 | 161 | 2 | 0.9215 | 0.6585 | 0.680 |
| MXD1 | 55 | 3 | 0.9110 | 0.7561 | 0.797 |
| CSF2RB | 43 | 4 | 0.9215 | 0.7317 | 0.813 |
| RNASEL | 43 | 5 | 0.9052 | 0.7317 | 0.780 |
| NUP58 | 37 | 6 | 0.9163 | 0.7561 | 0.816 |
| SUSD6 | 11 | 7 | 0.9035 | 0.7073 | 0.813 |
| ERP44 | 10 | 8 | 0.8919 | 0.7073 | 0.760 |
| RILPL2 | 10 | 9 | 0.9064 | 0.7561 | 0.819 |
| SP2 | 10 | 10 | 0.9000 | 0.6829 | 0.737 |
| DTNBP1 | 9 | 11 | 0.8971 | 0.7561 | 0.785 |
| CANX | 7 | 12 | 0.8930 | 0.6098 | 0.681 |
| TNFRSF1B | 6 | 13 | 0.9070 | 0.7561 | 0.785 |
| SNIP1 | 4 | 14 | 0.8965 | 0.6098 | 0.658 |
| SP1 | 4 | 15 | 0.8971 | 0.6829 | 0.714 |
| NFKBIA | 3 | 16 | 0.8936 | 0.7561 | 0.831 |
| WIPF2 | 3 | 17 | 0.9023 | 0.7073 | 0.735 |
| PPIF | 2 | 18 | 0.9023 | 0.7561 | 0.776 |
| C5orf15 | 1 | 19 | 0.8948 | 0.7317 | 0.768 |

TABLE 7 shows the frequency table for the 19 most frequent "denominator" genes in signatures with up to 4 genes. The column "Max AUC" shows the maximum of that metric across all signatures which contain that gene. The column "NPV 50" shows the NPV at the 50 percentile threshold for just this gene (not for the best performing signature). Similarly, the column "ROC AUC" shows the AUC for just this gene (not for the best performing signature). Genes that improve the discrimination performance of numerator genes are indicated by an asterisk.

TABLE 7

| Denominator Gene | Frequency | Rank | Max AUC | NPV 50 | ROC AUC |
|---|---|---|---|---|---|
| PPP5C | 58 | 1 | 0.9203 | 0.7073 | 0.244 |
| PLEC | 47 | 2 | 0.9157 | 0.7073 | 0.226 |
| EIF2S1 | 40 | 3 | 0.9163 | 0.6585 | 0.285 |
| POLR2G | 37 | 4 | 0.9215 | 0.5610 | 0.431 |
| TTYH3 | 35 | 5 | 0.9064 | 0.7561 | 0.210 |
| KLF13 | 31 | 6 | 0.9052 | 0.7317 | 0.213 |
| POLG2 | 20 | 7 | 0.9012 | 0.5366 | 0.509 |
| PSMC3 | 18 | 8 | 0.9157 | 0.6585 | 0.302 |
| MYO1F* | 15 | 9 | 0.9203 | 0.6341 | 0.647 |
| ZZEF1 | 15 | 10 | 0.9047 | 0.5366 | 0.487 |
| CSNK1D* | 14 | 11 | 0.9122 | 0.6585 | 0.638 |
| MRPL20 | 14 | 12 | 0.9017 | 0.6585 | 0.266 |
| ACO2 | 13 | 13 | 0.8994 | 0.5854 | 0.341 |
| ATG4B | 13 | 14 | 0.9047 | 0.5366 | 0.428 |
| AP3M1 | 10 | 15 | 0.9116 | 0.7317 | 0.207 |
| IMMT | 10 | 16 | 0.9052 | 0.7073 | 0.236 |
| STARD7 | 10 | 17 | 0.9023 | 0.7073 | 0.226 |
| PKN1 | 8 | 18 | 0.9023 | 0.5854 | 0.363 |
| RNF26 | 8 | 19 | 0.9128 | 0.6585 | 0.294 |

Additionally, the best 3-4-gene signatures can be combined with each other to identify and select up to 8-gene signatures with strong performance for discriminating infectious joint inflammation from non-infectious joint inflammation.

TABLE 8 shows the top 20 signatures with up to 8 genes sorted by AUC, in which the the first gene, second gene, third gene and optional fourth gene ("numerator genes") are expressed at a higher level in infectious inflammation than in non-infectious inflammation (denoted by a "+" signal), and the fifth gene, sixth gene and optional seventh and eighth genes ("denominator genes") are expressed at a lower level in infectious inflammation than in non-infectious inflammation, or improve the discrimination performance of the first gene, second gene, third gene and optional fourth gene (denoted by a "−" signal). Genes that improve the discrimination performance of numerator genes are indicated by an asterisk. When logarithmic representations (e.g., a PCR cycle time) of measured amounts or concentrations of genes are employed, composite scores for the gene signatures are calculated by adding gene expression values for each "+" gene (i.e., "numerator gene") and subtracting gene expression values for each "−" gene (i.e., "denominator gene").

The column "AUC" shows the AUC for individual signatures. The columns "NPV 33", "NPV 50" and "NPV 66" show the NPV for individual signatures at the 33, 50 and 66 percentile thresholds, respectively, in this cohort which has an infection prevalence of 48%.

For the knee, a needle is commonly introduced to the superiolateral aspect of the knee joint to draw fluid from the supra-patella fossa. It is possible to aspirate the knee from a number of locations, this example is the most common location. Once this needle is introduced synovial fluid is

TABLE 8

| First Gene | Second Gene | Third Gene | Fourth Gene | Fifth Gene | Sixth Gene | Seventh Gene | Eighth Gene | AUC | NPV 33 | NPV50 | NPV 66 |
|---|---|---|---|---|---|---|---|---|---|---|---|
| +CLIC4 | +CSF2RB | NUP58 | | -IPO8* | -POLR2G* | | | 0.9471 | 0.963 | 0.902 | 0.759 |
| +CLIC4 | +CSF2RB | NUP58 | | -POLR2G* | -PPP5C | -VPS4B* | | 0.9448 | 1 | 0.878 | 0.759 |
| +CLIC4 | +DUSP5 | SP2 | | -PKN1 | -PLEC | -PPP5C | -RNF26 | 0.9448 | 0.963 | 0.878 | 0.778 |
| +CLIC4 | +NUP58 | SP2 | | -PKN1 | -PLEC | -PPP5C | -VPS4B* | 0.9442 | 1 | 0.878 | 0.778 |
| +CLIC4 | +CSF2RB | DUSP5 | | -PLEC | -POLR2G* | -PSMC3 | | 0.9436 | 1 | 0.878 | 0.778 |
| +CLIC4 | +CSF2RB | DUSP5 | +RNASEL | -ATG4B* | -KLF13 | -POLR2G* | | 0.9436 | 1 | 0.878 | 0.778 |
| +CLIC4 | +CSF2RB | NUP58 | +SNIP1 | -POLR2G* | -PPIL2 | -VPS4B* | | 0.9436 | 1 | 0.854 | 0.759 |
| +CLIC4 | +CSF2RB | DUSP5 | | -POLR2G* | -PPP5C | -RNF26 | | 0.9430 | 0.963 | 0.878 | 0.759 |
| +CLIC4 | +NUP58 | SP2 | | -PKN1 | -PLEC | -PPP5C | -SEC24B* | 0.9430 | 0.963 | 0.854 | 0.796 |
| +CLIC4 | +CSF2RB | DUSP5 | | -MYO1F* | -PLEC | -PPP5C | -RNF26 | 0.9424 | 1 | 0.854 | 0.759 |
| +CLIC4 | +PPIF | SP2 | | -PKN1 | -PLEC | -PPP5C | -SLC26A6* | 0.9424 | 0.963 | 0.854 | 0.778 |
| +CLIC4 | +CSF2RB | NUP58 | | -KLHL12* | -POLR2G* | -PPP5C | | 0.9419 | 1 | 0.854 | 0.759 |
| +CLIC4 | +DUSP5 | SP2 | | -PKN1 | -PLEC | -PPP5C | -PSMC3 | 0.9419 | 0.963 | 0.878 | 0.759 |
| +CLIC4 | +CSF2RB | DUSP5 | | -CSNK1D* | -PPP5C | -PPP5C | -RNF26 | 0.9419 | 0.963 | 0.878 | 0.759 |
| +CLIC4 | +CSF2RB | DUSP5 | | -AP3M1 | -PPP5C | -RNF26 | | 0.9419 | 0.963 | 0.878 | 0.759 |
| +CLIC4 | +CSF2RB | DUSP5 | | -PLXDC2 | -PPP5C | -RNF26 | | 0.9413 | 0.963 | 0.878 | 0.759 |
| +CLIC4 | +DUSP5 | SP2 | | -KCTD3 | -PKN1 | -PLEC | -PPP5C | 0.9407 | 0.963 | 0.854 | 0.778 |
| +CLIC4 | +NUP58 | SP2 | | -PKN1 | -PLEC | -POLR2G* | | 0.9407 | 0.963 | 0.878 | 0.778 |
| +CLIC4 | +DUSP5 | NUP58 | | -PLEC | -PPP5C | -RNF26 | -SEC24B* | 0.9401 | 0.926 | 0.878 | 0.759 |
| +CLIC4 | +DUSP5 | SP2 | | -KLF13 | -PLEC | -PPP5C | -RNF26 | 0.9401 | 0.926 | 0.878 | 0.759 |

Figure 11:
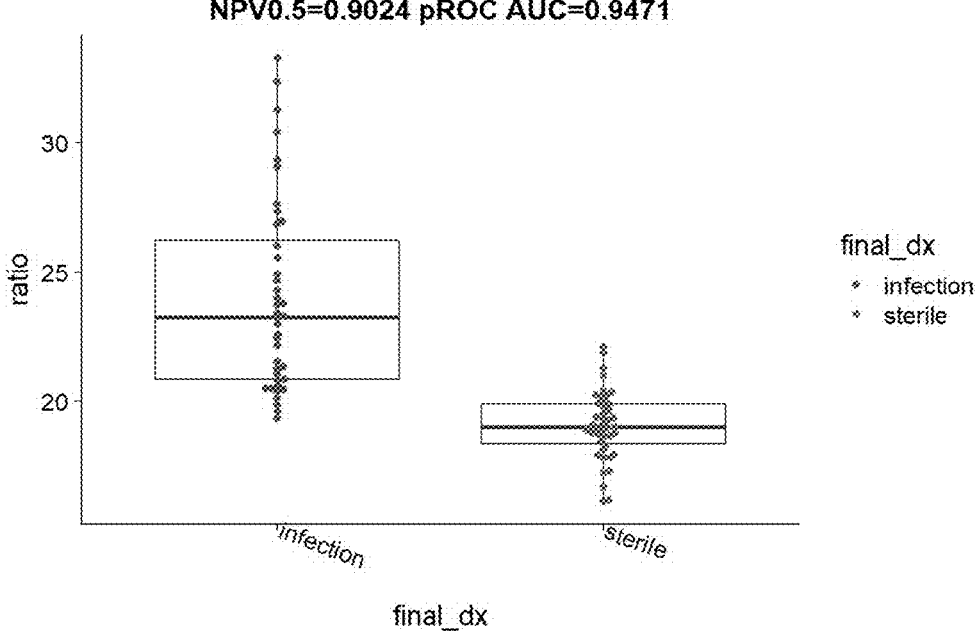
FIG. 11 is a graphical representation showing a boxplot and dot plot of the expression values of the 6-gene signature with the highest AUC among an optimized subset of 6- to 8-gene signatures from the 269 clusters, where the samples are split into the two main final RPD groups of infected and sterile.

The-gene signature with the highest AUC among the 5-8 gene signatures searched is presented in FIG. 11.

TABLE 9 shows the frequency table for the 19 most frequent genes in the top 5% of all 8-feature signatures.

TABLE 9

| Gene | Frequency | Rank |
|---|---|---|
| CLIC4 | 20714 | 1 |
| DUSP5 | 8842 | 2 |
| PPP5C | 7198 | 3 |
| CSF2RB | 5810 | 4 |
| NUP58 | 5468 | 5 |
| PLEC | 4764 | 6 |
| POLR2G | 3380 | 7 |
| RNASEL | 2478 | 8 |
| MXD1 | 2306 | 9 |
| RNF26 | 1948 | 10 |
| SP2 | 1938 | 11 |
| PKN1 | 1914 | 12 |
| EIF2S1 | 1736 | 13 |
| ATG4B | 1540 | 14 |
| PSMC3 | 1448 | 15 |
| KLF13 | 1396 | 16 |
| CSNK1D | 1348 | 17 |
| VPS4B | 1228 | 18 |
| ZZEF1 | 1126 | 19 |

Notably, 2, 3 or 4 of the ratios can be used in order to build larger signatures for differentiating patients with infectious joint inflammation and patients with non-infectious joint inflammation.

Example 2

Sample Extraction

The joint to be aspirated is first prepared using a skin disinfectant agent. Any commonly used skin preparation solution is acceptable for this process. All aspirations are completed using the sterile no-touch technique.

aspirated from the joint space by drawing back on the plunger.

For the hip, a needle is introduced to the anteromedial aspect of the hip. Care is taken to palpate the important neurovascular structures adjacent to the optimal entry point. Once the femoral artery is palpated as it exits the inguinal ligament, the needle is passed directly toward the hip joint through the overlying muscle and fascia. It is possible to aspirate the hip from a number of locations, this example is the most common location. Once the needle is in the joint capsule synovial fluid is aspirated by drawing back on the plunger. There are additional approaches to the hip joint for aspiration. These are described in orthopedic text books in exacting detail. This example is for illustrative purposes only and by no means provides an exhaustive method by which the hip joint can be aspirated.

For the shoulder, a needle is introduced to the anterior aspect of the shoulder joint immediately inferior and lateral to the coracoid process. It is possible to aspirate the shoulder from a number of locations, this example is the most common location. Once the needle is introduced, synovial fluid is aspirated from the joint space by drawing back on the plunger.

For the ankle, a needle is introduced to the anteromedial aspect of the joint line taking care to avoid the tibialis anterior tendon. It is possible to aspirate the ankle from a number of locations, this example is the most common location. The needle is introduced medial to the tibialis anterior tendon. Once this needle is introduced, synovial fluid is aspirated from the joint space by drawing back on the plunger.

For all other smaller joints, there are several techniques described in orthopedic text books in exacting detail. We have chosen to describe the main joints in detail for illustrative purposes. This list is not exhaustive.

Fluid extracted from a patient can be synovial fluid, exudate, lymph, blood or a combination of all of the above, and may contain tissue.

Approximately 2.5 mL-5 mL of fluid is retrieved and transferred to a PAXgene™ tube (QIAGEN, kit catalogue #762164; Becton Dickinson, Collection Tubes catalogue number 762165; K042613) using the sterile no touch technique.

Once the fluid is obtained and safely stored in the PAX-gene™ tube, the sample is inverted 10 times as per manufacturer instruction and stored at room temperature for transport to the laboratory for processing. For long term storage, PAXgene™ tubes are place in either −20 C or −80 C freezer. Storage at −20 C will last for 5 years, storage at −80 C will last 8 years. Once locally stored samples are ready for transportation to a central laboratory it is important to maintain cold chain shipping for the continued integrity of the sample. Cold chain shipping using dry ice to ensure successful and safe transportation to laboratory for analysis Example 3

RNA Isolation

RNA is suitably isolated using the following steps:

Defrost the frozen sample of synovial fluid immersed in the RNA preserving additive in the PAXgene tube Ensure all reagents are present for PCR.

Centrifuge the PAXgene™ tube for 15 minutes at 5000 g (this is longer than the standard time of 10 minutes)

Remove supernatant by decanting or pipetting.

Add 4 mL of RNase-Free water to the pellet and close with supplied haemoguard closure Vortex until pellet is dissolved, this will take 5-10 min per sample.

Centrifuge again for 15 min at 5000 g (this is longer than the standard time of 10 minutes)

Remove supernatant and discard

Add 350 μL of resuspension buffer one and vortex until dissolved.

Pipette the sample into a 1.5 mL microcentrifuge tube and add 300 μL of binding buffer (BR2) and 40 μL of protein kinase (PK). Vortex for 5 seconds or until dissolved.

Incubate for 10 minutes at 55° C. using a shaker incubator at 1000 rpm.

Pipette the lysate directly into a PAXgene™ shredder spin column and then centrifuge for 3 minutes at max speed (<20,000 g).

Transfer supernatant to fresh 1.5 mL microcentrifuge tube and DO NOT disturb the pellet.

Add 350 μL of pure ethanol and mix by vortexing. Once vortexed centrifuge for 1-2 sec at 1000 g Pipette 700 μL of sample into PAXgene™ RNA spin column and centrifuge for 1 min at 20,000 g.

Pipette the remaining sample into the PAXgene™ RNA spin column and centrifuge for 1 min at 20,000 g Pipette 350 μL of wash buffer (BR3) into the PAXgene™ RNA spin column and centrifuge for 1 min at 20,000 g Add 10 μL of DNase stock solution into 70 μL of DNA digestion buffer into 1.5 mL microcentrifuge tube and mix by flicking.

Pipette DNase solution into the PAXgene™ RNA spin column and leave on bench top at 25° C. for 15 min Pipette 350 μL of wash buffer (BR3) into the PAXgene™ RNA spin column and centrifuge for 1 min at 20,000 g.

Pipette 500 μL of wash buffer 2 (BR4) into the PAX-gene™ RNA spin column and centrifuge for 1 min at 20,000 g.

Add 500 μL of wash buffer 2 into the PAXgene™ RNA spin column and centrifuge for 3 min at 20,000 g Change processing tubes and centrifuge for 1 min at 20,000 g.

Pipette 40 μL elution buffer (BR5) directly onto the membrane and centrifuge for 1 minute at 20,000 g Repeat previous elution step.

Incubate the eluate for 5 min at 65° C. in a shaker-incubator, then chill immediately on ice.

Extracted RNA may be then tested for purity and yield (for example by running an $A_{260/280}$ ratio using a Nano-drop™ (Thermo Scientific)) for which a minimum quality must be (ratio>1.6). RNA should be adjusted in concentration to allow for a constant input volume to the reverse transcription reaction (below). RNA should be processed immediately or stored in single-use volumes at or below −70° C. for later processing.

Example 4

Example Workflow for Reverse Transcription, Real-Time qPCR and Results Interpretation An example workflow for measuring joint inflammation RNA biomarkers will now be described. The workflow involves a number of steps depending upon availability of automated platforms. The assay uses quantitative, real-time determination of the amount of each joint inflammation RNA transcript in the sample based on the detection of fluorescence on a real-time quantitative PCR (RT-qPCR) instrument (e.g., HighPlex Alliance 24 extraction, amplification and reader by AusDiagnostics, IFU REF;91501 ARTG identifier 177847, European Union CE Marked—GTIN: 9343044002298 and Basic UDI-DI: 9343044048033APE). Transcripts are each reverse-transcribed, amplified, detected, and quantified in a separate reaction well. Such reactions can be run as single-plexes (one probe for one transcript per tube), multiplexed (multiple probes for multiple transcripts in one tube), one-step (reverse transcription and PCR are performed in the same tube), or two-step (reverse transcription and PCR performed as two separate reactions in two tubes). A score is calculated using interpretive software provided separately to the kit but designed to integrate with RT-PCR machines.

The workflow below describes the use of manual processing and a pre-prepared kit.

Reverse Transcription

Determine the appropriate number of reaction equivalents to be prepared (master mix formulation) based on a plate map and the information provided directly below. Each clinical specimen is run in singleton.

Each batch run desirably includes the following specimens: RNA Reference High Control, RNA Reference Low Control 1 and 2, Negative Control, and No Template Control (Test Diluent instead of sample) in singleton each Program the HighPlex Alliance 24 Instrument as detailed below.

Launch the MT Assay Setup software icon on the desktop. Select 384 well analyser as default.

Choose the correct analyser—OrthoDx MT Analyser or Roche LC480.

Choose preferred save locations as "Documents" folder.

In the New Run Wizard, select the following options:

i. Assay: Standard Curve (Absolute Quantitation)

ii. Container: 96-Well Clear iii. Template: Blank Document (or select a laboratory-defined template)

iv. Run Mode: Normal v. Operator: Enter operator's initials vi. Plate name: Step 1 tubes and Step 2 plate vii. Click Finish viii. Select the Instrument tab in the upper left ix. The OrthoDx MT Analyser will perform the following thermal cycle times:

x. 25° C. for 10 min xi. 45° C. for 45 min xii. 93° C. for 10 min xiii. Hold at 25° C. for 60 min In a template-free area, remove the Test Diluent and RT-qPCR Test RT Buffer to room temperature to thaw. Leave the RT-qPCR Test RT Enzyme mix in the freezer and/or on a cold block.

In a template-free area, assemble the master mix in the order listed below.

RT Master Mix-Calculation:

|  | Per well × N | |
| --- | --- | --- |
| RT-qPCR Test RT Buffer | 3.5 μL | 3.5 × N |
| RT-qPCR Test RT Enzyme mix | 1.5 μL | 1.5 × N |
| Total Volume | 5 μL | 5 × N |

Gently vortex the master mix then pulse spin. Add the appropriate volume (5 μL) of the RT Master Mix into each well at room temperature.

Remove sample RNAs and control RNAs to thaw. (If the sample RNAs routinely take longer to thaw, this step may be moved upstream in the validated method.)

Vortex the clinical specimens and control RNAs, then pulse spin. Add 10 μL of control RNA or RT-qPCR Test Diluent to each respective control or negative well.

Add 10 μL of sample RNA to each respective sample well (150 ng total input for RT; OD260/OD280 ratio greater than 1.6). Add 10 μL of RT-qPCR Test Diluent to the respective NTC well.

Note: The final reaction volume per well is 15 μL.

|  | Samples |
| --- | --- |
| RT Master Mix | 5 μL |
| RNA sample | 10 μL |
| Total Volume (per well) | 15 μL |

Mix by gentle pipetting. Avoid forming bubbles in the wells.

Cover wells with a seal.

Spin the plate to remove any bubbles (1 minute at 400×g).

Rapidly transfer to OrthoDx HighPlex 24 Instrument pre-programmed as detailed above.

Click Start. Click Save and Continue. Before leaving the instrument, it is recommended to verify that the run started successfully by displaying a time under Estimated Time Remaining.

qPCR master mix may be prepared to coincide roughly with the end of the RT reaction. For example, start about 15 minutes before this time. See below.

When RT is complete (i.e. resting at 25° C.; stop the hold at any time before 60 minutes is complete), spin the plate to collect condensation (1 minute at 400×g).

qPCR Preparation

Determine the appropriate number of reaction equivalents to be prepared (master mix formulation) based on a plate map and the information provided in RT Preparation above.

Program the OrthoDx HighPlex MT Processor with the settings below.

a) Launch the software.

b) Click Create New Document c) In the New Run Wizard, select the following options:

d) Assay: Standard Curve (Absolute Quantitation)

e) Container: 96-Well Clear f) Template: Blank Document (or select a laboratory-defined template)

g) Run Mode: Normal h) Operator: Enter operator's initials i) Plate Name: Enter desired file name j) Plate name: Step 1 tubes and Step 2 plate k) Click Finish a) Click Next b) In the Select Detectors dialog box:

i. Select the detector for the first biomarker, and then click Add>>.

ii. Select the detector second biomarker, and then click Add>>, etc.

iii. Passive Reference: ROX a) Click Next b) Assign detectors to appropriate wells according to plate map.

i. Highlight wells in which the first biomarker assay will be assigned ii. Click use for the first biomarker detector iii. Repeat the previous two steps for the other biomarkers iv. Click Finish a) Ensure that the Setup and Plate tabs are selected b) Select the Instrument tab in the upper left c) In the Thermal Cycler Protocol area, Thermal Profile tab, perform the following actions:

i. Delete Stage 1 (unless this was completed in a laboratory-defined template).

ii. Enter sample volume of 25 μL.

iii. 95° C. 10 minutes iv. 40 cycles of 95° C. for 15 seconds, 63° C. for 1 minute v. Collect data using the "stage 2, step 2 (63.0@1:00)" setting a) Label the wells as below using this process: Right click over the plate map, then select Well Inspector. With the Well Inspector open, select a well or wells. Click back into the Well Inspector and enter the Sample Name. Close the Well Inspector when completed.

i. CONH for High Control ii. CONL for Low Control iii. CONN for Negative Control iv. NTC for No Template Control v. [Accession ID] for clinical specimens a) Ensure that detectors and quenchers are selected as listed below.

i. FAM for biomarker 1; quencher=none ii. FAM for biomarker 2; quencher=none iii. FAM for biomarker 3; quencher=none iv. FAM for biomarker 4; quencher=none v. FAM for biomarker 5; quencher=none vi. FAM for biomarker 6; quencher=none vii. Select "ROX" for passive reference qPCR In a template-free area, remove the assay qPCR Buffer and assay Primer/Probe Mixes for each target to room temperature to thaw. Leave the assay AmpliTaq™ Gold in the freezer and/or on a cold block.

Still in a template-free area, prepare qPCR Master Mixes for each target in the listed order at room temperature. qPCR Master Mixes—Calculation Per Sample

| | Per well × N | |
|---|---|---|
| qPCR Buffer | 11 µL | 11 × N |
| Primer/Probe Mix | 3.4 µL | 3.4 × N |
| TM AmpliTaq Gold | 0.6 µL | 0.6 × N |
| Total Volume | 15 µL | 15 × N |

Gently mix the master mixes by flicking or by vortexing, and then pulse spin. Add 15 µL of qPCR Master Mix to each well at room temperature.

In a template area, add 130 µL of Test Diluent to each cDNA product from the RT Reaction. Reseal the plate tightly and vortex the plate to mix thoroughly.

Add 10 µL of diluted cDNA product to each well according to the plate layout.

Mix by gentle pipetting. Avoid forming bubbles in the wells.

Cover wells with an optical seal.

Spin the plate to remove any bubbles (1 minute at 400×g).

Place on real-time thermal cycler pre-programmed with the settings above.

Click Start. Click Save and Continue. Before leaving the instrument, it is recommended to verify that the run started successfully by displaying a time under Estimated Time Remaining.

Note: Do not open the qPCR plate at any point after amplification has begun. When amplification has completed, discard the unopened plate.

Software, Interpretation of Results and Quality Control

Software is specifically designed to integrate with the output of PCR machines and to apply an algorithm based on the use of multiple biomarkers. The software takes into account appropriate controls and reports results in a desired format.

When the run has completed on the OrthoDx HighPlex MT Processor Instrument, complete the steps below in the application with the included 21 CFR Part 11 Software, OrthoDx software V 1.0

Click on the Results tab in the upper left corner.

Click on the Amplification Plot tab in the upper left corner.

In the Analysis Settings area, select an auto baseline and manual threshold for all targets. Enter 0.01 as the threshold.

Click on the Analyze button on the right in the Analysis Settings area.

From the menu bar in the upper left, select File then Close.

Complete the form in the dialog box that requests a reason for the change. Click OK.

Transfer the data file (.sds) to a separate computer running the specific assay RT-qPCR Test Software.

Launch the assay RT-qPCR Test Software. Log in.

From the menu bar in the upper left, select File then Open.

Browse to the location of the transferred data file (.sds). Click OK.

The data file will then be analyzed using the assay's software application for interpretation of results.

Interpretation of Results and Quality Control
Results

Launch the interpretation software. Software application instructions are provided separately.

Following upload of the .sds file, the Software will automatically generate classifier scores for controls and clinical specimens.

Controls

The Software compares each CON (control) specimen (CONH, CONL, CONN) to its expected result. The controls are run in singleton.

| Control specimen | | |
|---|---|---|
| Designation | Name | Expected result |
| CONH | High Control | Score range |
| CONL | Low Control | Score range |
| CONN | Negative Control | Score range |
| NTC | No Template Control | Fail (no Ct for all targets) |

If CONH, CONL, and/or CONN fail the batch run is invalid and no data will be reported for the clinical specimens. This determination is made automatically by the interpretive software. The batch run should be repeated starting with either a new RNA preparation or starting at the RT reaction step.

If NTC yields a result other than Fail (no Ct for all targets), the batch run is invalid and no data may be reported for the clinical specimens. This determination is made by visual inspection of the run data. The batch run should be repeated starting with either a new RNA preparation or starting at the RT reaction step.

If a second batch run fails, please contact technical services. If both the calibrations and all controls are valid, then the batch run is valid and specimen results will be reported.

Specimens

Note that a valid batch run may contain both valid and invalid specimen results.

Analytical criteria (e.g. Ct values) that qualify each specimen as passing or failing (using pre-determined data) are called automatically by the software.

Scores out of range—reported.

Quality Control

Singletons each of the Negative Control, Low Positive Control, and High Positive Control must be included in each batch run. The batch is valid if no flags appear for any of these controls.

A singleton of the No Template Control is included in each batch run and Fail (no Ct for all targets) is a valid result indicating no amplifiable material was detectable in the well.

The negative control must yield a Negative result. If the negative control is flagged as Invalid, then the entire batch run is invalid.

The low positive and high positive controls must fall within the assigned ranges. If one or both of the positive controls are flagged as Invalid, then the entire batch run is invalid.

Figure 12:
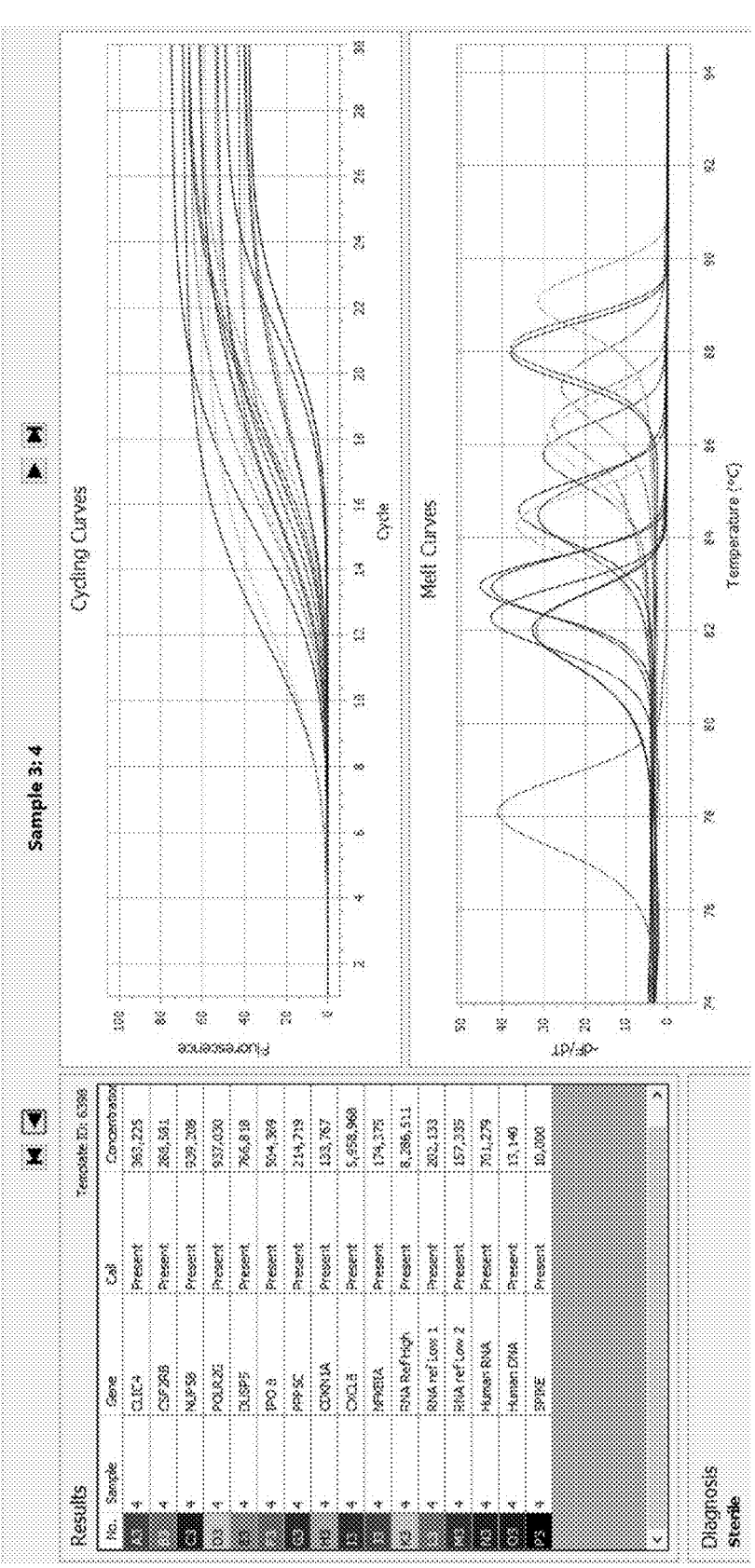
FIG. 12 is an illustration of a typical PCR output depicting cycling curves and melting curves of amplified gene products, representing the expression profile of a biomarker panel including CLIC4, CSF2RB, NUP58, POLR2G, DUSP5, IPO8, PPP5C, CDKN1A, CXCL8 and NFKBIA, in a synovial fluid sample taken from a subject with infectious joint inflammation.
Figure 13:
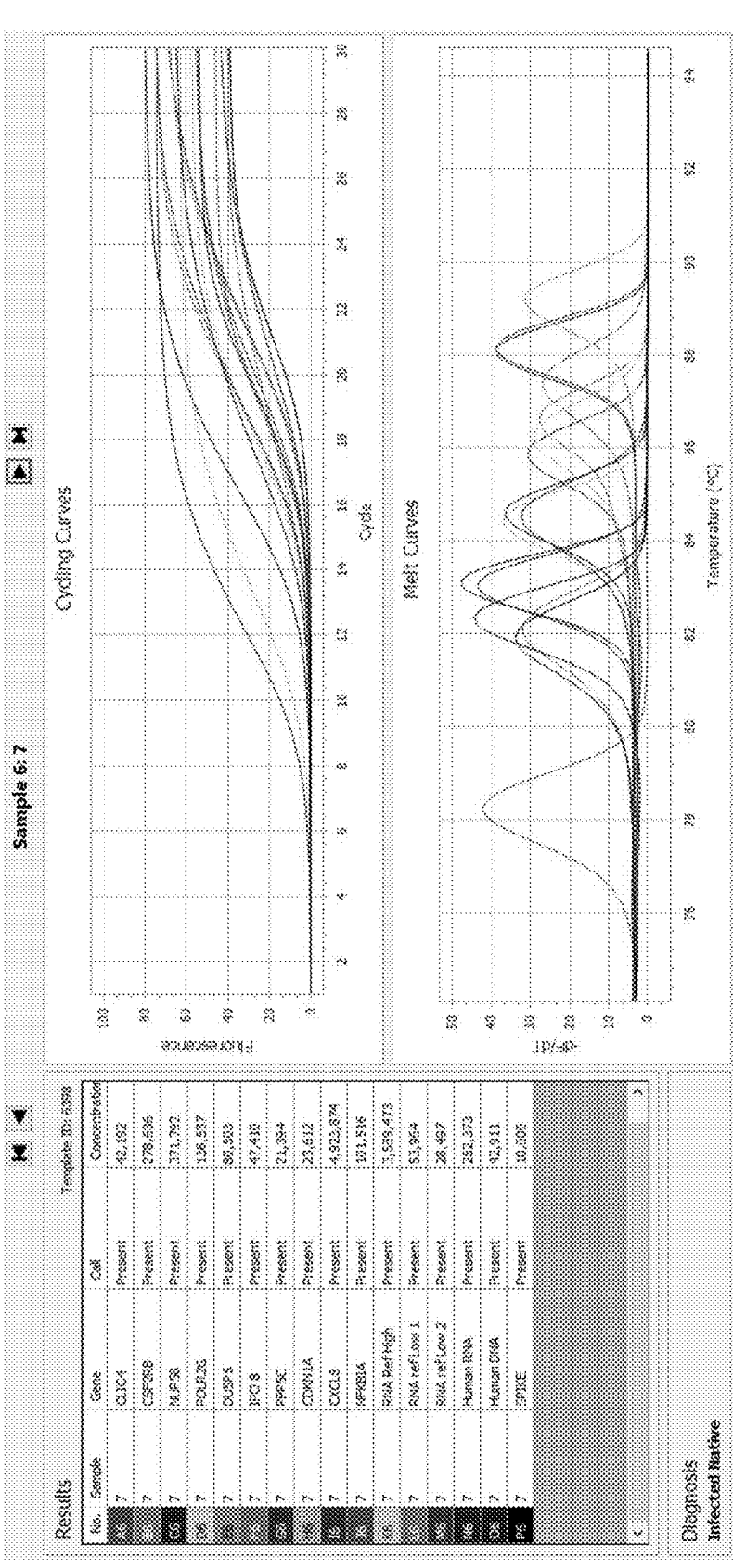
FIG. 13 is an illustration of a typical PCR output depicting cycling curves and melting curves of amplified gene products, representing the expression profile of a biomarker panel including CLIC4, CSF2RB, NUP58, POLR2G, DUSP5, IPO8, PPP5C, CDKN1A, CXCL8 and NFKBIA, in a synovial fluid sample taken from a subject with non-infectious (sterile) joint inflammation.

Representative PCR outputs depicting cycling curves and melting curves of amplified gene products, representing the expression profile of a biomarker panel including CLIC4, CSF2RB, NUP58, POLR2G, DUSP5, IPO8, PPP5C, CDKN1A, CXCL8 and NFKBIA, in a synovial fluid sample taken from a subject with infectious joint inflammation and in a synovial fluid sample taken from a subject with non-infectious (sterile) joint inflammation are shown in FIGS. 12 and 13, respectively. Illustrative primers used for PCR amplification of the biomarkers are as follows:

```
CLIC4:
Forward primer:
                                 (SEQ ID NO: 1)
5'-TCCCAGAGGCTCTTCATGATTCT-3';

Reverse primer:
                                 (SEQ ID NO: 2)
5'-CCGTTTTGACTTCACTGTTGAAAGT-3';

CSF2RB:
Forward primer:
                                 (SEQ ID NO: 3)
5'-CGTCTCTGTTCAGCCAAGGAG-3';

Reverse primer:
                                 (SEQ ID NO: 4)
5'-TGGTCTATGTGTTCGTATCGCATTT-3';

NUP58:
Forward primer:
                                 (SEQ ID NO: 5)
5'-TGTAAAACGACGGCCAGT-3';

Reverse primer:
                                 (SEQ ID NO: 6)
5'-AGGAAACAGCTATGACC-3';

POL2RG:
Forward primer:
                                 (SEQ ID NO: 7)
5'-TGTAAAACGACGGCCAGT-3';

Reverse primer:
                                 (SEQ ID NO: 8)
5'-CAGGAAACAGCTATGACC-3';

DUSP5:
Forward primer:
                                 (SEQ ID NO: 9)
5'-GGCTGACATTAGCTCCCACTTTC-3';

Reverse primer:
                                 (SEQ ID NO: 10)
5'-GGAACTGCTTGGTCTTCATAAGGT-3';

IPO8:
Forward primer:
                                 (SEQ ID NO: 11)
5'-AGGATCAGAGGACAGCACTGCA-3';

Reverse primer:
                                 (SEQ ID NO: 12)
5'-AGGTGAAGCCTCCCTGTTGTTC-3';

PPP5C:
Forward primer:
                                 (SEQ ID NO: 13)
5'-GACTCAGGCCAATGACTACTTCAA-3';

Reverse primer:
                                 (SEQ ID NO: 14)
5'-CGCGTAGCCATAGCACTCA-3';

CDKN1A:
Forward primer:
                                 (SEQ ID NO: 15)
5'-TGTCCGTCAGAACCCATGC-3';

Reverse primer:
                                 (SEQ ID NO: 16)
5'-AAAGTCGAAGTTCCATCGCTC-3';

CXCL8:
Forward primer:
                                 (SEQ ID NO: 17)
5'-ACTGAGAGTGATTGAGAGTGGAC-3';
```

```
                 -continued
Reverse primer:
                                 (SEQ ID NO: 18)
5'-AACCCTCTGCACCCAGTTTTC-3';
and NFKBIA:
Forward primer:
                                 (SEQ ID NO: 19)
5'-GGTGTCCTTGGGTGCTGAT-3';

Reverse primer:
                                 (SEQ ID NO: 20)
5'-AATAGCCCTGGTAGGTAACTCTGT-3'.
```

Example 5

Example Outputs

Illustrative example outputs for a joint inflammation biomarker assay are presented in FIGS. 14 and 15. The format of such reports depends on many factors including: quality control, regulatory authorities, cut-off values, the algorithm used, laboratory and clinician requirements, likelihood of misinterpretation.

One example of a "SynvIchor" assay output is presented in FIG. 14. The result is reported as a number, a position on a 1-3 scale, and a probability of the patient having presence of infectious joint inflammation or non-infectious joint inflammation, based on historical results and the use of a pre-determined cut-off (using results from clinical studies).

Another example of a "SynvIchor" assay output is presented in FIG. 15. The result is reported as a number, a position on a scale of 1-2, and a probability of the patient having presence of infectious joint inflammation or non-infectious joint inflammation, based on historical results and the use of a pre-determined cut-off (using results from clinical studies).

Results of controls within the assay may also be reported. Other information that could be reported might include: previous results and date and time of such results, a prognosis, a scale that provides cut-off values for historical testing results that separate infectious joint inflammation and non-infectious joint inflammation, with increased expression of non-infectious biomarkers for example indicating higher likelihood of non-infectious joint inflammation. The corollary of this holds true. The reporting of results in this fashion would allow clinicians to see the probability of a patient having joint inflammation to enable diagnosis of infectious joint inflammation or non-infectious joint inflammation with confidence.

Example 6

Example Applications of Joint Inflammation Biomarker Signatures

Use of the above described biomarkers and biomarker signatures in patient populations and benefits in respect of differentiating infectious joint inflammation from non-infectious joint inflammation, will now be described.

Once the assay results have been obtained, these results are reported using likelihood ratios as presented for example in FIGS. 14 and 15. As described, the patient may have a range of scoring from 1 to 3 (FIG. 14) or from 1 to 2 (FIG. 15) as either single integers or as a group. For each of the groups there is an assigned infection likelihood that is a derivative of the negative predictive value of that portion of the test output data. Each of these numbers is classified as a "SynvIscore" for ease of interpretation by clinicians. The outputs and correlating values will now be described.

An assay output according to FIG. 14 may be interpreted as follows:

"SynvIscore" of 1: This score correlates with a graphical depiction of the color "green" for visual biases for safety to proceed. This "score" is associated with a very high negative predictive value of 90% or greater, which conveys a very high degree of certainty that the host response is not adopting an infective posture. Consequently, the patient is safer for discharge out of a hospital care setting. Each of the reported results from the SynvIchor test is to be considered in the context of thorough examination, history and other tests including all imaging modalities, biochemical investigations, histological investigation, microbiological investigation and any other measure the assessing clinician deems appropriate for the patient at the time of presentation and diagnosis.

SynvIscore of 2: This score correlates with a graphical depiction of the color "yellow or amber" for visual biases for proceed with some caution. This "score" is associated with an indeterminate infection category, which may represent a period of transition between the low NPV inflammatory state and the high PPV infective state. We recommend that patients who fall into this category a treated with a moderate degree of certainty that the host response may be adopting an infective posture. Consequently, the patient is at an inflection point where certainty to discharge out of a hospital care setting may be reliant on additional measures. Each of the reported results from the SynvIchor test is to be considered in the context of thorough examination, history and other tests including all imaging modalities, biochemical investigations, histological investigation, microbiological investigation and any other measure the assessing clinician deems appropriate for the patient at the time of presentation and diagnosis.

SynvIscore of 3: This score correlates with a graphical depiction of the color "red" for visual biases for patient in danger, stop and assess. This "score" is associated with a positive predictive value of greater than 80%, which conveys a very high degree of certainty that the host response is adopting an infective posture and mounting an infection response. Consequently, the patient may require urgent hospital care with significant intervention beyond antimicrobial dosing. Each of the reported results from the SynvIchor test is to be considered in the context of thorough examination, history and other tests including all imaging modalities, biochemical investigations, histological investigation, microbiological investigation and any other measure the assessing clinician deems appropriate for the patient at the time of presentation and diagnosis.

An assay output according to FIG. 15 may be interpreted as follows:

"SynvIscore" of 1: This score correlates with a graphical depiction of the color "green" for visual biases for safety to proceed. This "score" is associated with a very high negative predictive value of 95% or greater, which conveys a very high degree of certainty that the host response is not adopting an infective posture. Consequently, the patient is safer for discharge out of a hospital care setting. Each of the reported results from the SynvIchor test is to be considered in the context of thorough examination, history and other tests including all imaging modalities, biochemical investigations, histological investigation, microbiological investigation and any other measure the assessing clinician deems appropriate for the patient at the time of presentation and diagnosis.

SynvIscore of 2: This score correlates with a graphical depiction of the color "red" for visual biases for patient in danger, stop and assess. This "score" is associated with a positive predictive value of greater than 80%, which conveys a very high degree of certainty that the host response is adopting an infective posture and mounting an infection response. Consequently, the patient may require urgent hospital care with significant intervention beyond antimicrobial dosing. Each of the reported results from the SynvIchor test is to be considered in the context of thorough examination, history and other tests including all imaging modalities, biochemical investigations, histological investigation, microbiological investigation and any other measure the assessing clinician deems appropriate for the patient at the time of presentation and diagnosis.

The assay outputs are designed to maximize clinical utility by optimizing output for high negative predictive value. In these instances of joint pain presentation, it is far safer to over-treat a non-infectious joint pain with antibiotics than miss or undertreat an infectious joint pain. As a consequence, the threshold for negative results is a high negative predictive value. The tradeoff is a lower positive predictive value relative to the performance of the NPV side of the test.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the disclosure without limiting the disclosure to any one embodiment or specific collection of features. Those of skill in the art will therefore appreciate that, in light of the instant disclosure, various modifications and changes can be made in the particular embodiments exemplified without departing from the scope of the present disclosure. All such modifications and changes are intended to be included within the scope of the appended claims.

What is claimed is:

1. A composition comprising one or more joint inflammation cDNA biomarker synthesis and amplification reaction mixtures, the one or more joint inflammation cDNA biomarker synthesis and amplification reaction mixtures comprising a first reaction mixture comprising:

a) DNA polymerase, b) reverse transcriptase, c) synovial fluid leukocyte whole cell RNA from a synovial joint of a subject, wherein the subject has joint pain in, or has at least one clinical sign of inflammation in, or proximal to, the synovial joint, or has joint pain in and at least one clinical sign of inflammation in, or proximal to, the synovial joint, d) oligonucleotide reverse transcription primers that serve to synthesize at least one joint inflammation cDNA biomarker from the synovial fluid leukocyte whole cell RNA in the presence of the reverse transcriptase, e) POLR2G cDNA synthesized in the first reaction mixture from the synovial fluid leukocyte whole cell RNA by at least one of the oligonucleotide reverse transcription primers and the reverse transcriptase, f) oligonucleotide amplification primers that hybridize to opposite complementary strands of the POLR2G cDNA and that serve to amplify the POLR2G cDNA in the presence of the DNA polymerase, and g) amplified POLR2G cDNA resulting from amplifying the POLR2G cDNA in the first reaction mixture, wherein an amount of amplified POLR2G cDNA in the first reaction mixture is indicative of an amount of POLR2G RNA in the synovial fluid leukocyte whole cell RNA from a synovial joint of a subject.

2. The composition of claim 1, wherein, for each of one or more additional joint inflammation cDNA biomarkers, the first reaction mixture or one or more additional joint inflammation cDNA biomarker synthesis and amplification reaction mixtures that comprise DNA polymerase, reverse transcriptase, and synovial fluid leukocyte whole cell RNA from the subject further comprise:

a) oligonucleotide reverse transcription primers that serve to synthesize the additional joint inflammation cDNA biomarker from the synovial fluid leukocyte whole cell RNA in the presence of the reverse transcriptase, b) the additional joint inflammation cDNA biomarker synthesized in the first reaction mixture or the additional reaction mixture from the synovial fluid leukocyte whole cell RNA by at least one of the oligonucleotide reverse transcription primers and the reverse transcriptase, c) oligonucleotide amplification primers that hybridize to opposite complementary strands of the additional joint inflammation cDNA biomarker and that serve to amplify the additional joint inflammation cDNA biomarker in the presence of the DNA polymerase, and d) amplified additional joint inflammation cDNA biomarker resulting from amplifying the additional joint inflammation cDNA biomarker in the first reaction mixture or the additional reaction mixture, wherein said one or more additional joint inflammation cDNA biomarkers are selected from ACO2, AP3M1, API5, AQP9, ATG4B, ATTIC, C5orf15, CANX, CDKN1A, CISH, CLIC4, CSF2RB, CSF3R, CSNK1D, CWC27, CXCL8, DTNBP1, DUSP1, DUSP5, EIF2S1, EMP1, ERP44, ETV6, FCGR3B, FFAR2, FPR1, FYB1, GADD45B, GBP1, GRINA, H3-3B, HCK, HLA-E, HNRNPAB, IARS2, IER3, IL1B, IL1RN, IMMT, IPO8, IRF2, KCTD2, KCTD3, KLF13, KLHL12, LARP4, LILRB3, LMNA, LRP-PRC, LYN, MCL1, MLLT6, MOCS3, MRPL20, MRPL37, MXD1, MYO1F, NAGA, NAMPT, NFKBIA, NINJ1, NUP58, OSM, PARP14, PDE4B, PI3, PIK3AP1, PIK3R5, PIP4K2B, PKN1, PLAUR, PLEC, PLEK, PLXDC2, POLG2, PPIF, PPIL2, PPP5C, PRPF19, PSMC3, RILPL2, RNASEL, RNF26, SEC24B, SEMA4D, SLC26A6, SNIP1, SNRPF, SP1, SP2, STARD7, STX11, SUSD6, TBK1, TNFAIP2, TNFAIP3, TNFRSF1B, TTYH3, TWF2, VPS4B, VPS51, WIPF2, ZFP36 and ZZEF1.

3. The composition of claim 2, wherein the one or more additional joint inflammation cDNA biomarkers further comprise NFKBIA.

4. The composition of claim 1, wherein the joint inflammation cDNA biomarkers synthesized and amplified in the one or more joint inflammation cDNA biomarker synthesis and amplification reaction mixtures comprise a first joint inflammation cDNA biomarker, a second joint inflammation cDNA biomarker, and a third joint inflammation cDNA biomarker, wherein the first and second joint inflammation cDNA biomarkers are selected from a first set of joint inflammation cDNA biomarkers that are expressed at a higher level in infectious inflammation than in non-infectious inflammation, and wherein the third joint inflammation cDNA biomarker is the POLR2G cDNA biomarker, wherein the first set of joint inflammation cDNA biomarkers consists of AQP9, C5orf15, CANX, CDKN1A, CISH, CLIC4, CSF2RB, CSF3R, CXCL8, DTNBP1, DUSP1, DUSP5, ERP44, ETV6, FCGR3B, FFAR2, FPR1, FYB1, GADD45B, GBP1, GRINA, H3-3B, HCK, HLA-E, IRF2, LILRB3, LYN, MCL1, MLLT6, MXD1, NAMPT, NFKBIA, NINJ1, NUP58, PARP14, PDE4B, PI3, PIK3AP1, PIK3R5, PLAUR, PLEK, RILPL2, RNASEL, SEMA4D, SNIP1, SP1, SP2, STX11, SUSD6, TBK1, TNFAIP2, TNFAIP3, TNFRSF1B and WIPF2.

5. The composition of claim 4, wherein the joint inflammation cDNA biomarkers synthesized and amplified in the one or more joint inflammation cDNA biomarker synthesis and amplification reaction mixtures further comprise a fourth joint inflammation cDNA biomarker, wherein the fourth joint inflammation cDNA biomarker is selected from:

i) a second set of joint inflammation cDNA biomarkers that are expressed at a lower level in infectious inflammation than in non-infectious inflammation, or ii) a third set of joint inflammation cDNA biomarkers that improve discrimination performance of the first and/or second joint inflammation cDNA biomarkers, wherein the second set of joint inflammation cDNA biomarkers consists of ACO2, AP3M1, API5, ATIC, CWC27, EIF2S1, EMP1, IMMT, KLF13, LARP4, LMNA, LRPPRC, MOCS3, MRPL20, MRPL37, NAGA, PIP4K2B, PKN1, PLEC, PLXDC2, PPIL2, PPP5C, PRPF19, PSMC3, RNF26, SNRPF, STARD7, TTYH3, TWF2 and VPS51, and wherein the third set of joint inflammation cDNA biomarkers consists of ATG4B, CSNK1D, IPO8, KCTD2, MYO1F, POLG2 and ZZEF1.

6. The composition of claim 4, comprising a combination of joint inflammation cDNA biomarkers selected from TABLE B;

TABLE B

| Combination | | | | |
| --- | --- | --- | --- | --- |
| 1 | CLIC4 | CSF2RB | POLR2G | — |
| 2 | CLIC4 | CSF2RB | POLR2G | PPP5C |
| 3 | CLIC4 | NUP58 | POLR2G | TTYH3 |

7. The composition of claim 1, wherein the first reaction mixture or one or more additional joint inflammation cDNA biomarker synthesis and amplification reaction mixtures that comprise DNA polymerase, reverse transcriptase, and synovial fluid leukocyte whole cell RNA from the subject further comprise a first additional joint inflammation cDNA biomarker, a second additional joint inflammation cDNA biomarker, and a third additional joint inflammation cDNA biomarker, wherein for each of the first, second, and third additional joint inflammation cDNA biomarkers the first reaction mixture or the one or more additional reaction mixtures comprise:

a) oligonucleotide reverse transcription primers that serve to synthesize the additional joint inflammation cDNA biomarker from the synovial fluid leukocyte whole cell RNA in the presence of the reverse transcriptase, b) the additional joint inflammation cDNA biomarker synthesized in the first reaction mixture or the additional reaction mixture from the synovial fluid leukocyte whole cell RNA by at least one of the oligonucleotide reverse transcription primers and the reverse transcriptase;

c) oligonucleotide amplification primers that hybridize to opposite complementary strands of the additional joint inflammation cDNA biomarker and that serve to amplify the additional joint inflammation cDNA biomarker in the presence of the DNA polymerase, and d) amplified additional joint inflammation cDNA biomarker resulting from amplifying the additional joint inflammation cDNA biomarker in the first reaction mixture or the additional reaction mixture, a) a second set of joint inflammation cDNA biomarkers that are expressed at a lower level in infectious inflammation than in non-infectious inflammation, and/or b) a third set of joint inflammation cDNA biomarkers that improves discrimination performance of the first, second, and third joint inflammation cDNA biomarkers;

wherein the second set of joint inflammation cDNA biomarkers consists of ACO2, AP3M1, API5, EIF2S1, IMMT, KCTD3, KLF13, MOCS3, MRPL20, PKN1, PLEC, PPP5C, PSMC3, RNF26, SNRPF, STARD7 and TTYH3, wherein the third set of joint inflammation cDNA biomarkers consists of ATG4B, CSNK1D, IPO8, KLHL12, MYO1F, POLG2, SEC24B, SLC26A6, VPS4B and ZZEF1.

9. The composition of claim 8, wherein the third set of joint inflammation cDNA biomarkers improves the discrimination performance of the fourth joint inflammation cDNA biomarker.

10. The composition of claim 8, comprising a combination of joint inflammation cDNA biomarkers synthesized and amplified in the first reaction mixture and one or more additional reaction mixtures selected from TABLE C:

TABLE C

| Combination | | | | | | | |
|---|---|---|---|---|---|---|---|
| 1 | CLIC4 | CSF2RB | NUP58 | | IPO8 | POLR2G | |
| 2 | CLIC4 | CSF2RB | NUP58 | | POLR2G | PPP5C | VPS4B |
| 3 | CLIC4 | CSF2RB | DUSP5 | | PLEC | POLR2G | PSMC3 |
| 4 | CLIC4 | CSF2RB | DUSP5 | RNASEL | ATG4B | KLF13 | POLR2G |
| 5 | CLIC4 | CSF2RB | NUP58 | SNIP1 | POLR2G | PPIL2 | VPS4B |
| 6 | CLIC4 | CSF2RB | DUSP5 | | POLR2G | PPP5C | RNF26 |
| 7 | CLIC4 | CSF2RB | NUP58 | | KLHL12 | POLR2G | PPP5C |
| 8 | CLIC4 | NUP58 | SP2 | | PKN1 | PLEC | POLR2G | wherein the first additional joint inflammation cDNA biomarker, second additional joint inflammation cDNA biomarker, and third additional joint inflammation cDNA biomarker are selected from a first set of joint inflammation cDNA biomarkers that are expressed at a higher level in infectious inflammation than in non-infectious inflammation, wherein the first set of joint inflammation cDNA biomarkers consists of AQP9, C5orf15, CANX, CDKN1A, CISH, CLIC4, CSF2RB, CSF3R, CXCL8, DTNBP1, DUSP1, DUSP5, EMP1, ERP44, ETV6, FCGR3B, FFAR2, FPR1, FYB1, GADD45B, GRINA, H3-3B, HCK, HLA-E, IER3, IL1B, IL1RN, IRF2, LILRB3, LMNA, LYN, MCL1, MLLT6, MXD1, NAMPT, NFKBIA, NINJ1, NUP58, OSM, PDE4B, PI3, PIK3AP1, PLAUR, PLEK, PPIF, RILPL2, RNASEL, SEMA4D, SNIP1, SP1, SP2, STX11, SUSD6, TNFAIP2, TNFAIP3, TNFRSF1B, WIPF2 and ZFP36.

8. The composition of claim 7, further comprising at least one of the following:

i) a fourth additional joint inflammation cDNA biomarker,
ii) a fifth additional joint inflammation cDNA biomarker,
iii) a sixth additional joint inflammation cDNA biomarker, and
iv) a seventh additional joint inflammation cDNA biomarker, wherein the fourth additional joint inflammation cDNA biomarker is selected from the first set of joint inflammation cDNA biomarkers, and wherein the fifth, sixth, and seventh additional joint inflammation cDNA biomarkers are selected from:

11. The composition of claim 1, wherein at least one of the one or more joint inflammation cDNA biomarker synthesis and amplification reaction mixtures comprises for a respective joint inflammation cDNA biomarker two pairs of oligonucleotide amplification primers comprising a first pair and a second pair, wherein the oligonucleotide amplification primers of a respective pair hybridize to opposite complementary strands of the cDNA biomarker, and wherein the oligonucleotide amplification primers of the second pair are nested relative to the oligonucleotide amplification primers of the first pair.

12. The composition of claim 1, wherein the composition comprises for a respective joint inflammation cDNA biomarker an oligonucleotide probe that hybridizes to the joint inflammation cDNA biomarker or a polynucleotide corresponding thereto.

13. The composition of claim 12, wherein the oligonucleotide probe comprises a heterologous reporter molecule.

14. The composition of claim 13, wherein the reporter molecule comprises a fluorescent label.

15. The composition of claim 12, wherein the oligonucleotide probe is a real-time polymerase chain reaction probe.

16. The composition of claim 12, wherein the composition comprises for each of up to 10 joint inflammation cDNA biomarkers at least one oligonucleotide probe that hybridizes to the joint inflammation cDNA biomarker or a polynucleotide corresponding thereto.

17. The composition of claim 1, wherein the first reaction mixture further comprises a second joint inflammation cDNA biomarker synthesized and amplified in the first reaction mixture, wherein at least one oligonucleotide probe is hybridized to a complementary nucleic acid sequence in the second joint inflammation cDNA biomarker.

18. The composition of claim 1, wherein the DNA polymerase is a thermostable DNA polymerase.

* * * * *

SEQUENCE LISTING

```
Sequence total quantity: 20
SEQ ID NO: 1            moltype = DNA   length = 23
FEATURE                 Location/Qualifiers
source                  1..23
                        mol_type = other DNA
                        organism = synthetic construct
SEQUENCE: 1
tcccagaggc tcttcatgat tct                                      23

SEQ ID NO: 2            moltype = DNA   length = 25
FEATURE                 Location/Qualifiers
```

-continued

```
source                   1..25
                         mol_type = other DNA
                         organism = synthetic construct
SEQUENCE: 2
ccgttttgac ttcactgttg aaagt                                              25

SEQ ID NO: 3             moltype = DNA   length = 21
FEATURE                  Location/Qualifiers
source                   1..21
                         mol_type = other DNA
                         organism = synthetic construct
SEQUENCE: 3
cgtctctgtt cagccaagga g                                                  21

SEQ ID NO: 4             moltype = DNA   length = 25
FEATURE                  Location/Qualifiers
source                   1..25
                         mol_type = other DNA
                         organism = synthetic construct
SEQUENCE: 4
tggtctatgt gttcgtatcg cattt                                              25

SEQ ID NO: 5             moltype = DNA   length = 18
FEATURE                  Location/Qualifiers
source                   1..18
                         mol_type = other DNA
                         organism = synthetic construct
SEQUENCE: 5
tgtaaaacga cggccagt                                                      18

SEQ ID NO: 6             moltype = DNA   length = 17
FEATURE                  Location/Qualifiers
source                   1..17
                         mol_type = other DNA
                         organism = synthetic construct
SEQUENCE: 6
aggaaacagc tatgacc                                                       17

SEQ ID NO: 7             moltype = DNA   length = 18
FEATURE                  Location/Qualifiers
source                   1..18
                         mol_type = other DNA
                         organism = synthetic construct
SEQUENCE: 7
tgtaaaacga cggccagt                                                      18

SEQ ID NO: 8             moltype = DNA   length = 18
FEATURE                  Location/Qualifiers
source                   1..18
                         mol_type = other DNA
                         organism = synthetic construct
SEQUENCE: 8
caggaaacag ctatgacc                                                      18

SEQ ID NO: 9             moltype = DNA   length = 23
FEATURE                  Location/Qualifiers
source                   1..23
                         mol_type = other DNA
                         organism = synthetic construct
SEQUENCE: 9
ggctgacatt agctcccact ttc                                                23

SEQ ID NO: 10            moltype = DNA   length = 24
FEATURE                  Location/Qualifiers
source                   1..24
                         mol_type = other DNA
                         organism = synthetic construct
SEQUENCE: 10
ggaactgctt ggtcttcata aggt                                               24

SEQ ID NO: 11            moltype = DNA   length = 22
FEATURE                  Location/Qualifiers
source                   1..22
                         mol_type = other DNA
                         organism = synthetic construct
SEQUENCE: 11
aggatcagag gacagcactg ca                                                 22

SEQ ID NO: 12            moltype = DNA   length = 22
```

-continued

```
FEATURE                  Location/Qualifiers
source                   1..22
                         mol_type = other DNA
                         organism = synthetic construct
SEQUENCE: 12
aggtgaagcc tccctgttgt tc                                           22

SEQ ID NO: 13            moltype = DNA   length = 24
FEATURE                  Location/Qualifiers
source                   1..24
                         mol_type = other DNA
                         organism = synthetic construct
SEQUENCE: 13
gactcaggcc aatgactact tcaa                                         24

SEQ ID NO: 14            moltype = DNA   length = 19
FEATURE                  Location/Qualifiers
source                   1..19
                         mol_type = other DNA
                         organism = synthetic construct
SEQUENCE: 14
cgcgtagcca tagcactca                                               19

SEQ ID NO: 15            moltype = DNA   length = 19
FEATURE                  Location/Qualifiers
source                   1..19
                         mol_type = other DNA
                         organism = synthetic construct
SEQUENCE: 15
tgtccgtcag aacccatgc                                               19

SEQ ID NO: 16            moltype = DNA   length = 21
FEATURE                  Location/Qualifiers
source                   1..21
                         mol_type = other DNA
                         organism = synthetic construct
SEQUENCE: 16
aaagtcgaag ttccatcgct c                                            21

SEQ ID NO: 17            moltype = DNA   length = 23
FEATURE                  Location/Qualifiers
source                   1..23
                         mol_type = other DNA
                         organism = synthetic construct
SEQUENCE: 17
actgagagtg attgagagtg gac                                          23

SEQ ID NO: 18            moltype = DNA   length = 21
FEATURE                  Location/Qualifiers
source                   1..21
                         mol_type = other DNA
                         organism = synthetic construct
SEQUENCE: 18
aaccctctgc acccagtttt c                                            21

SEQ ID NO: 19            moltype = DNA   length = 19
FEATURE                  Location/Qualifiers
source                   1..19
                         mol_type = other DNA
                         organism = synthetic construct
SEQUENCE: 19
ggtgtccttg ggtgctgat                                               19

SEQ ID NO: 20            moltype = DNA   length = 24
FEATURE                  Location/Qualifiers
source                   1..24
                         mol_type = other DNA
                         organism = synthetic construct
SEQUENCE: 20
aatagccctg gtaggtaact ctgt                                         24
```